(12) United States Patent
Henley

(10) Patent No.: US 11,992,585 B2
(45) Date of Patent: May 28, 2024

(54) ELECTRO-IONIC DEVICES FOR IMPROVED PROTECTION FROM AIRBORNE BIOPATHOGENS

(71) Applicant: Julian Henley, New Orleans, LA (

Related U.S. Application Data filed on Aug. 11, 2020, provisional application No. 63/044,768, filed on Jun. 26, 2020, provisional application No. 63/043,424, filed on Jun. 24, 2020, provisional application No. 63/027,746, filed on May 20, 2020, provisional application No. 62/988,991, filed on Mar. 13, 2020.

(51) Int. Cl.

| | | |
|---|---|---|
| *A61L 9/12* | (2006.01) | |
| *A61L 9/16* | (2006.01) | |
| *B03C 3/017* | (2006.01) | |
| *B03C 3/155* | (2006.01) | |
| *B03C 3/41* | (2006.01) | |
| *B03C 3/47* | (2006.01) | |
| *F24F 3/16* | (2021.01) | |
| *F24F 8/30* | (2021.01) | |
| *F24F 8/40* | (2021.01) | |
| *F24F 8/80* | (2021.01) | |

(52) U.S. Cl.
CPC .............. *B03C 3/017* (2013.01); *B03C 3/155* (2013.01); *B03C 3/41* (2013.01); *B03C 3/47* (2013.01); *F24F 3/16* (2013.01); *F24F 8/30* (2021.01); *F24F 8/40* (2021.01); *F24F 8/80* (2021.01); *A61L 2209/111* (2013.01); *A61L 2209/14* (2013.01); *A61L 2209/16* (2013.01); *B03C 2201/04* (2013.01); *B03C 2201/08* (2013.01); *F24F 2221/34* (2013.01)

(58) Field of Classification Search
CPC .... A61L 9/20; A61L 9/22; A61L 9/015; F24F 8/30; F24F 8/80; F24F 8/40; F24F 3/16; F24F 2221/34; A62B 7/10; A62B 23/00; A62B 17/04; A62B 17/006; B03C 3/017; B03C 3/155; B03C 3/41; B03C 3/47; B03C 2201/04; B03C 2201/08; B03C 3/38; B03C 3/32; B03C 3/66; B03C 3/12; Y10S 323/903; B01D 2257/504; B01D 2257/91; B01D 2259/4558; B01D 253/102; B01D 2259/804; B01D 53/38; B01D 2259/4541; B01D 2251/104; B01D 2259/4566; B01D 53/86; B01D 2259/4583; C01B 13/10; C01B 13/11; C01B 2201/82; Y02P 20/151
See application file for complete search history.

(56) References Cited

U.S. PATENT DOCUMENTS

| | | |
|---|---|---|
| 3,626,668 A | 12/1971 | Cardiff |
| 3,977,467 A | 8/1976 | Northrup, Jr. |
| 4,502,872 A | 3/1985 | Ivester et al. |
| 5,447,763 A | 9/1995 | Gehlke |
| 5,573,577 A | 11/1996 | Joannou |
| 5,578,112 A | 11/1996 | Krause |
| 5,648,046 A | 7/1997 | Weibel |
| 5,820,828 A | 10/1998 | Ferone |
| 5,887,439 A | 3/1999 | Kotliar |
| 5,919,847 A | 7/1999 | Rousseau et al. |
| 5,924,419 A | 7/1999 | Kotliar |
| 5,964,222 A | 10/1999 | Kotliar |
| 5,968,635 A | 10/1999 | Rousseau et al. |
| 5,976,208 A | 11/1999 | Rousseau et al. |
| 5,988,161 A | 11/1999 | Kroll |
| 6,002,017 A | 12/1999 | Rousseau et al. |
| 6,019,949 A | 2/2000 | Dunder |
| 6,029,664 A | 2/2000 | Zdrojkowski et al. |
| 6,042,637 A * | 3/2000 | Weinberg .................. B03C 3/38 96/97 |
| 6,056,808 A | 5/2000 | Krause |
| 6,073,627 A | 6/2000 | Sunnen |
| 6,117,176 A | 9/2000 | Chen |
| 6,119,691 A | 9/2000 | Angadjivand et al. |
| 6,162,535 A | 12/2000 | Turkevich et al. |
| 6,192,911 B1 | 2/2001 | Barnes |
| 6,213,122 B1 | 4/2001 | Rousseau et al. |
| 6,214,094 B1 | 4/2001 | Rousseau et al. |
| 6,237,595 B1 | 5/2001 | Rousseau et al. |
| 6,238,466 B1 | 5/2001 | Rousseau et al. |
| 6,240,933 B1 | 6/2001 | Bergman |
| 6,261,342 B1 | 7/2001 | Rousseau et al. |
| 6,267,125 B1 | 7/2001 | Bergman et al. |
| 6,268,495 B1 | 7/2001 | Rousseau et al. |
| 6,273,108 B1 | 8/2001 | Bergman et al. |
| 6,281,515 B1 | 8/2001 | Demeo et al. |
| 6,305,374 B1 | 10/2001 | Zdrojkowski et al. |
| 6,314,754 B1 | 11/2001 | Kotliar |
| 6,324,703 B1 | 12/2001 | Chen |
| 6,333,374 B1 | 12/2001 | Chen |
| 6,334,315 B1 | 1/2002 | Kotliar |
| 6,365,103 B1 | 4/2002 | Fournier |
| 6,375,714 B1 | 4/2002 | Rump et al. |
| 6,375,886 B1 | 4/2002 | Angadjivand et al. |
| 6,401,487 B1 | 6/2002 | Kotliar |
| 6,405,387 B1 | 6/2002 | Barnes |
| 6,406,657 B1 | 6/2002 | Eitzman et al. |
| 6,426,053 B1 | 7/2002 | Barnes |
| 6,428,756 B1 | 8/2002 | Barnes |
| 6,432,077 B1 | 8/2002 | Stenzler |
| 6,432,367 B1 | 8/2002 | Munk |
| 6,488,634 B1 | 12/2002 | Rapoport et al. |
| 6,502,421 B2 | 1/2003 | Kotliar |
| 6,539,940 B2 | 4/2003 | Zdrojkowski et al. |
| 6,557,374 B2 | 5/2003 | Kotliar |
| 6,560,991 B1 | 5/2003 | Kotliar |
| 6,561,185 B1 | 5/2003 | Kroll |
| 6,582,525 B2 | 6/2003 | Bergman |
| 6,591,845 B1 | 7/2003 | Bergman et al. |
| 6,601,594 B2 | 8/2003 | Bergman et al. |
| 6,614,505 B2 | 9/2003 | Koster et al. |
| 6,623,635 B2 | 9/2003 | Barnes |
| 6,627,563 B1 | 9/2003 | Huberty |
| 6,629,527 B1 | 10/2003 | Estes et al. |
| 6,701,941 B1 | 3/2004 | Bergman et al. |
| 6,745,764 B2 | 6/2004 | Hickle |
| 6,776,951 B2 | 8/2004 | Rousseau et al. |
| 6,793,644 B2 | 9/2004 | Stenzler |
| 6,807,965 B1 | 10/2004 | Hickle |
| 6,817,370 B2 | 11/2004 | Bergman et al. |
| 6,820,619 B2 | 11/2004 | Kroll |
| 6,828,578 B2 | 12/2004 | DeMeo et al. |
| 6,830,628 B2 | 12/2004 | Bergman |
| 6,837,252 B2 | 1/2005 | Bergman |
| 6,841,791 B2 | 1/2005 | DeMeo et al. |
| 6,843,857 B2 | 1/2005 | Bergman |
| 6,854,135 B2 | 2/2005 | Jones et al. |
| 6,862,075 B2 | 3/2005 | Koster et al. |
| 6,867,253 B1 | 3/2005 | Chen |
| 6,869,487 B1 | 3/2005 | Bergman |
| 6,901,930 B2 * | 6/2005 | Henley .................... B03C 3/12 128/205.27 |
| 6,948,497 B2 | 9/2005 | Zdrojkowski et al. |
| 6,986,347 B2 | 1/2006 | Hickle |
| 6,991,532 B2 | 1/2006 | Goldsmith |
| 6,997,180 B2 | 2/2006 | Kroll |
| 7,008,465 B2 | 3/2006 | Graham et al. |
| 7,013,892 B2 | 3/2006 | Estes et al. |
| 7,025,869 B2 | 4/2006 | Fine et al. |
| 7,028,689 B2 | 4/2006 | Martin et al. |
| 7,040,313 B2 | 5/2006 | Fine et al. |
| 7,047,970 B2 | 5/2006 | Umeda et al. |
| 7,122,018 B2 | 10/2006 | Stenzler et al. |
| 7,135,108 B1 | 11/2006 | Barnes |
| 7,148,085 B2 | 12/2006 | Abbott et al. |
| 7,201,734 B2 | 4/2007 | Hickle |
| 7,203,974 B2 | 4/2007 | Jones et al. |
| 7,244,291 B2 | 7/2007 | Spartz et al. |
| 7,244,292 B2 | 7/2007 | Kirk et al. |

(56) References Cited

U.S. PATENT DOCUMENTS

| | | |
|---|---|---|
| 7,247,154 B2 | 7/2007 | Hickle |
| 7,308,894 B2 | 12/2007 | Hickle |
| RE40,065 E | 2/2008 | Kotliar |
| 7,332,019 B2 | 2/2008 | Bias et al. |
| 7,334,580 B2 | 2/2008 | Smaldone et al. |
| 7,335,181 B2 | 2/2008 | Miller et al. |
| 7,351,274 B2 | 4/2008 | Helt et al. |
| 7,390,351 B2 | 6/2008 | Leir et al. |
| 7,520,866 B2 | 4/2009 | Stenzler et al. |
| 7,564,201 B2 | 7/2009 | Steckling |
| 7,578,997 B2 | 8/2009 | MacDonald |
| 7,601,204 B2 | 10/2009 | Woodruff et al. |
| 7,607,436 B2 | 10/2009 | Smaldone et al. |
| 7,647,927 B2 | 1/2010 | Teezel et al. |
| 7,658,891 B1 * | 2/2010 | Barnes ............... C01B 13/11  128/205.28 |
| 7,765,698 B2 | 8/2010 | Sebastian et al. |
| 7,802,572 B2 | 9/2010 | Hahne |
| 7,887,889 B2 | 2/2011 | David et al. |
| 7,892,198 B2 | 2/2011 | Stenzler |
| 7,909,918 B2 | 3/2011 | Bias et al. |
| 7,931,733 B2 | 4/2011 | Kotliar |
| 7,955,418 B2 | 6/2011 | Claussen et al. |
| 7,975,692 B2 | 7/2011 | Eifler et al. |
| 7,976,855 B2 | 7/2011 | MacDonald et al. |
| 7,992,556 B2 | 8/2011 | Hickle |
| 8,015,970 B2 | 9/2011 | Klun et al. |
| 8,043,252 B2 | 10/2011 | Miller et al. |
| 8,062,411 B2 | 11/2011 | Blucher et al. |
| 8,066,904 B2 | 11/2011 | Fine et al. |
| 8,067,110 B2 | 11/2011 | Rakow et al. |
| 8,072,291 B2 | 12/2011 | Itoh et al. |
| 8,113,198 B2 | 2/2012 | Teetzel et al. |
| 8,182,800 B2 | 5/2012 | MacDonald |
| 8,221,800 B2 | 7/2012 | Fine et al. |
| 8,245,708 B2 | 8/2012 | Smaldone et al. |
| 8,261,747 B2 | 9/2012 | Smaldone et al. |
| 8,298,320 B2 | 10/2012 | Cozean |
| 8,303,693 B2 | 11/2012 | Leung |
| 8,334,524 B2 | 12/2012 | DeMeo et al. |
| 8,356,594 B2 | 1/2013 | Ujhazy et al. |
| 8,366,816 B2 | 2/2013 | Bohringer et al. |
| 8,371,296 B2 | 2/2013 | Fine et al. |
| 8,388,731 B2 | 3/2013 | Metteer |
| 8,397,715 B2 | 3/2013 | Litz |
| 8,416,033 B2 | 4/2013 | Itoh et al. |
| 8,480,797 B2 | 7/2013 | Cozean et al. |
| 8,585,808 B2 | 11/2013 | Croll et al. |
| 8,602,023 B2 | 12/2013 | Smaldone et al. |
| 8,613,795 B2 | 12/2013 | Li et al. |
| 8,647,419 B2 | 2/2014 | Kaskel |
| 8,653,979 B2 | 2/2014 | Obenchain |
| 8,667,960 B2 | 3/2014 | Ausen |
| 8,673,061 B2 | 3/2014 | Cozean et al. |
| 8,684,189 B2 | 4/2014 | Chen et al. |
| 8,714,156 B2 | 5/2014 | Cooke et al. |
| 8,733,350 B2 | 5/2014 | Smaldone et al. |
| 8,753,434 B2 | 6/2014 | Croll et al. |
| 8,757,154 B2 | 6/2014 | Schuller |
| 8,763,712 B2 | 7/2014 | Kotliar |
| 8,765,133 B2 | 7/2014 | Tsukamoto |
| 8,776,796 B2 | 7/2014 | Nolan |
| 8,790,449 B2 | 7/2014 | Li et al. |
| 8,795,222 B2 | 8/2014 | Stenzler et al. |
| 8,815,244 B2 | 8/2014 | Tsukamoto |
| 8,845,782 B2 | 9/2014 | Metteer |
| 8,859,995 B2 | 10/2014 | Liu et al. |
| 8,882,703 B2 | 11/2014 | Hickle |
| 8,887,719 B2 | 11/2014 | Billingsley et al. |
| 8,887,726 B2 | 11/2014 | Schulz et al. |
| 8,899,227 B2 | 12/2014 | Billingsley et al. |
| 8,944,048 B2 | 2/2015 | Monzyk |
| 8,950,401 B2 | 2/2015 | Teetzel et al. |
| 8,955,515 B2 | 2/2015 | Rakow et al. |
| 8,960,194 B2 | 2/2015 | Cooke et al. |
| 8,967,147 B2 | 3/2015 | Martin |
| 9,011,584 B2 | 4/2015 | Tobias et al. |
| 9,079,049 B2 | 7/2015 | Tobias et al. |
| 9,095,422 B2 | 8/2015 | Gray et al. |
| 9,120,571 B2 | 9/2015 | Kshirsagar et al. |
| 9,127,363 B2 | 9/2015 | David et al. |
| 9,127,691 B2 | 9/2015 | Hagen et al. |
| 9,132,251 B2 | 9/2015 | Johansen |
| 9,132,252 B2 | 9/2015 | Barlow et al. |
| 9,155,923 B2 | 10/2015 | Proctor |
| 9,171,689 B2 | 10/2015 | Liu et al. |
| 9,186,472 B2 | 11/2015 | Cozean et al. |
| 9,192,626 B2 | 11/2015 | Willoughby et al. |
| 9,200,804 B2 | 12/2015 | Park et al. |
| 9,220,858 B2 | 12/2015 | Nolan |
| 9,248,248 B2 | 2/2016 | Virr et al. |
| 9,283,341 B2 | 3/2016 | Ujhazy et al. |
| 9,284,669 B2 | 3/2016 | Li et al. |
| 9,308,492 B2 | 4/2016 | Obee et al. |
| 9,333,378 B2 | 5/2016 | Ishikawa et al. |
| 9,353,966 B2 | 5/2016 | Finkam |
| 9,393,448 B2 | 7/2016 | Dwyer et al. |
| 9,421,515 B2 | 8/2016 | Yoshizaki et al. |
| 9,440,219 B2 | 9/2016 | Bohringer et al. |
| 9,440,775 B2 | 9/2016 | Dwyer et al. |
| 9,457,207 B2 | 10/2016 | Waterford |
| 9,481,424 B2 | 11/2016 | Hagen et al. |
| 9,492,690 B2 | 11/2016 | Hamerly et al. |
| 9,506,173 B2 | 11/2016 | Iwata et al. |
| 9,550,570 B2 | 1/2017 | Kshirsagar et al. |
| 9,580,177 B2 | 2/2017 | Kshirsagar et al. |
| 9,623,404 B2 | 4/2017 | Hupp et al. |
| 9,642,868 B2 | 5/2017 | Wei |
| 9,714,860 B2 | 7/2017 | Obenchain |
| 9,744,328 B2 | 8/2017 | Billingsley et al. |
| 9,744,329 B2 | 8/2017 | Billingsley et al. |
| 9,757,530 B2 | 9/2017 | Nolan |
| 9,802,014 B2 | 10/2017 | Nolan |
| 9,808,655 B2 | 11/2017 | Fromage |
| 9,820,881 B2 | 11/2017 | Aarestad et al. |
| 9,821,291 B2 | 11/2017 | Wood |
| 9,861,774 B2 | 1/2018 | Fu et al. |
| 9,895,382 B2 | 2/2018 | Wei |
| 9,901,128 B2 | 2/2018 | Gray et al. |
| 9,956,232 B2 | 5/2018 | Wei |
| 9,956,371 B2 | 5/2018 | De Vries et al. |
| 9,968,809 B2 | 5/2018 | Ryu et al. |
| 9,998,804 B2 | 6/2018 | Awiszus et al. |
| 10,004,858 B2 | 6/2018 | Smaldone et al. |
| 10,035,128 B2 | 7/2018 | Wood |
| 10,046,134 B2 | 8/2018 | De Vries et al. |
| 10,092,442 B2 | 10/2018 | Aarestad et al. |
| 10,099,072 B2 | 10/2018 | LeVan, Jr. et al. |
| 10,099,165 B2 | 10/2018 | Walls et al. |
| 10,105,509 B2 | 10/2018 | De Vries et al. |
| 10,112,026 B2 | 10/2018 | Schulz et al. |
| 10,130,831 B2 | 11/2018 | Teetzel et al. |
| 10,130,833 B2 | 11/2018 | Angadjivand et al. |
| 10,143,948 B2 | 12/2018 | Bonifas et al. |
| 10,182,946 B2 | 1/2019 | Gray et al. |
| 10,195,217 B2 | 2/2019 | Wei |
| 10,201,198 B2 | 2/2019 | Tong et al. |
| 10,213,629 B2 | 2/2019 | Tobias |
| 10,238,822 B2 | 3/2019 | Barlow et al. |
| 10,245,406 B2 | 4/2019 | De Vries et al. |
| 10,272,279 B2 | 4/2019 | Hupp et al. |
| 10,315,002 B2 | 6/2019 | De Vries et al. |
| 10,322,303 B2 | 6/2019 | Qian et al. |
| 10,328,625 B2 | 6/2019 | Gray et al. |
| 10,343,000 B2 | 7/2019 | Givens et al. |
| 10,369,320 B2 | 8/2019 | Ahmad et al. |
| 10,387,696 B2 | 8/2019 | Hamerly et al. |
| 10,441,828 B2 | 10/2019 | Curran et al. |
| 10,456,724 B2 | 10/2019 | Huang et al. |
| 10,464,001 B2 | 11/2019 | Kirk et al. |
| 10,485,940 B2 | 11/2019 | Nolan |
| 10,512,429 B2 | 12/2019 | Lau et al. |
| 10,518,059 B2 | 12/2019 | Cipollone et al. |
| 10,537,755 B2 | 1/2020 | Parham et al. |

(56) References Cited

U.S. PATENT DOCUMENTS

| | | |
|---|---|---|
| 10,542,332 B2 | 1/2020 | Awiszus et al. |
| 10,561,863 B1 | 2/2020 | Dashevsky et al. |
| 10,576,237 B2 | 3/2020 | De Vries et al. |
| 10,610,708 B2 | 4/2020 | Awiszus et al. |
| 10,617,894 B2 | 4/2020 | Nien O et al. |
| 10,625,186 B2 | 4/2020 | Bonifas et al. |
| 10,653,552 B2 | 5/2020 | Aarestad et al. |
| 10,691,908 B2 | 6/2020 | Howard et al. |
| 10,695,521 B2 | 6/2020 | Harrington |
| 10,709,855 B2 | 7/2020 | Nolan |
| 10,722,477 B2 | 7/2020 | Wei |
| 10,744,351 B2 | 8/2020 | Fujimori et al. |
| 10,751,660 B2 | 8/2020 | Legare et al. |
| 10,758,699 B2 | 9/2020 | Cipollone et al. |
| 10,758,751 B2 | 9/2020 | Feasey et al. |
| 10,786,691 B2 | 9/2020 | Kao et al. |
| 10,786,693 B1 | 9/2020 | Opperman et al. |
| 10,814,261 B2 | 10/2020 | Jinka et al. |
| 10,817,683 B2 | 10/2020 | Hamerly et al. |
| 10,821,243 B2 | 11/2020 | Obenchain |
| 10,821,255 B2 | 11/2020 | Zereshkian |
| 10,834,980 B2 | 11/2020 | Magidson et al. |
| 10,849,790 B2 | 12/2020 | Awiszus et al. |
| 10,856,802 B2 | 12/2020 | Ujhazy et al. |
| 10,867,224 B2 | 12/2020 | Howard et al. |
| 10,874,810 B2 | 12/2020 | Fu et al. |
| 10,874,891 B2 | 12/2020 | Biemelt et al. |
| 10,912,961 B2 | 2/2021 | Seo et al. |
| 10,926,114 B2 | 2/2021 | Thompson et al. |
| 10,929,730 B2 | 2/2021 | Shannon et al. |
| 10,932,505 B1 | 3/2021 | Ward et al. |
| 10,946,223 B2 | 3/2021 | Morgan, III et al. |
| 10,953,248 B2 | 3/2021 | Yu et al. |
| 10,960,341 B2 | 3/2021 | Wendland et al. |
| 10,967,207 B2 | 4/2021 | Son et al. |
| 10,981,022 B2 | 4/2021 | Zhao et al. |
| 11,000,827 B2 | 5/2021 | Maanum et al. |
| 11,007,339 B2 | 5/2021 | Reeh et al. |
| 11,007,341 B2 | 5/2021 | Schuller |
| 11,014,070 B2 | 5/2021 | Kobe et al. |
| 11,023,818 B2 | 6/2021 | Awiszus et al. |
| 11,027,236 B2 | 6/2021 | Maayan et al. |
| 11,033,763 B2 | 6/2021 | Nguyen et al. |
| 11,045,787 B2 | 6/2021 | Kobe et al. |
| 11,052,169 B1 | 7/2021 | Pisharodi |
| 11,071,840 B2 | 7/2021 | Reeh et al. |
| 11,077,394 B2 | 8/2021 | Smith |
| 11,083,863 B2 | 8/2021 | Schulz et al. |
| 11,090,515 B2 | 8/2021 | Schuller |
| 11,090,589 B2 | 8/2021 | Bansal et al. |
| 11,103,159 B2 | 8/2021 | Harshman et al. |
| 11,103,822 B2 | 8/2021 | Wendland et al. |
| 11,110,306 B2 | 9/2021 | Montoya et al. |
| 11,123,510 B2 | 9/2021 | Mauger et al. |
| 11,172,845 B1 | 11/2021 | Everman et al. |
| 11,185,655 B2 | 11/2021 | Cipollone et al. |
| 11,213,639 B2 | 1/2022 | Barlow et al. |
| 11,219,788 B2 | 1/2022 | Dwyer et al. |
| 11,235,183 B1 | 2/2022 | Dashevsky et al. |
| 11,247,015 B2 | 2/2022 | De Vries et al. |
| 11,250,303 B2 | 2/2022 | Howard et al. |
| 11,260,251 B2 | 3/2022 | Awiszus et al. |
| 11,273,333 B2 | 3/2022 | Sabolis et al. |
| 11,278,832 B2 | 3/2022 | Jasuja et al. |
| 11,291,255 B2 | 4/2022 | Kanukurthy et al. |
| 11,291,791 B2 | 4/2022 | De Vries et al. |
| 11,300,716 B2 | 4/2022 | Wheatley et al. |
| 11,305,135 B2 | 4/2022 | Givens et al. |
| 11,314,971 B2 | 4/2022 | Ylitalo et al. |
| 11,343,598 B2 | 5/2022 | Awiszus et al. |
| 11,344,692 B2 | 5/2022 | Cipollone et al. |
| 11,354,523 B2 | 6/2022 | Hamerly et al. |
| 11,357,882 B2 | 6/2022 | Dunbar |
| 11,358,014 B2 | 6/2022 | Farmer et al. |
| 11,373,076 B2 | 6/2022 | McCoy et al. |
| 11,375,761 B2 | 7/2022 | Hsien |
| 11,376,451 B2 | 7/2022 | Schuller |
| 11,389,397 B2 | 7/2022 | Wei |
| 11,389,462 B2 | 7/2022 | Wei |
| 11,389,676 B2 | 7/2022 | Schuller |
| 11,406,649 B2 | 8/2022 | Wei |
| 11,452,793 B1 | 9/2022 | Fulbrook |
| 2002/0014401 A1 | 2/2002 | Fleischer |
| 2003/0072675 A1 | 4/2003 | Takeda et al. |
| 2004/0041564 A1 | 3/2004 | Brown |
| 2004/0216745 A1 | 11/2004 | Yuen et al. |
| 2004/0262241 A1 | 12/2004 | Socha |
| 2005/0129571 A1 | 6/2005 | Centanni |
| 2005/0186108 A1 | 8/2005 | Fields |
| 2005/0207951 A1 | 9/2005 | Lee |
| 2006/0079168 A1 | 4/2006 | Goldsmith |
| 2006/0104858 A1 | 5/2006 | Potember et al. |
| 2006/0130663 A1 | 6/2006 | Joshi et al. |
| 2008/0075639 A1 | 3/2008 | Hooper et al. |
| 2008/0199351 A1 | 8/2008 | Woodbridge |
| 2009/0126382 A1 | 5/2009 | Rubino et al. |
| 2010/0089240 A1 | 4/2010 | Krichtafovitch |
| 2010/0114011 A1 | 5/2010 | Herrmann |
| 2010/0307332 A1 | 12/2010 | Yuen |
| 2011/0087084 A1 | 4/2011 | Jeong et al. |
| 2016/0146483 A1 | 5/2016 | Sakai et al. |
| 2017/0136270 A1 | 5/2017 | Son et al. |
| 2017/0258150 A1 | 9/2017 | Abdulqader et al. |
| 2017/0354978 A1 | 12/2017 | Krichtafovitch |
| 2018/0064968 A1 | 3/2018 | Taslagyan |
| 2020/0188932 A1 | 6/2020 | Krichtafovitch |
| 2021/0322799 A1 | 10/2021 | Pachoud et al. |
| 2021/0330853 A1 | 10/2021 | Mizandari |
| 2022/0040504 A1 | 2/2022 | Johnston et al. |
| 2023/0094157 A1 | 3/2023 | Henley |
| 2024/0001053 A1 | 1/2024 | Henley |
| 2024/0001176 A1 | 1/2024 | Henley |
| 2024/0001375 A1 | 1/2024 | Henley |

FOREIGN PATENT DOCUMENTS

| | | |
|---|---|---|
| EP | 1905458 B1 | 11/2018 |
| ES | 1073677 U | 1/2011 |
| GB | 2467221 A | 7/2010 |
| JP | H 0975436 A | 3/1997 |
| JP | 2016501589 A | 1/2016 |
| JP | 2018136315 A | 8/2018 |
| KR | 101507559 B1 | 3/2015 |
| WO | WO 2005/060366 A2 | 7/2005 |
| WO | WO 2005/087320 A1 | 9/2005 |
| WO | WO 2010/103296 A2 | 9/2010 |
| WO | WO 2014/082120 A1 | 6/2014 |
| WO | WO 2019/012043 A1 | 1/2019 |
| WO | WO 2020/039379 A1 | 2/2020 |

OTHER PUBLICATIONS

International Searching Authority, International Search Report and Written Opinion, issued in connection with International Application No. PCT/US2021/022392, dated Jul. 28, 2021, 14 pgs.
International Searching Authority, International Search Report and Written Opinion, issued in connection with International Application No. PCT/US2022/071174, dated Aug. 1, 2022, 20 pgs.
International Searching Authority, International Search Report and Written Opinion, issued in connection with International Application No. PCT/US2022/071169, dated Jul. 26, 2022, 16 pgs.
International Searching Authority, International Search Report and Written Opinion, issued in connection with International Application No. PCT/US2022/071175, dated Jul. 14, 2022, 10 pgs.
Ex Parte Quayle Action, U.S. Appl. No. 18/368,442, dated Nov. 30, 2023, 11 pgs.
Final Office Action, U.S. Appl. No. 17/911,374, dated Jan. 9, 2024, 21 pgs.
JP Decision to Grant, JP2023-557073, dated Feb. 1, 2024, 3 pgs. (English machine translation).
Extended European Search Report, EP21768625.2, dated Mar. 21, 2024, 8 pgs.

(56) References Cited

OTHER PUBLICATIONS

Notice of Allowance, U.S. Appl. No. 18/368,442, dated Feb. 16, 2024, 25 pgs.

* cited by examiner

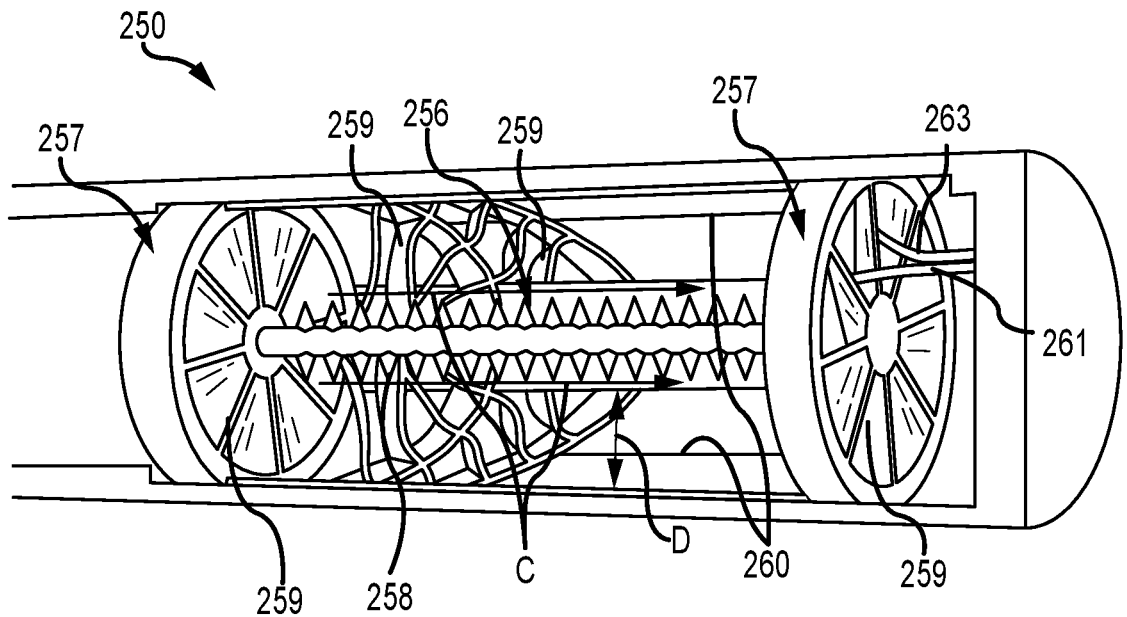
FIG.9B
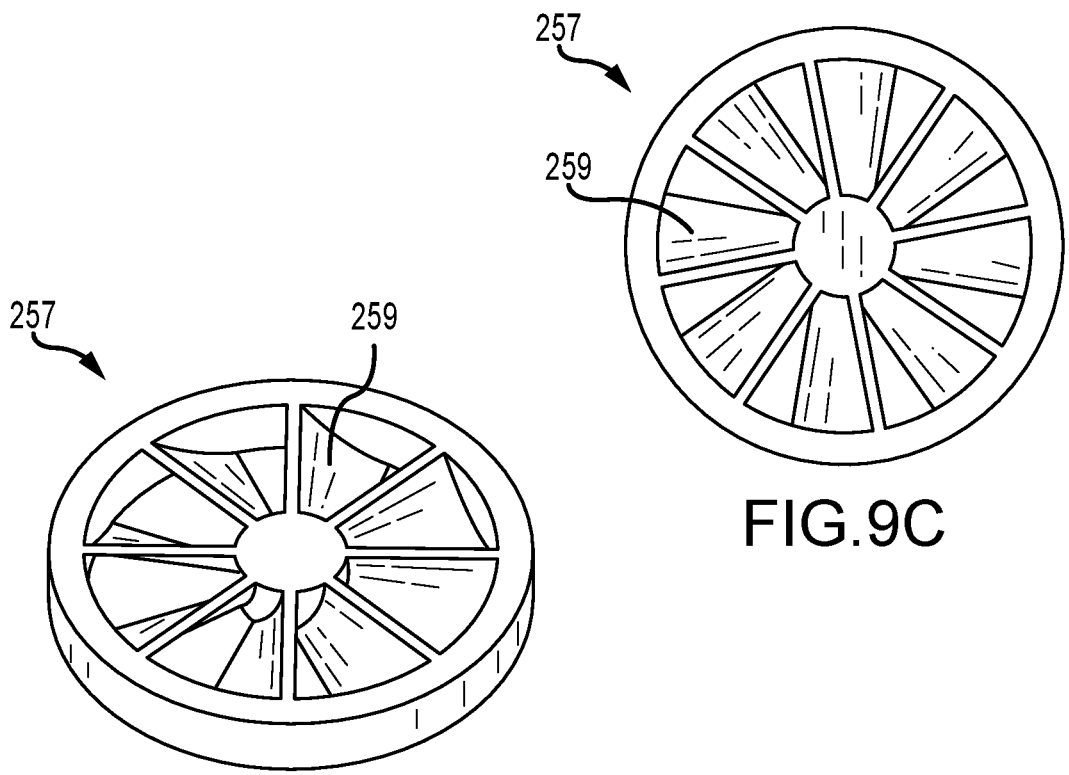
FIG.9C
FIG.9D

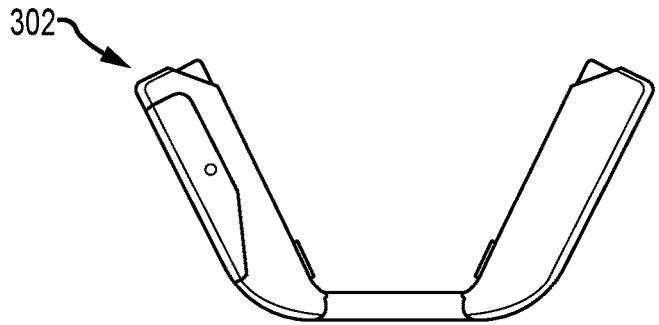
FIG.41C
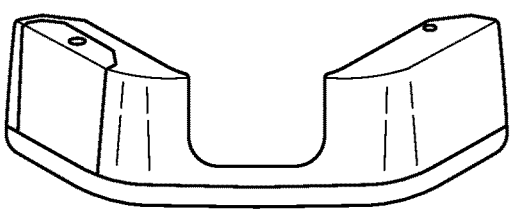
FIG.41D  FIG.41E  FIG.41F
FIG.41G
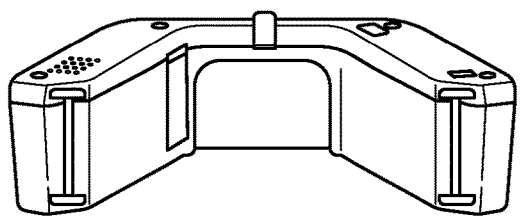
FIG.41H

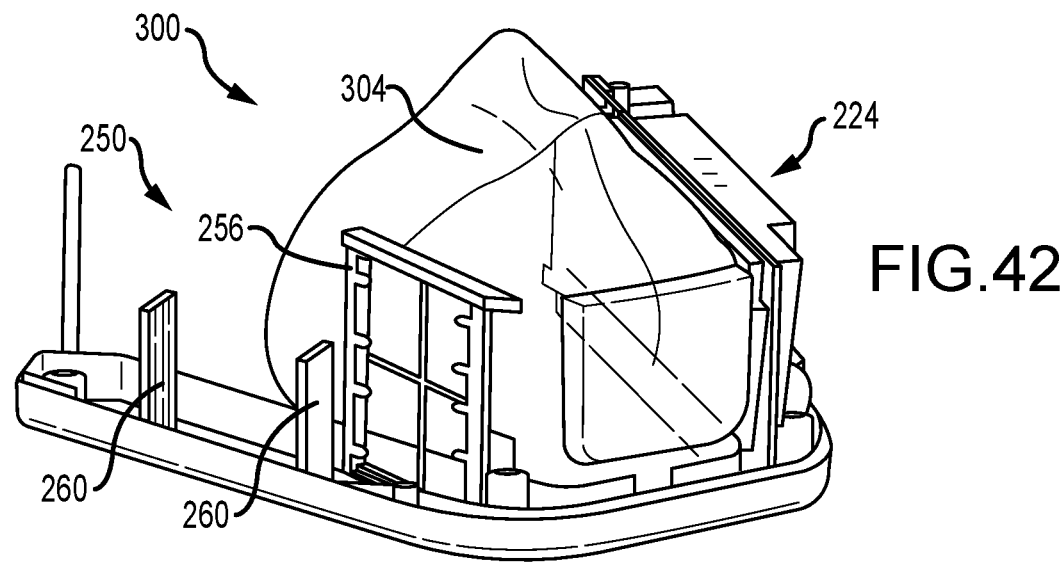
FIG. 42
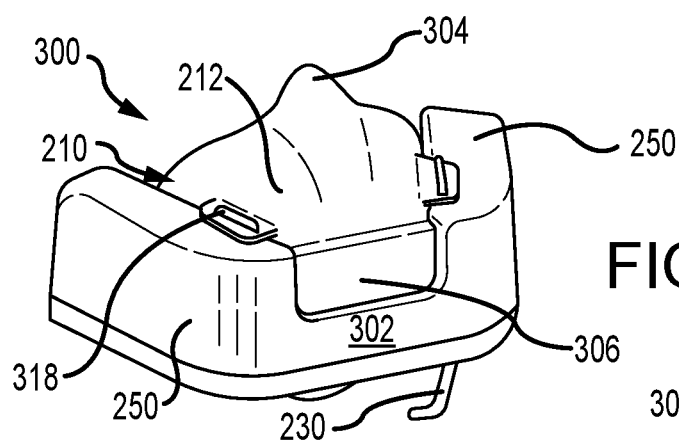
FIG. 43A
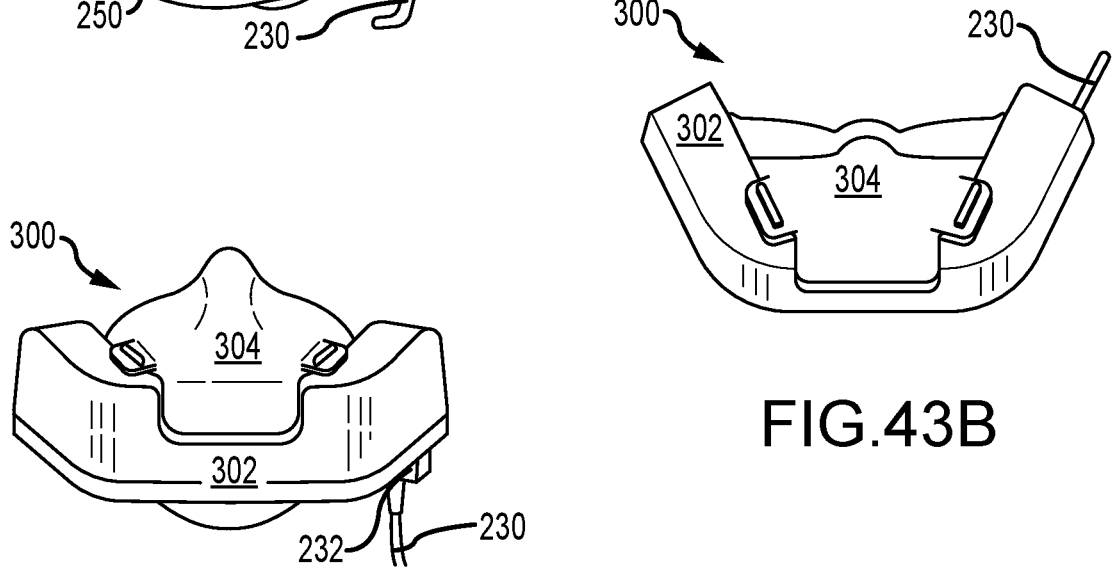
FIG. 43B
FIG. 43C

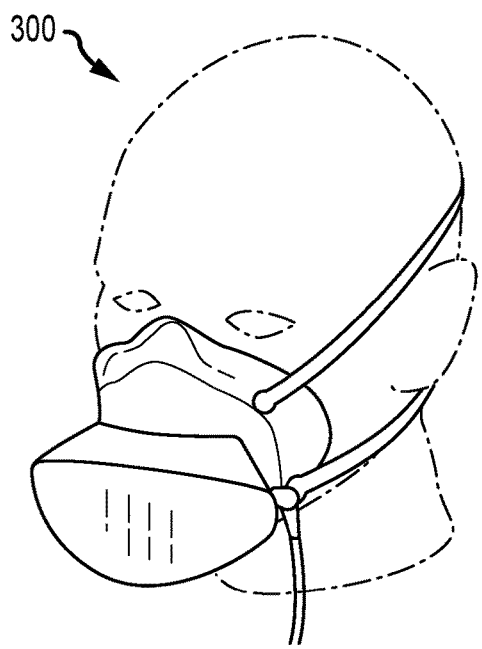
FIG.47A
FIG.47B
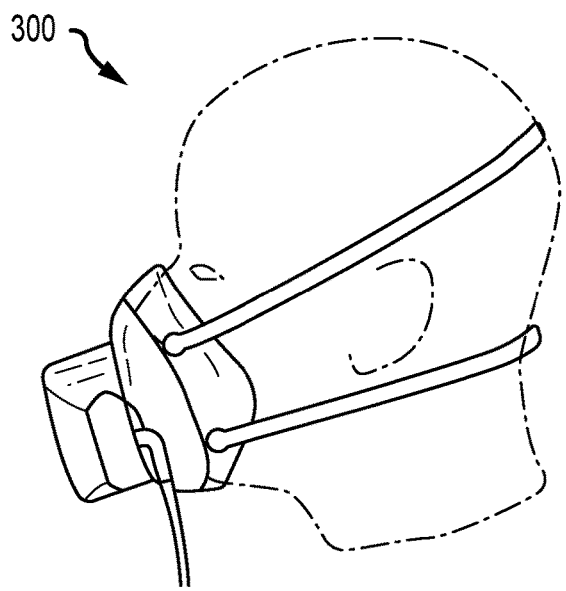
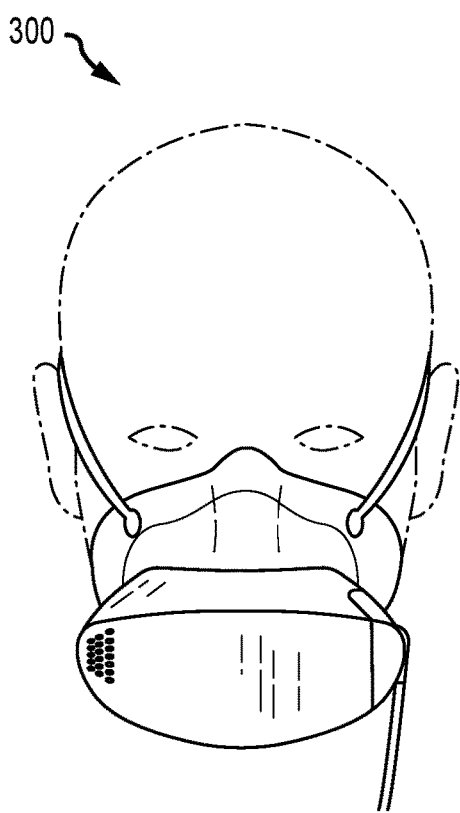
FIG.47C

ELECTRO-IONIC DEVICES FOR IMPROVED PROTECTION FROM AIRBORNE BIOPATHOGENS

CROSS REFERENCE TO RELATED APPLICATION

This application claims priority from Patent Cooperation Treaty (PCT) Patent Appln. No. PCT/US2021/022386 filed Mar. 15, 2021, which claims benefit of priority under 35 U.S.C. § 119 (e) from U.S. Provisional Patent Appln. No. 62/988,991 filed on Mar. 13, 2020, U.S. Provisional Patent Appln. No. 63/027,746 filed on May 20, 2020, U.S. Provisional Patent Appln. No. 63/043,424 filed on Jun. 24, 2020, U.S. Provisional Patent Appln. No. 63/044,768 filed on Jun. 26, 2020, U.S. Provisional Patent Appln. No. 63/063,968 filed on Aug. 11, 2020, and U.S. Provisional Patent Appln. No. 63/113,598 filed on Nov. 13, 2020, the entirety of each is incorporated by reference herein. This application also incorporates by reference in its entirety U.S. Pat. No. 6,901,930 filed on Oct. 28, 2002.

FIELD OF THE INVENTION

This application relates to devices and methods for improved protection from airborne biopathogens. In particular, this application relates to wearable devices and methods of using wearable devices for particle capture and deactivation.

BACKGROUND OF THE INVENTION

It is difficult for patients and practitioners to control the transmission of airborne viruses and infections. Examples of such infections include seasonal flu, common colds, and measles, among others. Recently, COVID-19 is thought to have a component of airborne transmission and cross infection. Some researchers believe that under normal circumstances, when small airborne particles enter the lungs, some of them may directly bypass the airway defensive system which is made up of mucous membranes in the nasal and oral cavity as well as the bronchial tree. These particles may enter the distal alveolus where they can rapidly begin contacting cells of the internal organ. Such penetration of the distal alveolus is thought to be confined to the smaller particles as the larger particles are trapped by the body's own filtration system.

Although the exact mechanism of viral transmission remains a point of controversy, some investigators lean towards the fact that viral transmission occurs through touching and then movement of the fingers to enter mucous membranes where the virus can implant itself. This theory is based on the idea that the human cough sprays larger droplets that can be effectively precipitated or filtered and do not necessarily need to be inhaled.

The exact mechanism of transmission remains controversial, but some investigators postulate that the small particles penetrating the distant alveolus is a significant modality of transmission. It is quite possible that the salivary droplets and mucous droplets that contain the virus and exit an infected patient as a cough mist partially evaporate or settle onto a surface. Such micro-droplets get smaller via evaporation and may become airborne again in the proximity of the enclosed space or circulating air system such as in buildings and airplanes.

The airborne transmissibility is predicated on the functional viability of the virus outside of the body in the air, in buildings, or airplane ventilators. If a viral particle remains viable outside of the body for a period of time, it is likely to be present as a small airborne particle that infects the body via distal alveolus and that bypass the oral and nasal mucous membranes that through evolution have developed defense mechanisms against serendipitous infection.

Just like in small particle drug delivery systems, the distal alveolus remains the undefended portal to the blood stream. The same aspect of airborne COVID-19 and the fact that it has extended functional survivability outside of the body in air and surfaces raises another important limitation of existing filtration technology like the N95 mask. This limitation exists because a filter entrapment of viral particles within the mask can potentially make the mask a secondary reservoir of live virus particles near the airway, and changes in evaporative status can seed the trapped viruses back into the respiratory system. It is desirable for a mask capable of adequate entrapment of viral particles and droplets to have a virus kill technology in real-time, not via occasional and inconsistent mask cleaning protocols.

SUMMARY OF THE INVENTION

In a first exemplary embodiment of an electro-ionic device configured for being worn on the face of a person may include at least two electrical conductors spaced apart from each other defining at least a portion of a respiratory pathway therebetween and a circuit configured to apply a first voltage between the two conductors during inspiration and a second voltage greater than the first voltage during expiration.

In some versions of the first exemplary embodiment, the circuit may be configured to generate ozone during expiration and during inspiration with the amount of ozone generated during inspiration being less than the amount of ozone being generated during expiration. Also, the electro-ionic device may include at least one sensor, and the circuit may be configured to detect inspiration and expiration based on the at least one sensor. The electro-ionic device may also include a fibrous filter positioned at least partially within the respiration pathway. Also, the first voltage may be greater than 100 volts. The electro-ionic device may also include a portable DC power supply.

In a second exemplary embodiment of the present invention, an electro-ionic device configured for being worn on the face of a person may include an electrically insulating material having a continuous surface defining an opening, the opening configured to surround a respiration pathway, at least two electrical conductors spaced apart from each other, at least one of the electrical conductors positioned within the respiration pathway, and a circuit configured to apply a voltage between the two conductors during at least inspiration.

In some versions of the second exemplary embodiment, the circuit may be configured to generate ozone during expiration and during inspiration with the amount of ozone generated during inspiration being less than the amount of ozone being generated during expiration. Also, the electro-ionic device may include at least one sensor, and the circuit may be configured to detect inspiration and expiration based on the at least one sensor. The electro-ionic device may also include a fibrous filter positioned at least partially within the respiration pathway. Also, the first voltage may be greater than 100 volts. The electro-ionic device may also include a portable DC power supply.

In a third exemplary embodiment of the present invention, a battery-powered electrostatic filter configured for being worn on the face of a person may include an electrically insulating material having a continuous surface defining an opening, the opening configured to surround a respiration pathway, at least two electrical conductors spaced apart from each other, at least one of the electrical conductors positioned within the respiration pathway, and a circuit configured to apply a first voltage between the two conductors during inspiration and a second voltage greater than the first voltage during expiration.

In some versions of the third exemplary embodiment, the circuit may be configured to generate ozone during expiration and during inspiration with the amount of ozone generated during inspiration being less than the amount of ozone being generated during expiration. Also, the electro-ionic device may include at least one sensor, and the circuit may be configured to detect inspiration and expiration based on the at least one sensor. The electro-ionic device may also include a fibrous filter positioned at least partially within the respiration pathway. Also, the first voltage may be greater than 100 volts. The electro-ionic device may also include a portable DC power supply.

For any of the first, second and third embodiments, the device may also include flow control vanes that result in at least one of spiral airflow, increased turbulence, or increased dwell time of airflow between the at least two electrical conductors.

For any of the first, second and third embodiments, the at least two conductors may include an emitter and a collector, the collector being radially outward from the emitter.

For any of the first, second and third embodiments, the at least two conductors may include an emitter and a collector, the collector radially extending about emitter. In doing so, the collector may define a radially outer circumferential boundary of at least a portion of the respiratory pathway.

For any of the first, second and third embodiments, the airflow through the portion of the respiratory pathway between the at least two conductors may be at least substantially parallel to the at least two conductors.

For any of the first, second and third embodiments, the airflow through the portion of the respiratory pathway between the at least two conductors may be at least substantially parallel to a longitudinal axis of each of the at least two conductors.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 9B is a perspective view of the version of the ionization filter of FIG. 9A employing spiraled spacers.

FIG. 9C is a front view of a spiraled spacer employed in the ionization filter of FIG. 9B.

FIG. 9D is an isometric view of the spiraled spacer of FIG. 9C.

FIG. 41C is a top view of the housing from FIG. 41A.
FIG. 41D is a left-side view of the housing from FIG. 41A.

FIG. 41E is a top, front perspective view of the housing from FIG. 41A.

FIG. 41F is a right-side view of the housing from FIG. 41A.

FIG. 41G is a bottom view of the housing from FIG. 41A.

FIG. 41H is a bottom, back, perspective view of the housing from FIG. 41A.

FIG. 42 is a perspective view of the electro-ionic device from FIG. 39A showing some components thereof.

FIG. 43A is a perspective view of an electro-ionic device according to an exemplary embodiment of the present disclosure.

FIG. 43B is a top view of the electro-ionic device from FIG. 43A.

FIG. 43C is a front view of the electro-ionic device from FIG. 43A.

FIG. 47A is a perspective view of an electro-ionic device according to an exemplary embodiment of the present disclosure.

FIG. 47B is a side view of the electro-ionic device from FIG. 47A.

FIG. 47C is a front view of the electro-ionic device from FIG. 47A.

DETAILED DESCRIPTION

Figure 1:
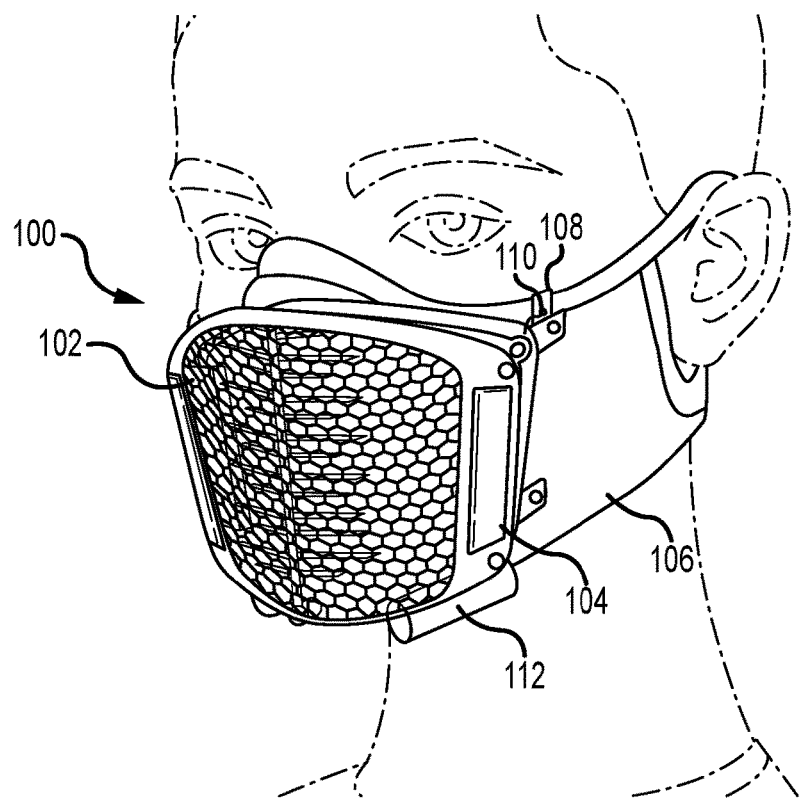
FIG. 1 is a perspective view of an electro-ionic device according to an exemplary embodiment of the present disclosure.
Figure 2:
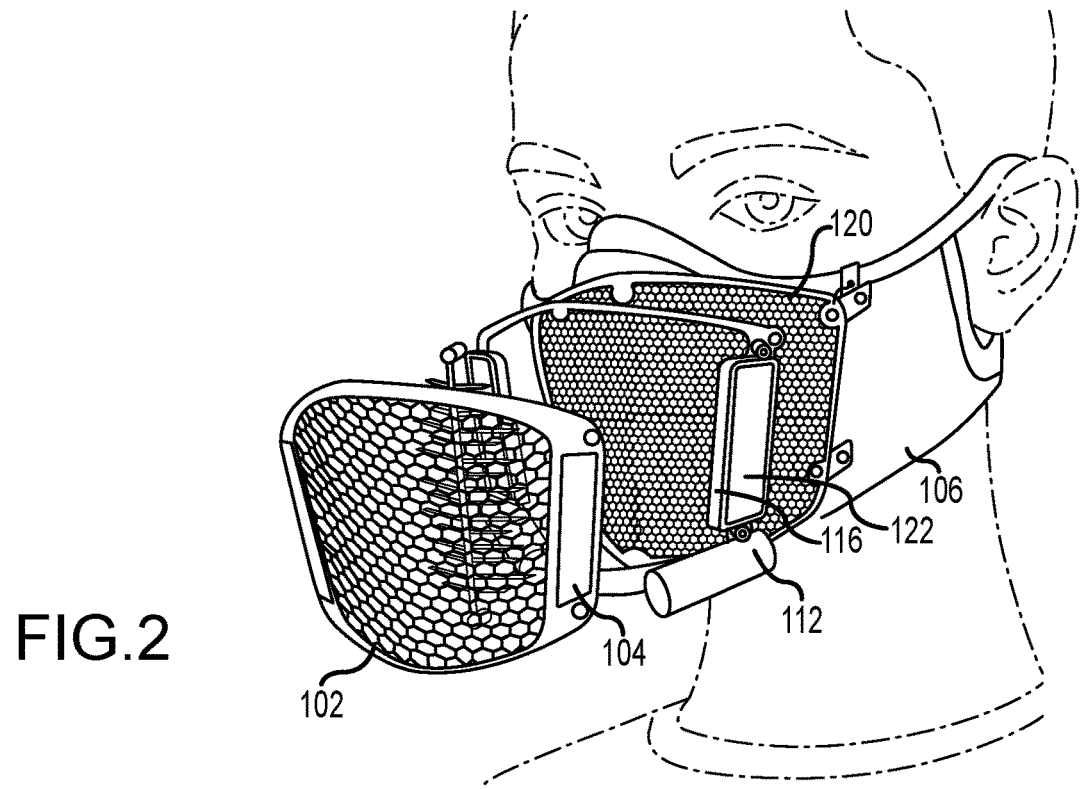
FIG. 2 is a perspective exploded view of the electro-ionic device from FIG. 1.
Figure 3:
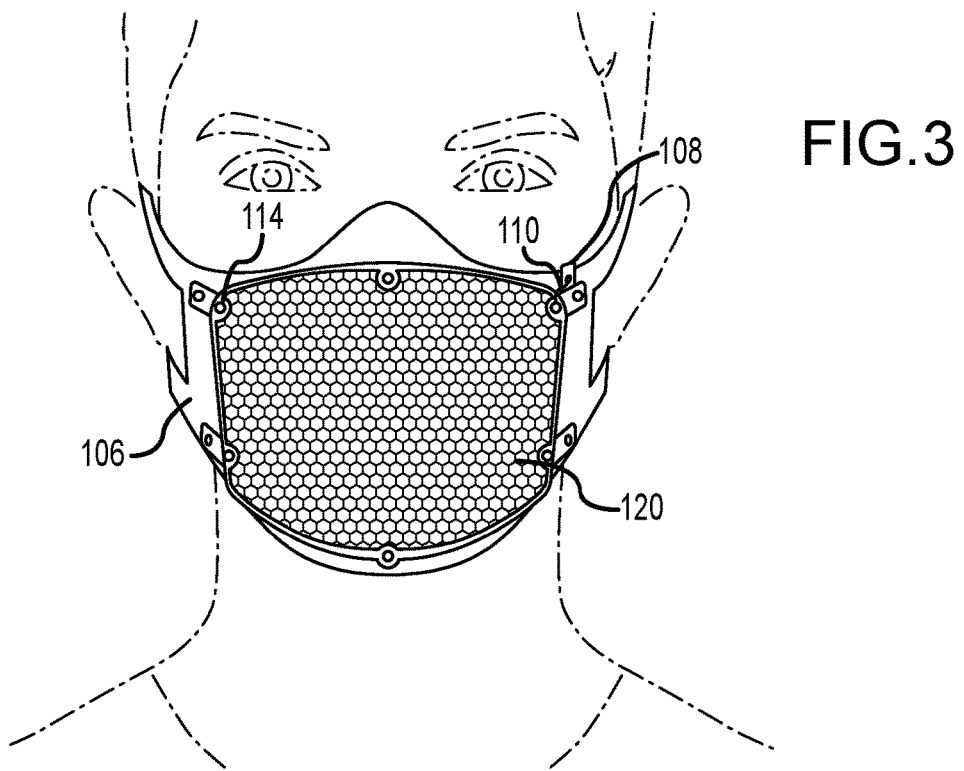
FIG. 3 is a front view the electro-ionic device from FIG. 1 showing some of the components thereof.
Figure 4:
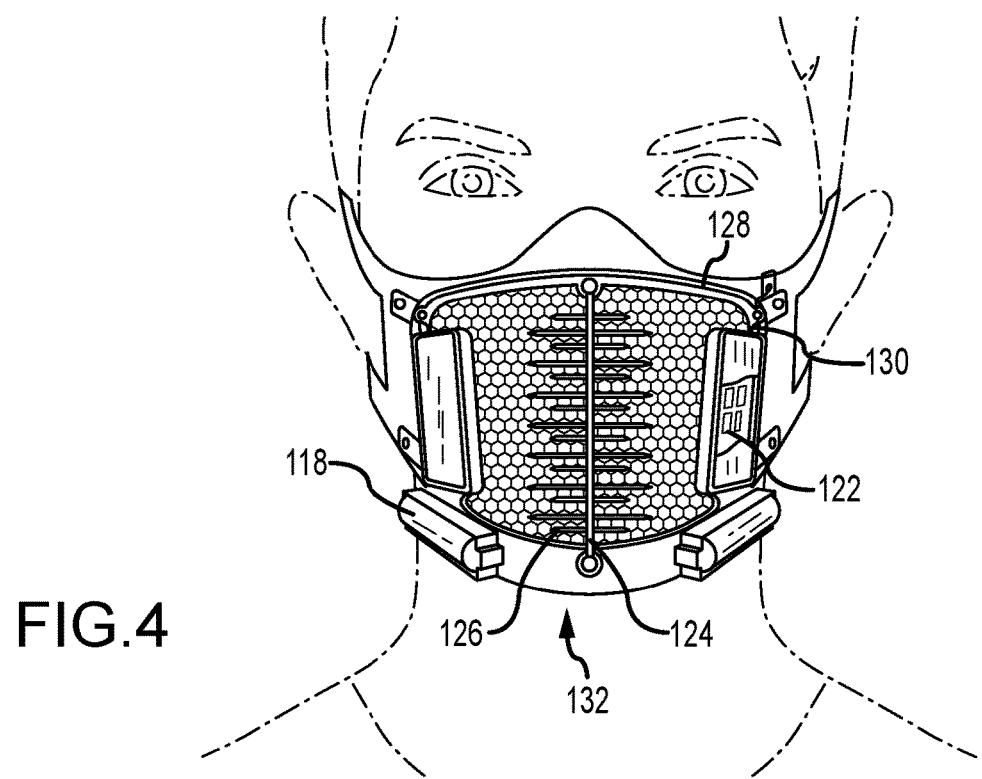
FIG. 4 is a front view the electro-ionic device from FIG. 1 showing some of the components thereof.
Figure 5:
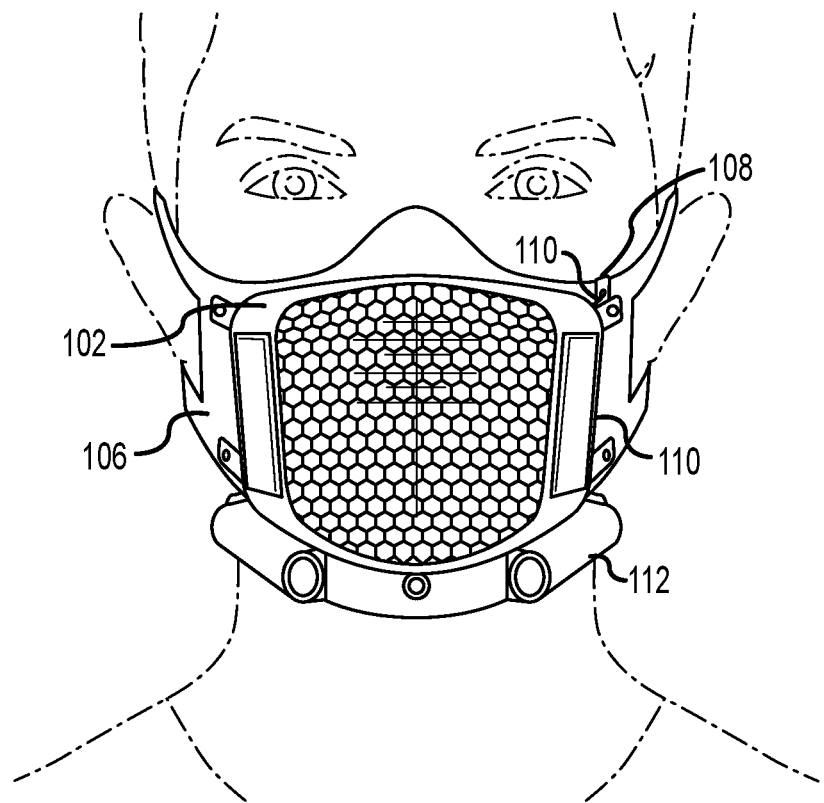
FIG. 5 is a front view the electro-ionic device from FIG. 1.

A portable and wearable electro-ionic device (e.g., electrostatic precipitator) is disclosed herein in a variety of embodiments and versions thereof. The portable and wearable electro-ionic device removes airborne particles from the air stream. For example, the electro-ionic device is configured to remove pathogens, toxins and other hazardous particles from an inspired air stream by virtue of electrostatic precipitation. Thus, in the age of COVID-19, the portable and wearable electro-ionic device and its electrostatic precipitation can remove from an inspired air stream droplets of saliva containing virus or virus particles that are airborne.

In some embodiments of the electro-ionic device described below, it will be understood that inspiration and/or expiration airflows within the electro-ionic device are substantially, if not completely, perpendicular to a strong electric field between an emitter and collector. Ideally, the emitter has sharp points to facilitate the rejection of electrons that in turn impart a charge onto airborne particles. As these charged airborne particles continue along their path within the electro-ionic device, the charged airborne particles are subjected to a strong electric field and thereby attracted to, and deposited on, the surface of the collector. The electric field between the emitter and the collector is generated from a battery supply and a step up voltage module. Subjecting the airflow to this strong electric field is the underlying modality that removes the particles in real time from the air stream.

The electro-ionic devices disclosed herein have sufficient electrical power storage and performance set points so that each charge can maintain performance efficacy for at least 8 to 12 hours. The electro-ionic devices are configured to be sufficiently lightweight such that they can be worn for extended periods of time attached to the face without creating irritation or fatigue.

The electro-ionic devices employ servo control of the power utilization to maintain both a proper performance window in terms of particle removal as well as assures proper current utilization and duration of wearable power supply. The servo control adjusts the voltage and current use in real time on a continuous basis during operation to achieve these aims. In other words, a servo mechanism is used to control the power that flows between the emitter and collector of the ionization filter.

In the various embodiments, the circuitry of the electro-ionic device monitors the supply current and auto-adjusts the voltage to maintain a fixed parameter such that the voltage across the emitter will be at an optimal level to filter without excessive ozone levels. In some embodiments, the same effect can be obtained by setting the voltage as a function of elevation pressure.

The distance and geometry of the air path is a balance for at least some of the embodiments of the electro-ionic device disclosed herein. For example, as a consideration, as the airflow passage geometry is increasingly extended to result in a longer and more effective airflow path, the resulting greater surface of the collector would require lower power usage but increase the weight and size of the ionizer filter, plus increase the snorkel effect and dead space that would contribute to carbon dioxide retention.

As another consideration, increasingly reducing the gap between emitter and collector and creating a narrower airflow path could lower the necessary operational voltage, but increase airflow resistance, increase the weight of the material of the device, increase the potential for ion flow tunneling and sparking, and create manufacturing difficulties. By balancing these concerns, in some versions of the embodiments disclosed herein, the operational voltage for the ionizer filter will be between approximately 5 kV and approximately 15 kV, and preferably 6 kV to 11.5 kV for a distance between the tip of the emitter and collector of 15 mm, at sea level. For other embodiments, with a distance between the tip of the emitter and collector between approximately 10 mm and approximately 20 mm, the operational voltage for the ionizer filter will be between approximately 4 kV and approximately 20 kV, at sea level.

The embodiments of the electro-ionic disclosed herein are efficient high-performance protective devices that are portable, comfortable and light enough for extended periods of time and capable of remaining operational for at least 8 to 12 hours on a single charge. Further, these embodiments offer an acceptable appearance plus a hydration port. Additionally, the configuration and visual transparency of the electro-ionic devices facilitate communication and even enhance communication by virtue of placement and amplification via Bluetooth microphone, which may be located within the mask of the electro-ionic device and, in some versions, in a plug of the hydration port. The numerous embodiments of the electro-ionic device illustrated in the above listed Figures make clear the features and capabilities of the electro-ionic device can come in a variety of configurations to facilitate wear ability, comfort and mitigate restrictions to movement or work performance. Finally, the electro-ionic device works, having been tested at the Tulane BSLIII lab to demonstrate a 99.8% viral penetration reduction in the context of a COVID-19 aerosol study with COVID-19 aerosol concentrations at much higher levels than would ever be encountered in real life.

For a detailed discussion of the various embodiments disclosed herein, reference will now be made to the exemplary embodiments, which are illustrated in the accompanying drawings. Wherever possible, the same reference numbers will be used throughout the drawings to refer to the same or like parts.

An exemplary embodiment of an electro-ionic device 100 is shown in FIGS. 1-5. The device 100 may include a base layer or a filtrate layer 106 at an innermost position toward a user. The filtrate layer 106 may be comprised of a fibrous or porous medium such as cotton, polypropylene, nylon, polyester, wool, rayon, or combinations thereof. The filtrate layer 106 may include attachments such as strings or loops to fasten to a user's ears or to tie behind the user's head.

A finely-meshed negative grid 120 may be positioned outward from the filtrate layer 106 and, as will be discussed in more detail below, may function to help repel negatively charged particles. The negative grid 120 may be comprised of an electrical conductor such as stainless steel, or alloys containing nickel, chromium, manganese, or combinations thereof. In addition, the negative grid 120 may be comprised of various metal foils and/or coated with one of the previously mentioned alloys. The negative grid 120 may be attached to the filtrate layer 106 with one or more tabs 114, such as four tabs 114. The tabs 114 may be comprised of the same material as the filtrate layer 106 and may hold the negative grid 120 closely thereto or the tabs 114 may function as standoffs having a rigid or semi-rigid construction providing a space between these layers. The negative grid 120 may be in electrical communication with a user contacting conductor 108 positioned on the filtrate layer 106 through a conductive wire 110. The user contacting conductor 108 may have a conductive surface on the inside of the filtrate layer 106 for contacting the user's skin, and may include an adhesive for better adhesion thereto. As shown, the user contacting conductor 108 is an annular surface surrounding an outer reinforced portion of a loop of the filtrate layer 106. However, in other embodiments not shown, the contacting conductor 108 may be positioned around the ear loops or nose bridge or in several portions along the filtrate layer 106 or entirely along an outer perimeter of the filtrate layer 106. The filtrate layer 106 itself may be infused with electrically conductive materials including conductive wires.

A component layer 132 may be positioned outward from the negative grid 120. The component layer 132 includes a frame 128 which may be comprised of an insulating material and directly mounted to the negative grid 120 or spaced slightly apart using separate or built-in standoffs. The frame 128 may have a continuous outer surface defining an opening radially inward and may be configured to surround a respiration pathway such that all or most of the inspired and expired air in the respiration pathway flows through the opening. The frame 128 may house one or more electronics compartments 122, such as two electronics compartments positioned diametrically across from each other outside of a mouth-covering portion of the electro-ionic device 100, one or more battery compartments 112 positioned below the mouth-covering portion, and an emitter 124 positioned directly in front of the mouth-covering portion directly in a respiration pathway of a user. The tabs 114, frame 128, and other standoffs may keep the emitter 124 at least 0.5 mm, 1.0 mm, or 2.0 mm from the user's face. Each electronics compartment 122 may include one or more circuits and may further include a processor or controller. Each of the electronics compartments 122 may have a metallic housing with a collector plate 116 such as an outwardly facing conductive side which faces toward the emitter 124. In other embodiments the collector plate 116 may be separate from the electronics compartment 122. The collector plate 116 may be placed outside of the opening in the frame.

The emitter 124 may comprise a plurality of electrodes 126 that are oriented perpendicular to the respiration pathway. Each of the electrodes 126 may be oriented parallel with respect to one another. The electrodes 126 may be machined or laser cut and form multiple sharp stainless steel or other oxidation resistant conductive materials oriented toward the collector plates 116. In some embodiments, the emitter 124 may comprise steel wool having multiple sharp thin pointed endings. In some embodiments, the emitter 124 may comprise carbon nanotubes. A process of nanotube deposition upon a conductive steel grid or wire in presence of high voltage gradient may orient them in a substantially vertical fashion with suitable separations or spacing therebetween. Once the nanotubes have bonded to the surface of the underlying conducting wire or a wire grid, the emitter 124 may have improved performance at significant manufacturing savings as compared to building sharp points via machining or laser cutting production. Further, the tips of the electrodes 126 may have a metal coating to help decrease the electron workforce and improve the efficiency of electro-ionic device 100. Such coatings may include manganese, iridium, tantalum, and zinc, among others. Reducing the electron workforce may permit a reduction in the emitter voltage and thereby improve the viability of the underlying power source as well as the underlying components.

The battery compartments 112 may include one or more batteries 118. As shown, the electro-ionic device 100 includes two battery compartments 112 each housing a battery 118. The batteries 118 may include, for example, AA alkaline batteries, AAA alkaline batteries, or other alkaline batteries of various sizes. The batteries 118 may also include, for example, rechargeable batteries including NiCD, NiMH, or lithium ion, such as a set of 18650 lithium batteries. It may also be possible to replace the batteries 118 without need for removing the electro-ionic device 100 from the face of a user. The electro-ionic device 100 may be worn for extended period of time during work day and travel. As such, it may include batteries 118 having a functional capacity of at least 8 hours. The batteries may be operatively connected to the electronics compartment 122 to provide electrical power to various circuits. During use, these circuits may consume less than 1 watt at 24 volts, preferably they may consume 0.2 watt at 24 volts. One such circuit may include a battery monitoring circuit which may alert a user with either an audio, a visual, or a tactile alert when the batteries 118 become low.

The electronics compartment 122 may be operatively connected to a switch (not shown) for turning on and off the electro-ionic device 100. The electronics compartment 122 may also be connected to the emitter 124 via a conductive wire 130 routed under behind the frame 128, the negative grid 120, an acceleration grid 102, and one or more collector plates 116 which are operatively described in more detail below. The acceleration grid 102 and the collector plates 116 may be located in an outer layer farther outward with respect to the component layer 132. The acceleration grid 102 has substantially the same outer shape as the negative grid 120 and the frame 128, and similarly is positioned within the respiration pathway of a user. However, in other embodiments the outer shapes of the three respective layers may vary and need not be identical. The acceleration grid 102 includes a mesh of electrical conductors forming pores or holes each having a diameter greater than the pores or holes of the negative grid 120. However, in other embodiments, the pores of the acceleration grid 102 are the same as or smaller than the pores of the negative grid 120. The collector plates 116 may be positioned around the edges of the frame, such as the sides of the frame so as to not interfere with the breathing. As shown, the collector plates 116 are positioned in front of the electronics compartment 122 to optimize the cross-sectional surface area of the porous layers in front of the respiration pathway while minimizing the overall size of the electro-ionic device 100. The collector plates 116 may include a hydrogel 104 having virucidal oxidizing agents such as, sodium hypochlorite, hydrogen peroxide, sodium percarbonate, sodium perborate, or benzalkonium chloride, embedded therein to help ensure that any virus or bacteria collected is killed. In the embodiment shown, the emitter 124 is positioned behind the collector plates 116, but in other embodiments, the emitter 124 may be positioned in front of the collector plates 116 or both in front of and behind the collector plates 116.

The electronics compartment 122 may include a high voltage circuit, such as a Cockcroft-Walton generator, for generating a high voltage output. During operation, the high voltage circuit in the electronics compartment 122 can apply a voltage potential between the emitter 124 and the collector plates 116 greater than 100 V, preferably between 500 V and 20 kV with the emitter 124 being negatively charged and the collector plates 116 being positively charged and creating an electrostatic precipitator. In some embodiments, the voltage applied may be between 1 kV and 14 kV and preferably between 2 kV and 12 kV. When the emitter 124 is charged with respect to the collector plates 116, electrons build up on the electrodes 126 at their respective tips. Depending on a number of factors, some electrons are transmitted across the gap between the emitter 124 and the collector plates 116. Preferentially, electrons attach to small airborne particles in the gap imparting a negative charge thereto. These charged particles can be precipitated out and/or attracted to the nearby positively charged collector plates 116 creating an inertial diversion. In addition, the acceleration grid 102 may also be positively charged with respect to the emitter 124. Due to this charge, negatively charged particles may be attracted to the acceleration grid 102 and it may assist in creating an ionic movement away from the user's face. The charge of the acceleration grid 102 may be the same as the collector plates 116 or the charge may be less positive so as to continue to attract the particles away from the face and toward the collector plates 116 after contacting the acceleration grid 102.

In addition to the emitter 124, the negative grid 120 may also be negatively charged. The negative grid 120 may have the same charge as the emitter 124 or its charge may be lower. The negative grid 120 may serve to repel negative charges from entering the airway. The user contacting conductor 108 may also impart a negative charge onto the user's body, in particular, onto tissue near the mask, such as openings to the mouth and nostrils, to further repel the negatively charged particles from settling onto the surface of the user's body. The negative grid 120 may attract and neutralize positively charged particles generated by the emitter 124 as a byproduct of ionization of the air, such as ozone.

As mentioned above, ozone may be produced as a byproduct of the ionization of the air. Ozone itself is an oxidizing agent and is effective in killing viruses and bacteria. However, ozone is also an irritant to the lungs. Therefore, circuitry in the electronics compartment 122 may control the amount of ozone generated. For example, the voltage potential between the emitter 124 and collector plates 116 may be optimized to generate safe levels of ozone to assist in killing viruses. For example, the emitter 124 may generate less than 0.1 ppm of inhaled air. The emitter 124 may preferably generate less than 0.05 ppm. The electro-ionic device 100 may incorporate sensors (not shown) for detecting and measuring inspiration and expiration. For example, the electro-ionic device 100 may incorporate a thermistor and/or pressure sensor or strain gage. These sensors may communicate with a controlling circuit for controlling the voltage potential between the emitter 124 and the collector plates 116 to generate high levels of ozone during expiration and lower levels of ozone during inspiration. High levels of ozone during expiration may help kill any stored viruses attached to components of the electro-ionic device 100. The controlling circuit may oscillate the voltage between the emitter 124 and collector plates 116 between 1.2 kV and 12 kV, during inspiration and expiration respectively. More preferably, the controlling circuit may oscillate the voltage between the emitter 124 and collector plates 116 between 2.4 kV and 12 kV, during inspiration and expiration respectively. The voltage gradient may fundamentally be a DC bias voltage, but for improved function, an AC voltage component with a frequency between 50 Hz and 100 kHz may be superimposed onto the DC voltage. Returning to the negative grid 120, since it may be comprised of nickel, chromium, manganese, or alloys comprised of these metals such as a stainless steel alloy, the surface may oxidize and assist in the degradation of ozone to diatomic oxygen thus further reducing the concentration of breathable ozone.

The electro-ionic device 100 may also include a gasket (not shown) around the filtrate layer 106 to improve the fit and seal of the device to the skin. The gasket may be comprised of a silicone gel, hydrogel, or polyvinyl polymers among other polymeric or elastomeric materials. The thickness of the gasket may be between 0.5-6.0 mm, preferably 1-4 mm and applied to both sides of the filtrate layer 106 or folded over onto both sides of the filtrate layer 106. In addition, the gasket may include tabs or protrusions to assist the user in removing from the face.

In one embodiment of the electro-ionic device 100, or any of the following embodiments discussed below, the electro-ionic device may also have a self-sealing port (not shown) for receiving a straw from a beverage to maintain hydration levels all day without removing the electro-ionic device from the user's face. In another embodiment, the self-sealing port may instead be a plug port having a plug portion attached via a tether to a port portion such that the plug portion can be withdrawn from the port portion to allow a drinking straw to be passed through the port portion. Once the straw is withdrawn from the port portion, the plug portion can again be inserted into the port portion to seal the port portion. In some instances, the plug portion may be a blue tooth equipped microphone, which when placed in the port portion, can receive and broadcast the voice of the person wearing the electro-ionic device.

Figure 6:
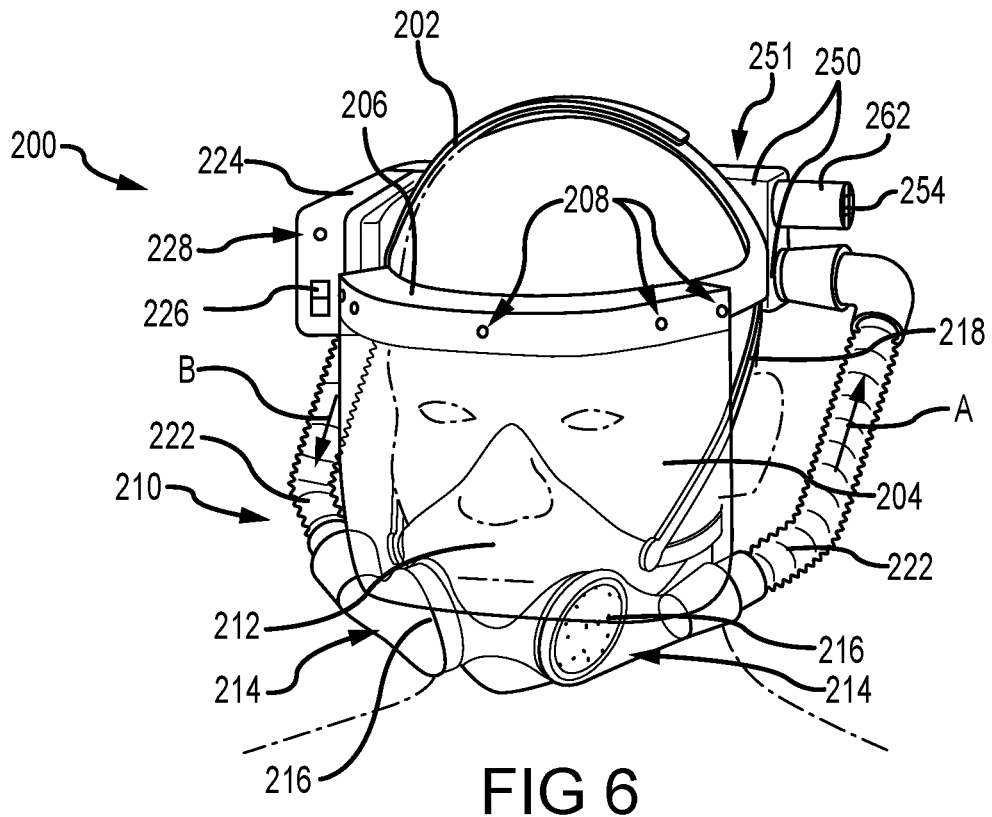
FIG. 6 is a perspective view of an electro-ionic device according to an exemplary embodiment of the present disclosure.

Another exemplary embodiment of an electro-ionic device 200 is shown in FIG. 6. The electro-ionic device 200 may include similar or the same components as the electro-ionic device 100. Wherever possible, the same reference numbers will be used for brevity.

The electro-ionic device 200 may include an adjustable headband 202 for attaching itself to the head and supporting various components of the electro-ionic device 200. A transparent face shield 204 may be mounted onto a face shield spacer 206 positioned at the front of the headband 202 to position the face shield 204 substantially concentrically outward from the headband 202 and outward from the face to at least provide clearance for a mask subassembly 210. The face shield spacer 206 may be comprised of a semi-rigid material, such as a closed cell foam or an elastomer, to allow it to conform to the shape of a user's forehead. The face shield spacer 206 may include a number of mounting tabs 208 for reversibly mounting the face shield 204 thereto. The face shield 204 may be comprised of a plastic, such as polycarbonate and may be configured to be replaced via the mounting tabs 208.

Figure 27:
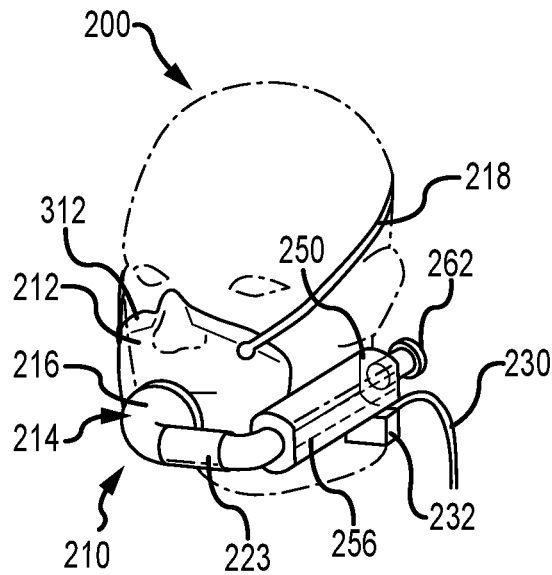
FIG. 27 is a perspective view of an electro-ionic device according to an exemplary embodiment of the present disclosure.
Figure 28:
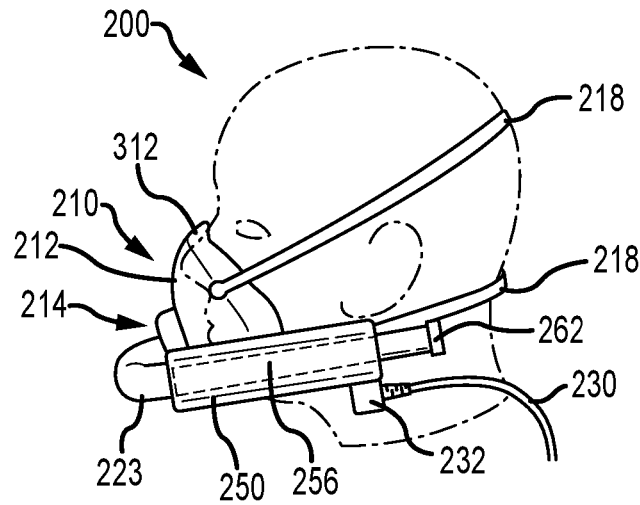
FIG. 28 is a side view of the electro-ionic device of FIG. 27.
Figure 29:
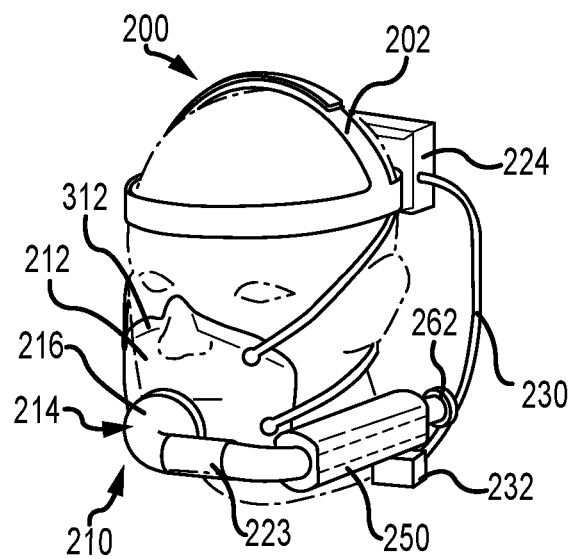
FIG. 29 is a perspective view of an electro-ionic device according to an exemplary embodiment of the present disclosure.
Figure 30:
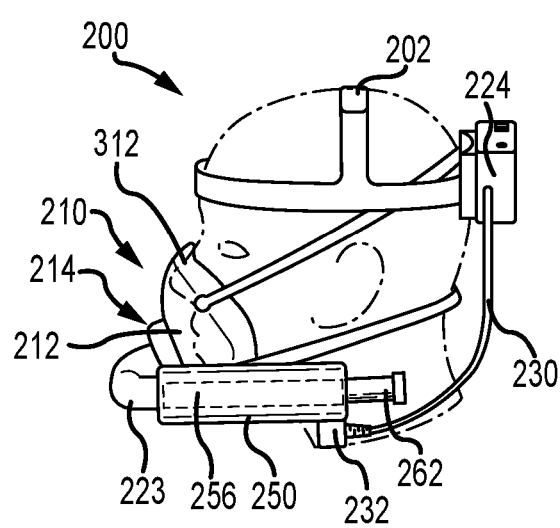
FIG. 30 is a side view of the electro-ionic device of FIG. 27.

The mask subassembly 210 may include a mask 212 comprised of a transparent soft plastic, such as a silicone or polyvinyl. The mask 212 may have one or more openings 214 for inspiration and/or expiration. In the embodiment shown in FIG. 6, the mask 212 includes two openings 214 away from the face when worn properly as shown in FIG. 6, but in other embodiments (shown and described below, e.g., with respect to FIGS. 26-30), the mask 212 may include a single opening. Each of the openings 214 may be separately dedicated for only inspiration or expiration or they may both be configured for both inspiration and expiration. Each of the openings 214 may have a filtrate layer 216 substantially the same as filtrate layer 106 discussed above, other than its size. The mask subassembly 210 may include straps 218 for attaching the mask subassembly 210 to a user's head. The straps 218 may be elastic and flexible. In some embodiments, such as the electro-ionic device 200 shown in FIG. 6, the straps 218 may connect to or be integrated with the headband 202. In other embodiments, such as embodiments without a headband 202 (shown and described below, e.g., FIGS. 27 and 28), the straps 218 may engage directly with the user's head.

The electro-ionic device 200 may also include a gasket (not shown in FIG. 6, but see gasket 312 in FIGS. 27-30, for example) around the mask 212 to improve the fit and seal of the device to the skin. The gasket 312 may be comprised of a silicone gel, hydrogel, or polyvinyl polymers among other polymeric or elastomeric materials. The thickness of the gasket may be between 0.5-6.0 mm, preferably 1-4 mm and extend along the face-contacting border of the mask 212, as can be understood from FIGS. 27-30. The gasket may include tabs or protrusions to assist the user in removing from the face. As already discussed above, the electro-ionic device 200 may also have a self-sealing port or other type of port for receiving a straw from a beverage to maintain hydration levels all day without removing the electro-ionic device 200.

Figure 10:
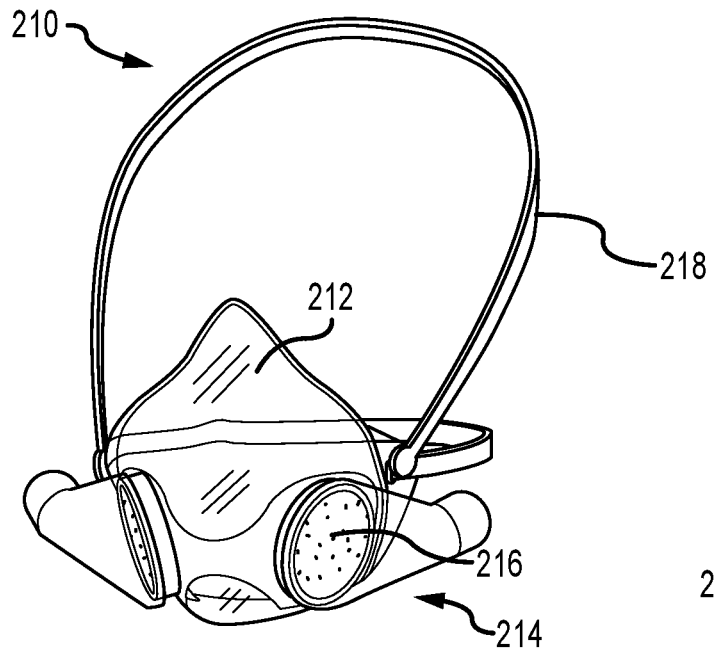
FIG. 10 is a perspective view of a mask filter according to an exemplary embodiment of the present disclosure.
Figure 11:
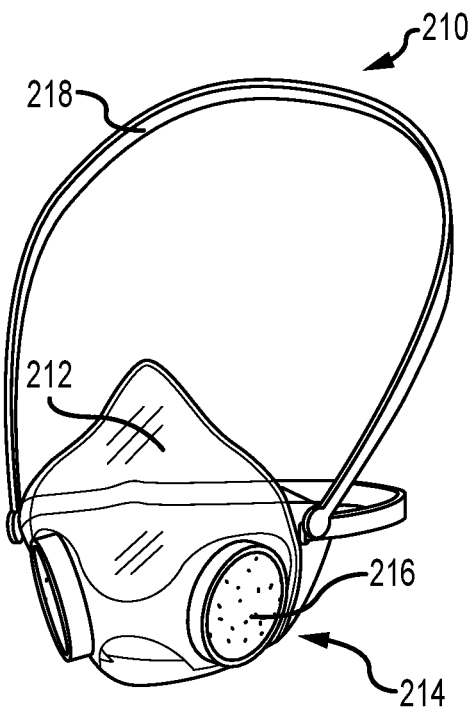
FIG. 11 is a perspective view of the mask filter from FIG. 10 showing some of the components thereof.
Figure 12:
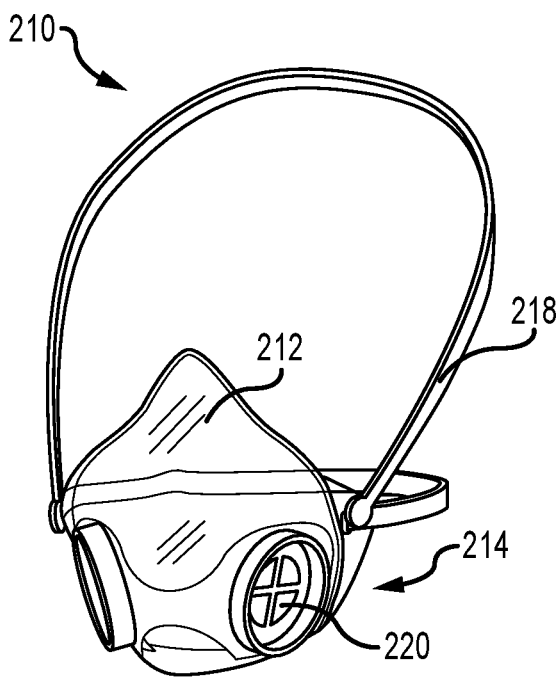
FIG. 12 is a perspective view of the mask filter from FIG. 10 showing some of the components thereof.

FIGS. 10-12 show the mask 212 with bidirectional valve controlled airflow that mitigates snorkel dead space. More specifically, and as shown in FIG. 12, the openings 214 may also include a one-way valve 220 such as rubber diaphragm or a check-valve. The valves 220 may be configured to permit one of the openings 214 to be used for inspiration only and the other opening 214 for expiration only.

Referring again to FIG. 6, each of the openings 214 may have flexible tubing 222 connected thereto and extend to an ionization filter 250 defining a fluid passageway or conduit therebetween. The flexible tubing 222 may include various adapters and tubing segments, in addition, the tubing 222 may have corrugations 223 to provide improved flexibility and may have an interior diameter of 12-25 mm, preferably 15 mm.

In some embodiments, as shown in FIGS. 26-30, in addition to employing flexible tubing, which may be smooth 222 or corrugated 223, the fluid passageway or conduit may be modular such that segments of the tubing may be arranged male-female to allow for adjustment of length of a section of tubing between the openings 214 and the ionization filter 250 or other components of the electro-ionic device 200. Such an adjustable modular arrangement allows for adjustment to accommodate differently sized user heads.

In some embodiments where the device 200 employs a single airflow conduit for both inhalation and exhalation, or where multiple airflow conduits are employed for both inhalation and exhalation, the adjustable modular arrangement of the device 200 allows the volume of the electro-ionic device 200 to have its total volume adjusted (i.e., the combined volume of the mask 212, volume of tubing(s) 222, 223, and volume of ionizer chamber(s) 250) to an optimal volume for the user so as to avoid snorkel effect issues (e.g., rebreathing and failure of air adequate air exchange). In one embodiment, the device 200 will have an adjustable total volume ranging between approximately 80 ml and approximately 100 ml. In some embodiments, the device 200 will not be adjustable with respect to its total volume and will simply be available at different incremental sizes such as extra-small, small, medium, large and extra-large for different size user heads and offering different total volumes ranging between 80 ml and 100 ml (for example, 80 ml, 85 ml, 90 ml, 95 ml and 100 ml for sizes extra-small, small, medium, large and extra-large, respectively).

The headband 202 may also support an electronics unit 224 and the ionization filter 250. The electronics unit 224 may include a power supply and electronic circuitry the same as or similar to the batteries 118 and the circuitry within the electronics compartment 122 as discussed above with regard to the electro-ionic device 100. In addition, the electronics unit 224 may include a power switch 226 and indicator light 228.

Figure 7:
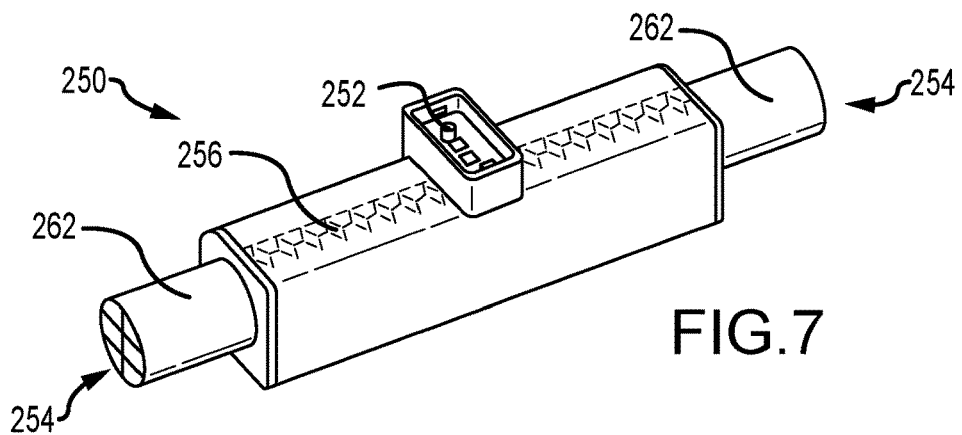
FIG. 7 is a perspective view of an ionization filter according to an exemplary embodiment of the present disclosure.
Figure 8:
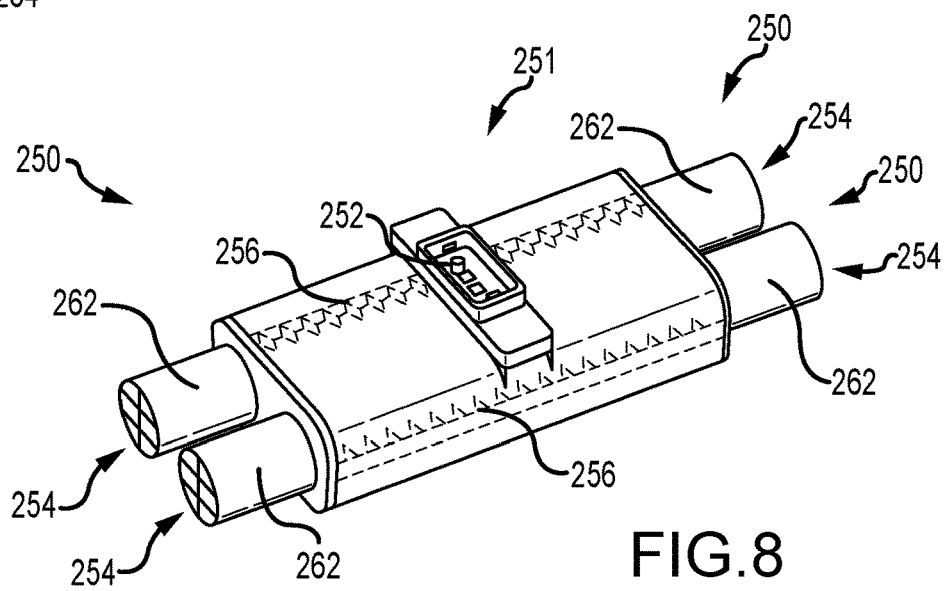
FIG. 8 is a perspective view of an ionization filter from FIG. 6.
Figure 14:
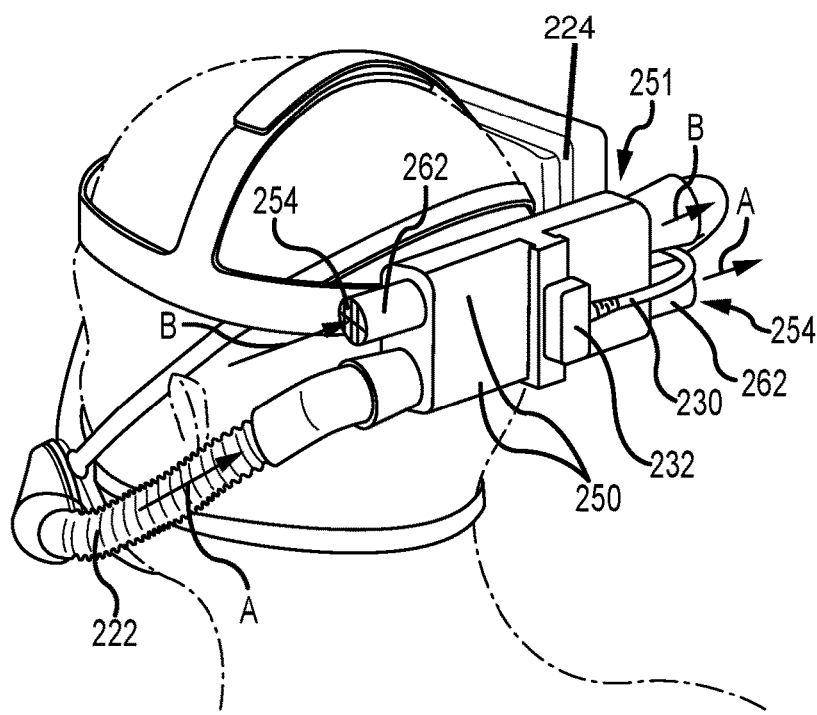
FIG. 14 is a back perspective view of the electro-ionic device from FIG. 13.

As shown in FIGS. 7, 8, and 14, the electronics unit 224 may be connected to the ionization filter 250 via a cable 230. In particular, an end of the cable 230 may contain a male connector 232 which interfaces with a female connector 252 formed in the ionization filter 250. The cable 230 may include two conductors (not shown) to provide low voltage power to the male connector 232. The male connector 232 may include high voltage circuitry, such as a Cockroft-Walton generator to convert the low voltage power to a high voltage supply to the ionization filter 250. In other embodiments, the ionization filter 250 may include the high voltage circuitry to convert the low voltage power inside the ionization filter 250. In yet other embodiments, the electronics unit 224 may include the high voltage circuitry and the cable 230 may provide the high voltage power to the ionization filter 250. The male connector 232 may also include a spring loaded resistor (not shown), such as between 100 ohms and 10,000 ohms, configured to intermittently contact conductor pads on the female connector 252 during disengagement with or unplugging of the male connector 232 to safely dissipate any residual high voltage in the ionization filter 250 and to limit current flow to the ionization filter 250 during an initial charging when the male connector 232 is initially plugged into the female connector 252. The cable 230 may also include a pin loop connector (not shown) for removing the voltage supplied by the electronics unit 224 upon disconnection of male connector 232 from the ionizer filter 250.

Figure 9A:
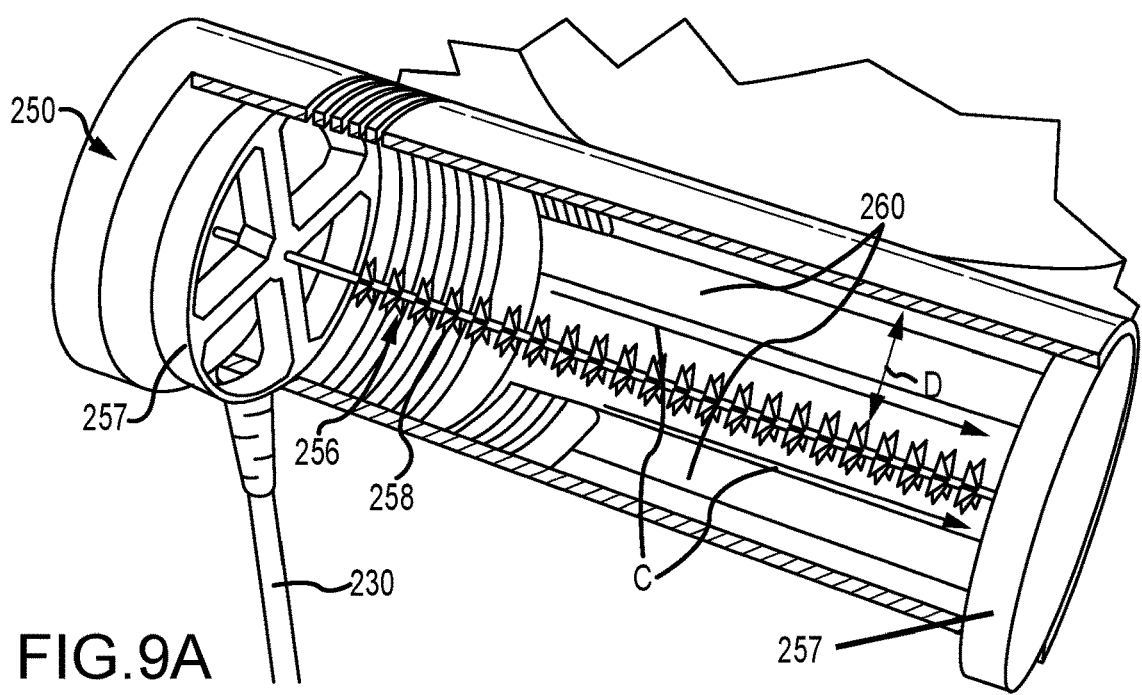
FIG. 9A is a perspective view of an ionization filter according to an exemplary embodiment of the present disclosure.

FIGS. 7, 9A and 9B illustrate a single ionization filter 250 and FIG. 8 illustrates two ionization filters 250 joined together in the same housing to form a dual ionization filter assembly 251. The ionization filters 250 shown in FIGS. 7, 9A and 9B have slightly different geometry, but include substantially the same elements and function in the substantially same way. The ionization filter 250 may have a tube-shaped housing with openings 254 at opposed ends. Either one of the openings 254 can operate solely as an inlet, while the other opening 254 operates as an outlet, such as when the ionization filter 250 is configured for only one of inspiration or expiration. In some embodiments, both inspiration and expiration take place though a single ionization filter 250 and both openings can be both inlets and outlets. The housing may have a cylindrical or frustoconical extension 262 immediately adjacent the openings to allow the flexible tubing 222 to attach thereto.

As best shown in FIGS. 9A and 9B, an emitter 256 extends longitudinally along a central axis through an inside of the cavity of the ionization filter 250 and is held centered therein by spacers 257. In other embodiments not shown, the emitter 256 extends longitudinally along a wall of the housing. In addition, the emitter may be protected with a ceramic material or other shielding material having a high emissivity. The emitter 256 may function in substantially the same manner as emitter 124 discussed above. The emitter 256 may include a plurality of electrodes 258 extending radially outward from the emitter 256, comprising similar materials as discussed above with respect to the electro-ionic device 100. The electrodes 258 may be axially spaced apart from one another and have one or more of radially extending points at any particular axial position.

As shown in FIGS. 9A and 9B, the chamber of the ionization filter 250 may also include one or more collector plates 260. The collector plate(s) 260 may surround the emitter 256 along the inside of the housing and may have a substantially circular or rectangular cross-section along the axial length of the emitter 256. The collector plate 260 may be comprised of similar materials as the collector plates 116 as discussed above with respect to the electro-ionic device 100. The ionization filter 250 may be removed from the electro-ionic device 200 for cleaning. Cleaning the ionization filter may include washing with water or other solutions including detergents, solvents, and/or oxidizing agents.

Still referring to FIGS. 9A and 9B, as can be understood from the Arrows C, which represent the general direction of airflow through the cavity of the ionization filter 250, the airflow direction is substantially, if not completely, parallel to the surface of the collector 260 and longitudinal axis of the emitter 256. Also, the general direction of airflow through the cavity of the ionization filter 250 is substantially, if not completely, perpendicular to the radially outwardly projecting tips of the electrodes 258.

As indicated by Arrow D in FIGS. 9A and 9B, in some versions of the embodiments disclosed herein, the operational voltage for the ionizer filter will be between approximately 5 kV and approximately 15 kV, and preferably 6 kV to 11.5 kV for a distance (Arrow D) between the tip of the emitter and collector of 15 mm, at sea level. For other embodiments, with a distance (Arrow D) between the tip of the emitter and collector between approximately 10 mm and approximately 20 mm, the operational voltage for the ionizer filter will be between approximately 4 kV and approximately 20 kV, at sea level.

In some embodiments, the voltage and current are adjustable to fine tune the filtration of the ionization filter to the elevation and circumstances. Additionally, in some embodiments, the collector is mechanically and selectively positionable relative to the emitter such that a distance (Arrow D) between the collector and tip of the emitter can be set to accommodate the settings of the current and voltage to optimize filtration. Such an embodiment may be accomplished via a mechanical arrangement that causes the collector to radially increase or decrease its offset from the emitter it surrounds. Alternatively, the housing of the ionization filter may be configured to allow different collectors to be swapped out, the different collectors having different radii and therefore different offset distances (Arrow D) from the surrounded emitter.

As shown in FIG. 9A, the spacers 257 may have straight or non-spiral vanes or spokes such that they do not spiral the airflow along the chamber path between the emitter 256 and collector 260. However, as can be understood from FIGS. 9B, 9C and 9D, to help extend the effective length of the airflow within the chamber to achieve greater dwell time of the airflow and its particles within the chamber of the ionization chamber 250 to afford an increased chance that the particles will be pulled from the airflow and attached to the collector 260, the spacers 257 may have spiral vanes 259 that spiral the airflow, or at least cause turbulence of the airflow. Such a spiral airflow facilitating arrangement allows the chamber of the ionization filter 250 to have a shorter longitudinal length, size and weight than would otherwise be possible. As can be seen in FIG. 9B, the spiral vanes 259 may extend into chamber of the ionization chamber 250 in a series of stacked layers arrangements to increase the likelihood the airflow with spiral within the chamber.

As indicated in FIG. 9B, and as is the case with all the other embodiments of the ionization filter 250 disclosed herein, a conductor 261 will extend from the power source and electronics of the electronics unit 224 to the emitter, and another conductor 263 will extend from the battery and electronics of the electronics unit 224 to the emitter 260. These conductors are routed from the electronics unit 224 to the ionization filter 250 via the cable 230, as can be seen in FIG. 9A.

In some embodiments, the electro-ionic device 200 may have a preferred orientation such as one of the openings 254 to be oriented closer to the mask subassembly 210 than the other opening 254. In such embodiments, the extension 262 nearer to the mask assembly 210 may include a negative grid substantially similar in material and function as the negative grid 120 and the extension 262 farther to the mask assembly 210 may include an acceleration grid substantially similar in material and function as the acceleration grid 102.

Figure 13:
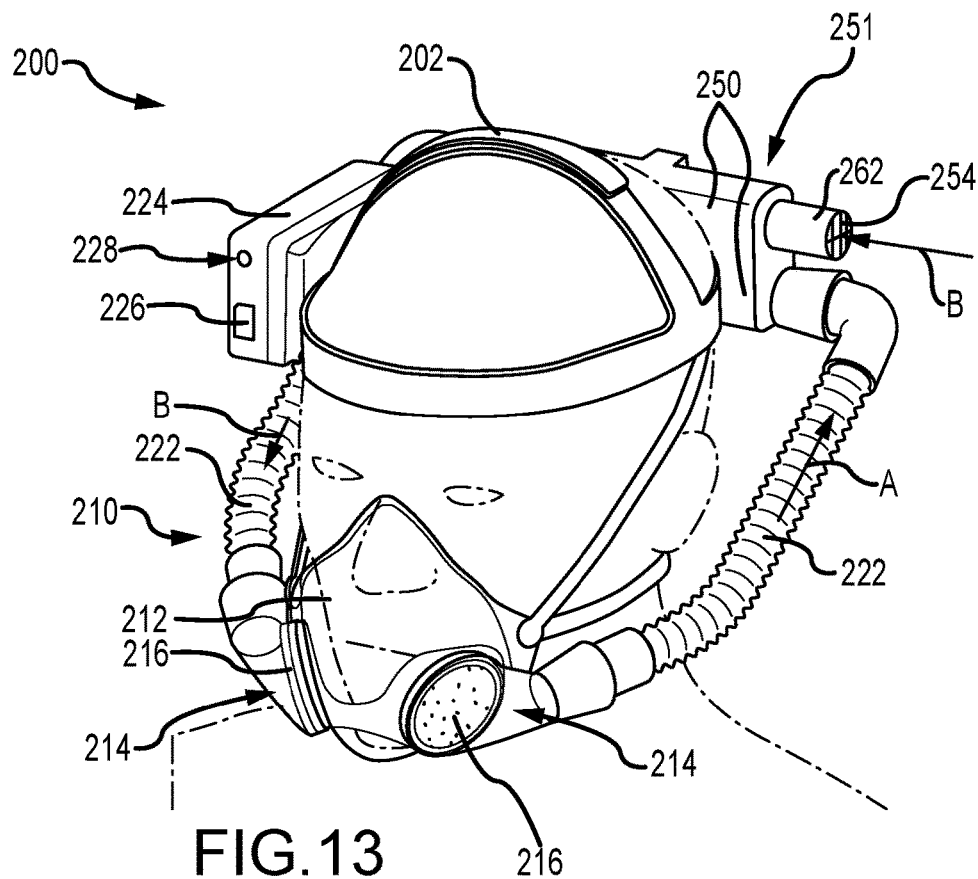
FIG. 13 is a front perspective view of an electro-ionic device according to an exemplary embodiment of the present disclosure.

In the embodiments shown in FIGS. 6, 13 and 14, which employ a dual ionization filter assembly 251, an exhalation pathway is called out via Arrow A and exists as a first pathway from mask 212, through a first one of the openings 214, through a first one of the flexible tubing 222, through a first one of the ionization filters 250, and then out a first one of the openings 254, this one-way airflow being facilitated via a first valve 220 (e.g., as shown in FIG. 12) for one-way air flow located in the first opening 214 underneath a first filtrate layer 216.

Still referring to FIGS. 6, 13 and 14, an inhalation pathway is called out via Arrow B and exists as a second pathway from a second one of the openings 254, through a second one of the ionization filters 250, through a second one of the flexible tubing 222, through a second one of the openings 214, and then into the mask 212, this one-way airflow being facilitated via a second valve 220 (e.g. as shown in FIG. 12) for one-way air flow located in the second opening underneath a second filtrate layer 216. In such a configuration air entering the second pathway may be filtered before it is inhaled and filtered after it is exhaled and passes through the first pathway. Because the air passing through the second pathway is configured to be inhaled, the amount of ozone generated in the second ionization filter 250 may be kept at safe level, such as 0.1 ppm or lower. On the other hand, because the air exiting the first ionization filter 250 is not configured to be directly inhaled, the amount of ozone generated may be higher than that of the second ionization filter 250.

In another configuration of the embodiments shown in FIGS. 6, 13 and 14, both of the openings 214 may be free of a valve 220, such that inspiration and expiration may take place in both the first and second pathways to reduce the total resistance to breathing through the electro-ionic device 200.

Figure 15:
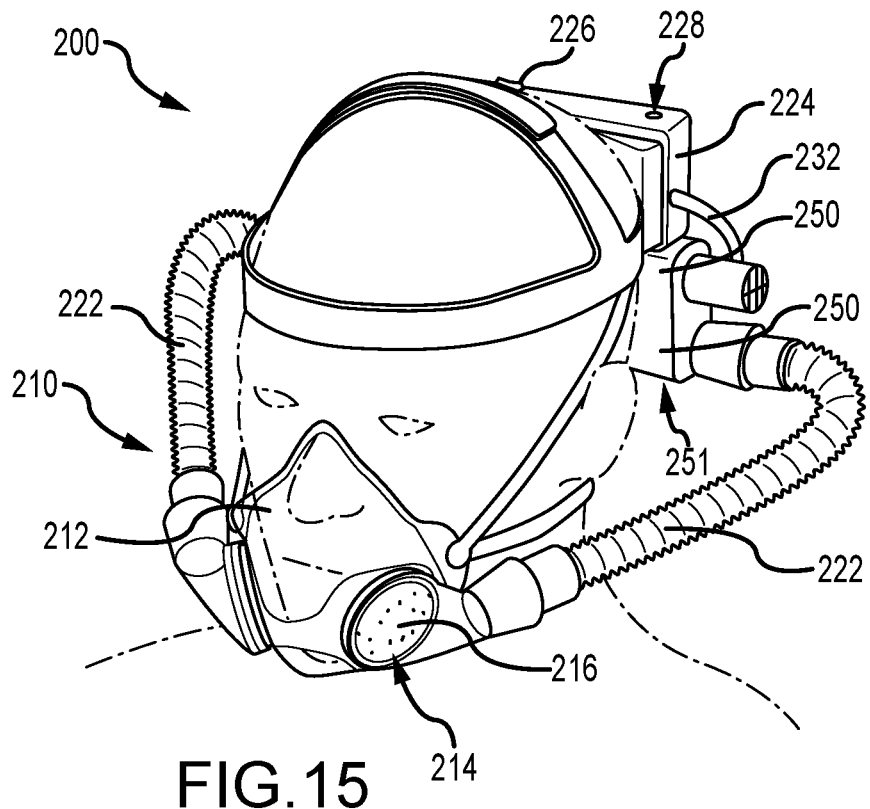
FIG. 15 is a front perspective view of an electro-ionic device according to an exemplary embodiment of the present disclosure.
Figure 16:
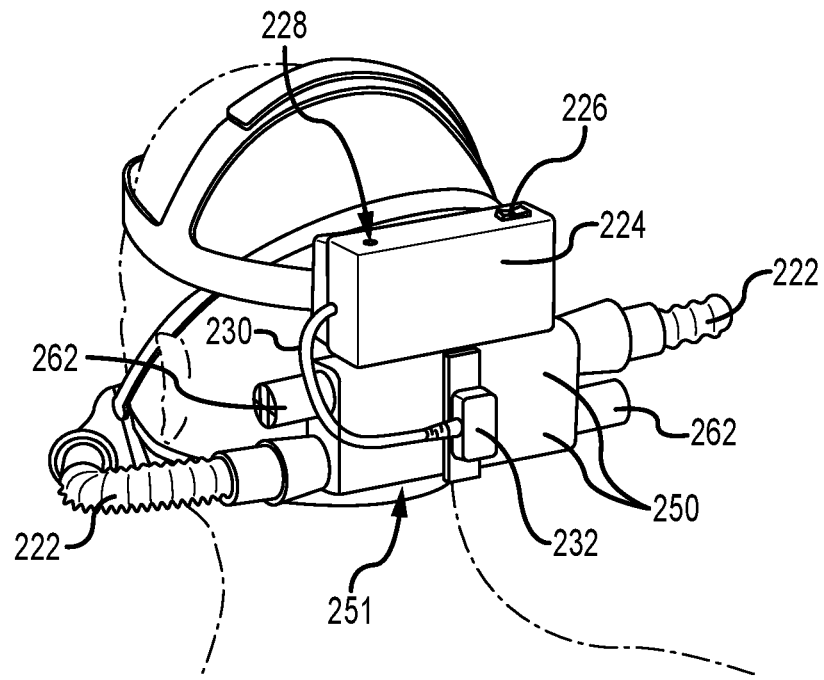
FIG. 16 is a back perspective view of the electro-ionic device from FIG. 15.

The electro-ionic device 200 may have modular components such that it may be configured in various different ways, including some of the modular embodiments discussed above, without departing from the scope of the invention. For example, FIGS. 13 and 14 show the electro-ionic device 200 similar to the embodiment shown in FIG. 6 but without the face shield 204. FIGS. 15 and 16 show the electro-ionic device 200 similar to the embodiment shown in FIG. 13 but with the electronics unit 224 mounted above and on top of the ionization filter 250.

Figure 17:
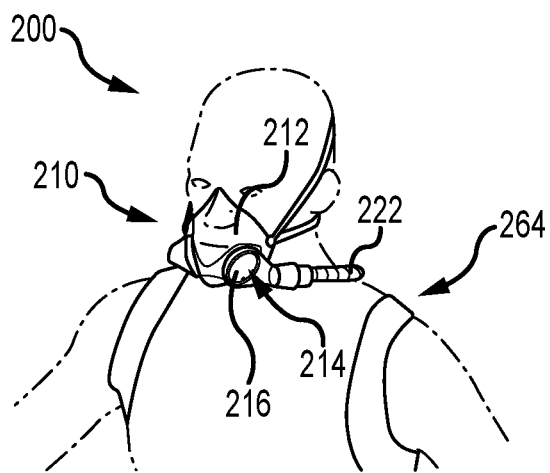
FIG. 17 is a front perspective view of an electro-ionic device according to an exemplary embodiment of the present disclosure.
Figure 18:
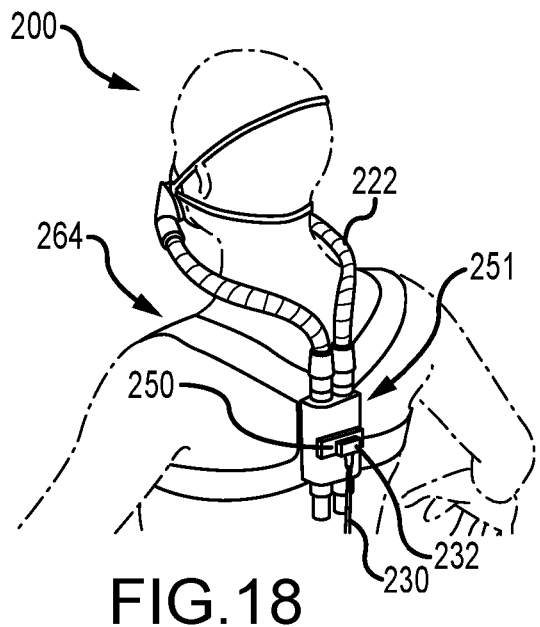
FIG. 18 is a back perspective view of the electro-ionic device from FIG. 17.
Figure 19:
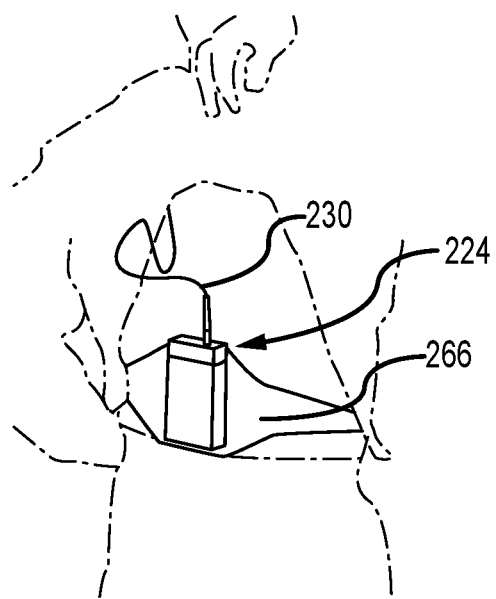
FIG. 19 is a perspective view of a power supply according to an exemplary embodiment of the present disclosure.

FIGS. 17 and 18 shows another embodiment of the electro-ionic device 200 similar to the embodiment shown in FIG. 6, having a shoulder strap 264 for supporting the dual ionization filter assembly 251 on the shoulder straps 264 on the user's back. The embodiment may also include a back strap 266 or other device such as a belt clip for securing the electronics unit 224, such as the back strap 266 shown in FIG. 19.

Figure 20:
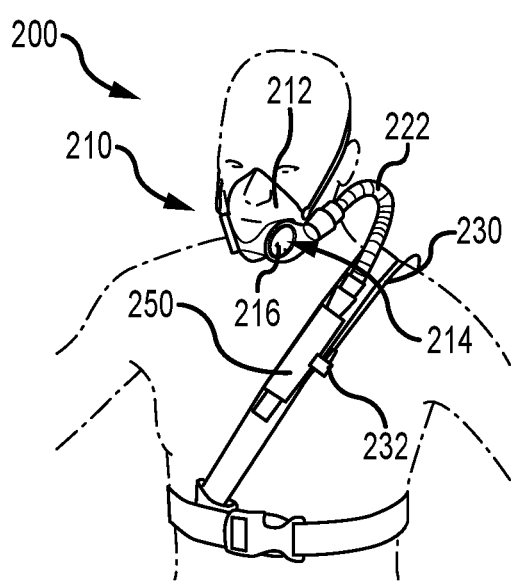
FIG. 20 is a perspective view of an electro-ionic device according to an exemplary embodiment of the present disclosure.
Figure 21:
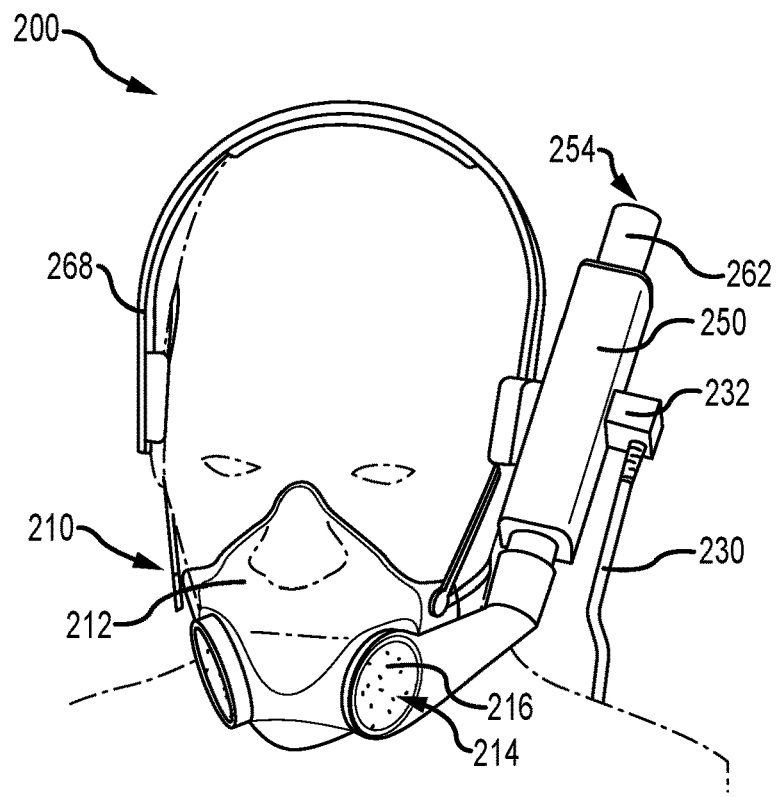
FIG. 21 is a perspective view of an electro-ionic device according to an exemplary embodiment of the present disclosure.

FIG. 20 shows a configuration of the electro-ionic device 200 where only a single ionization filter 250 may be attached to a shoulder strap 264 on the chest and an electronics unit 224 may be attached to a back strap on the back. With electro-ionic device 200 having a single ionization filter 250, the mask subassembly 210 may be configured with a valve 220 in a first opening 214 to permit inspiration through the ionization filter 250 and a valve 220 in the second opening 214 to permit direct expiration through the filtrate layer 216 directly to the environment.

In an alternate version of the embodiment of FIG. 20, the opening 214 may be free of a valve 220, such that inspiration and expiration may take place the pathway leading through the single ionization filter 250 such that exhaled air is treated via the single ionization filter 250.

As can be understood via a review and comparison of the embodiments depicted in FIGS. 13-20, these embodiments illustrate various body fitting arrangements addressing user comfort and wear ability. Also, the embodiments shown in FIGS. 13-20 are modular arrangements of the electro-ionic device 200 where the electronics unit 224 is separated from the ionization chamber(s) 250.

FIGS. 21-25 illustrate embodiments of the electro-ionic device 200 with a single opening 214 that is not occluded and available for both inspiration and expiration, the other opening 214 either being completely occluded or used as a filtered exhaust port. In reference to the embodiment of FIG. 21, it can be understood that this embodiment is also similar to the embodiment of FIG. 20, but instead of the single ionization filter 250 being supported by a shoulder strap, it is supported by a head set 268.

Figure 22:
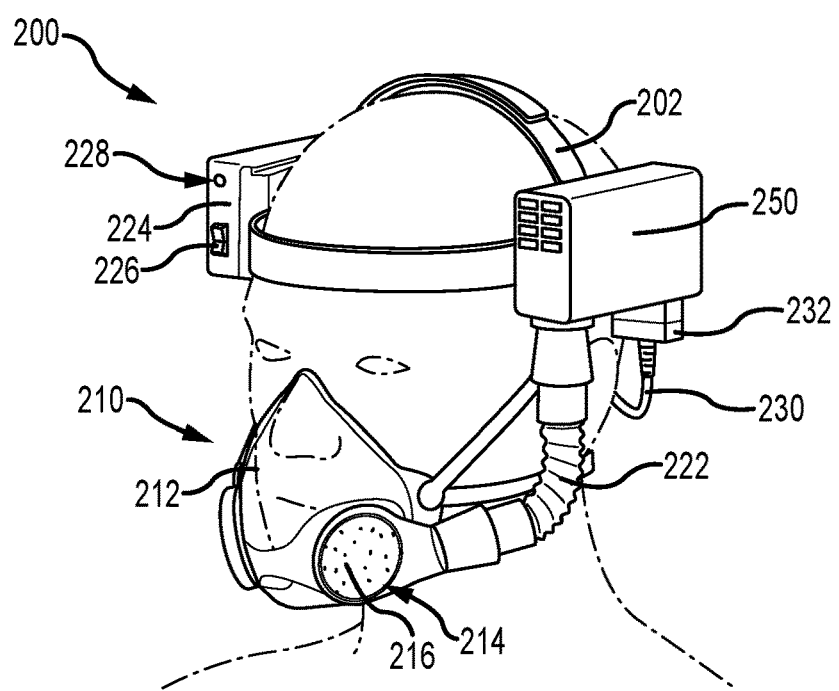
FIG. 22 is a perspective view of an electro-ionic device according to an exemplary embodiment of the present disclosure.
Figure 23:
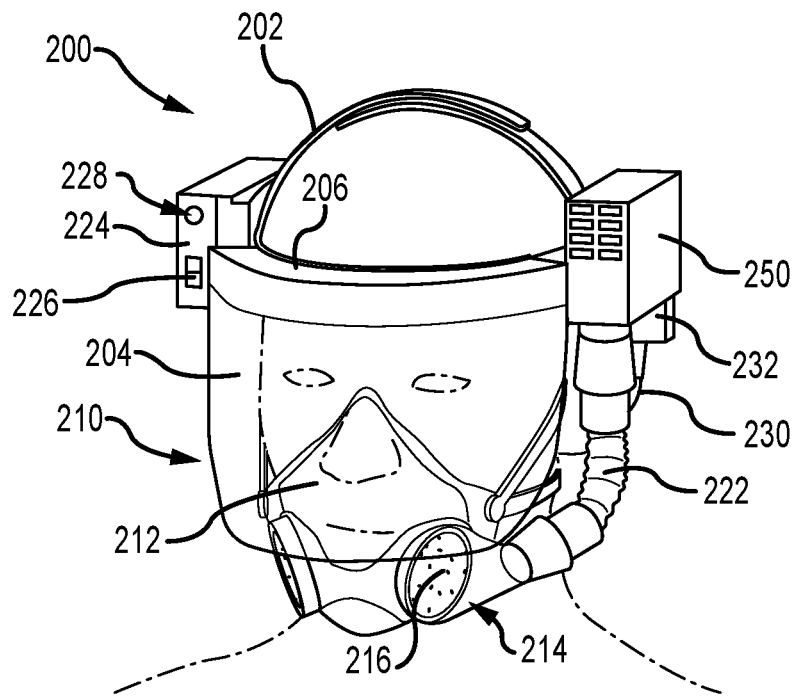
FIG. 23 is a perspective view of an electro-ionic device according to an exemplary embodiment of the present disclosure.

FIGS. 22 and 23 show another configuration of the electro-ionic device 220 in which a single ionization filter 250 is supported by the head band 202. In these embodiments, the ionization filter 250 may be shaped to have a similar size and/or weight as the electronics unit 224.

Figure 24:
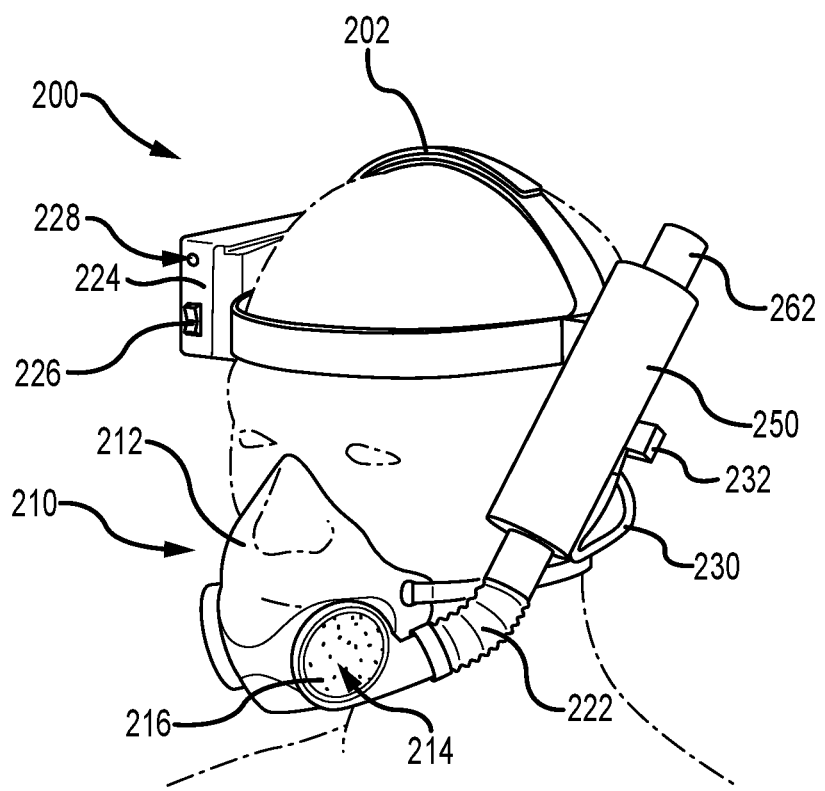
FIG. 24 is a perspective view of an electro-ionic device according to an exemplary embodiment of the present disclosure.
Figure 25:
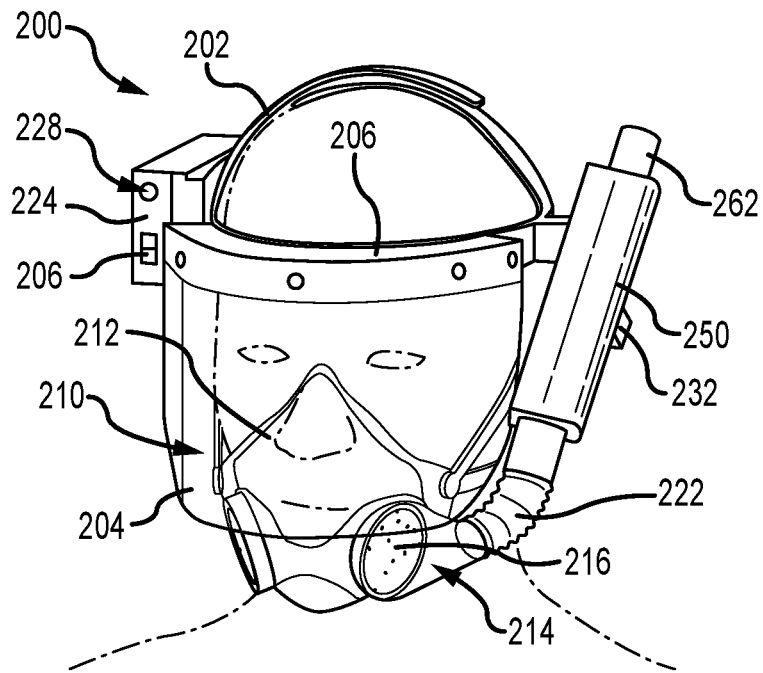
FIG. 25 is a perspective view of an electro-ionic device according to an exemplary embodiment of the present disclosure.
Figure 26:
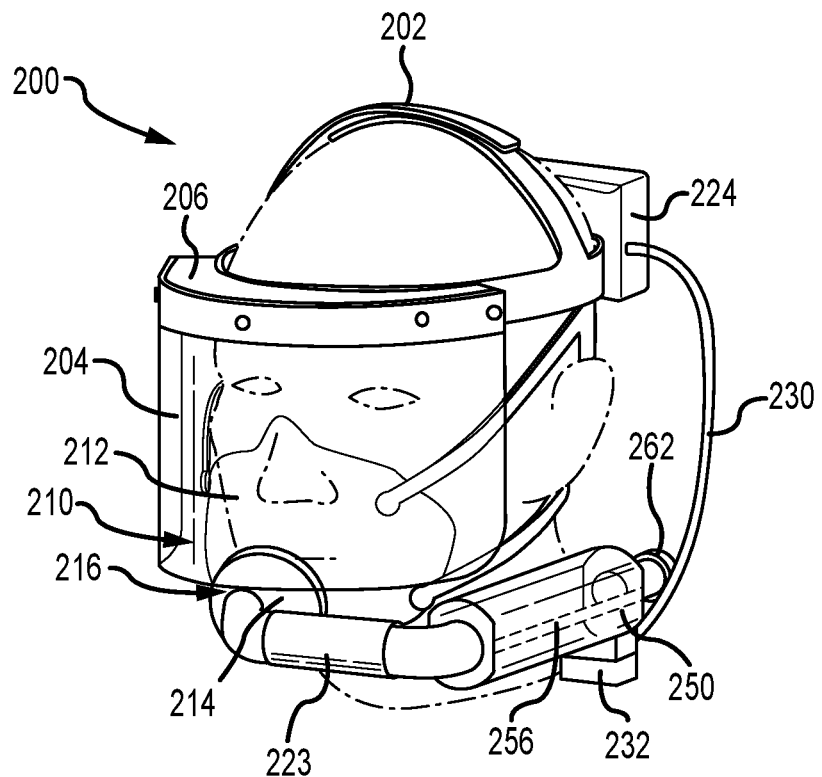
FIG. 26 is a perspective view of an electro-ionic device according to an exemplary embodiment of the present disclosure.

FIGS. 24 and 25 show other embodiments of an electro-ionic device 200 with the single ionization filter 250 supported by a head band 202 at an angle between 10 and 80 degrees, more preferably 20 and 70 degrees with respect to a transverse plane or the head band. Having the ionization filter 250 aligned at an angle may permit the opening 214 to be positioned closer to the mask 212 and reduce breathing resistance and reduce snorkel effect.

FIGS. 26-30 show various configurations of an electro-ionic device 200 with a mask subassembly 210 having a single opening 214 and a single filtrate layer 216. Further, these embodiments show various modular configurations with interchangeable masks 212, ionizing chamber(s) 250, and various mounting of the electronics unit 224.

Figure 31:
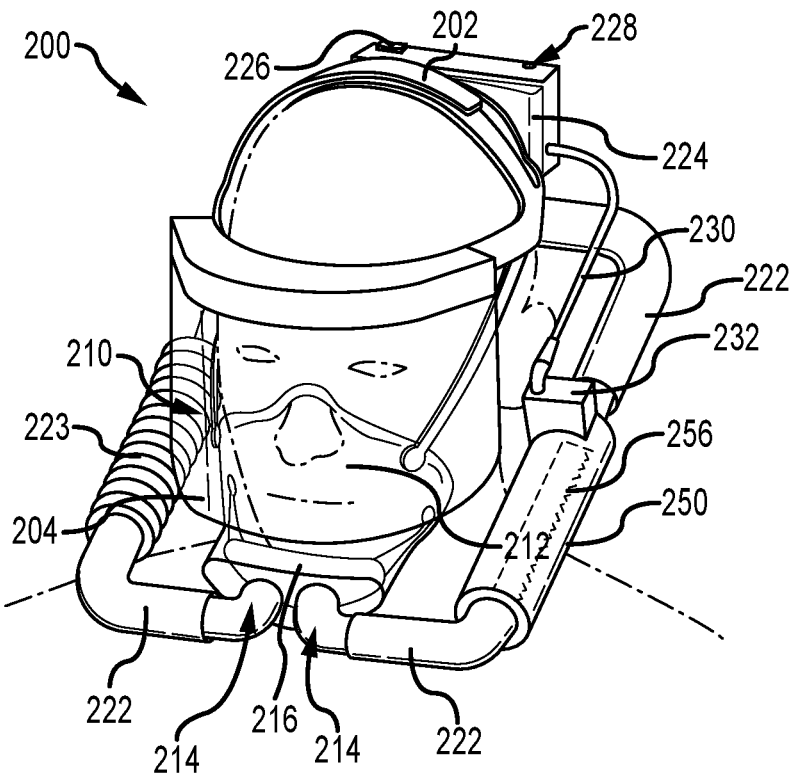
FIG. 31 is a perspective view of an electro-ionic device according to an exemplary embodiment of the present disclosure.
Figure 32:
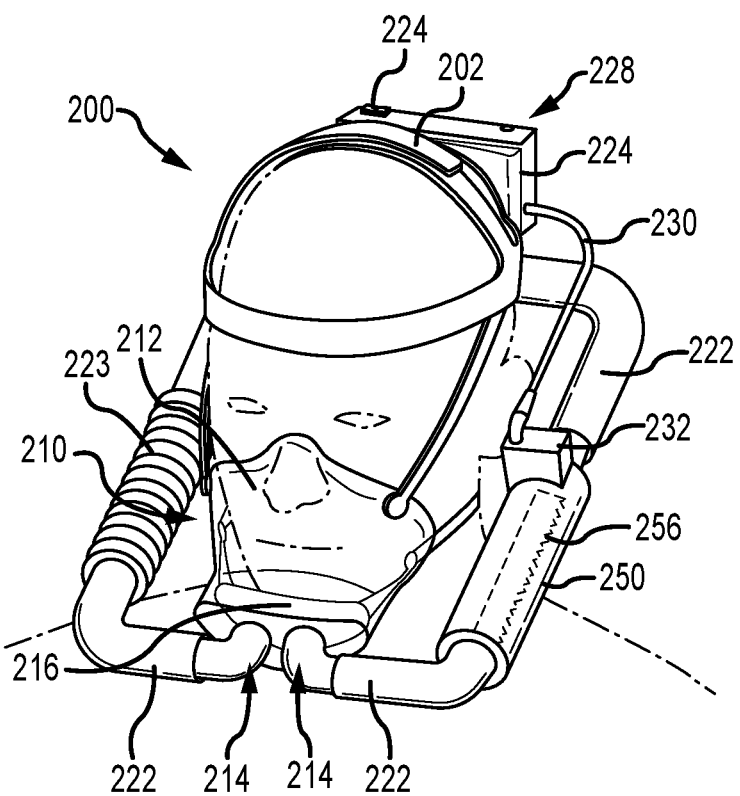
FIG. 32 is a perspective view of an electro-ionic device according to an exemplary embodiment of the present disclosure.
Figure 33:
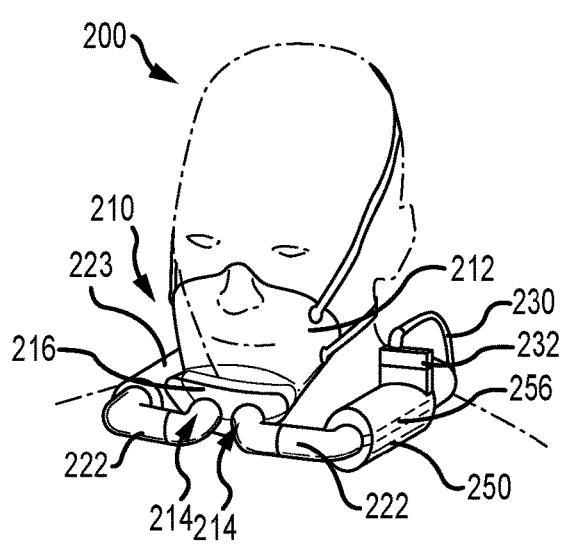
FIG. 33 is a perspective view of an electro-ionic device according to an exemplary embodiment of the present disclosure.

FIGS. 31-33 show another configuration of an electro-ionic device 200 with a mask subassembly 210 with two openings and a single filtrate layer 216. For the embodiments of FIGS. 26-33, the sectioned tubes 222, 223 and their male/female connections facilitate adjustment of the device 200 to fit a variety of user head sizes and adapt the device 200 to minimize snorkel effect. In the context of FIG. 33, the weight of the electro-ionic 200 is configured to rest on the shoulders in contrast to the embodiments of FIGS. 31 and 32, where the weight is supported substantially, if not completely, off of the head.

Figure 34:
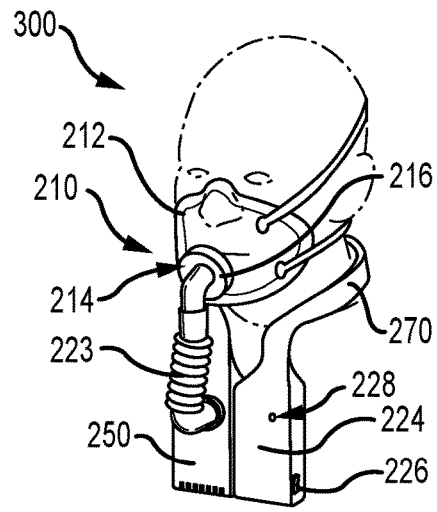
FIG. 34 is a perspective view of an electro-ionic device according to an exemplary embodiment of the present disclosure.
Figure 35:
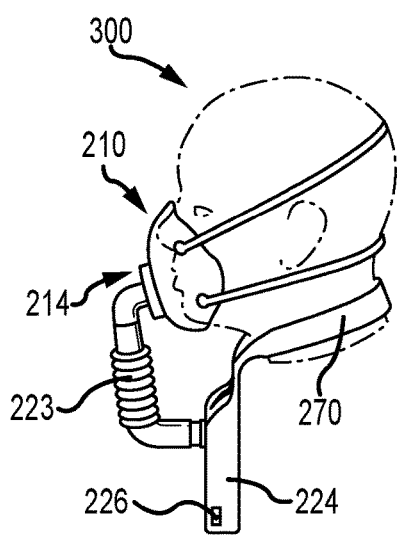
FIG. 35 is a side view of the electro-ionic device from FIG. 34.
Figure 36:
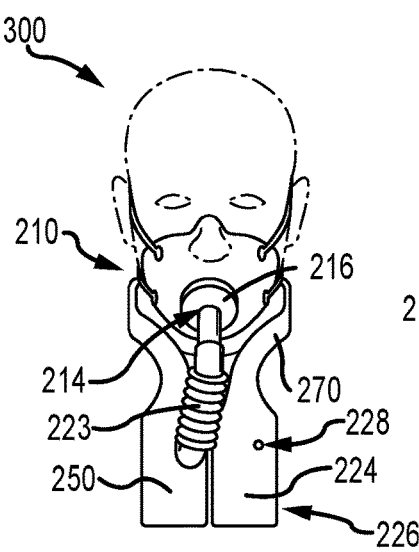
FIG. 36 is a front view of the electro-ionic device from FIG. 34.

FIGS. 34-36 shows another embodiment of an electro-ionic device 300 having similar components as the electro-ionic devices 100 and 200 discussed above. In particular, the electro-ionic device 300 may have the ionization filter 250 and the electronics unit 224 housed in the same housing or housing units that are integrally connected to each other. The housing may include a neck strap 270 configured to support the electro-ionic device 300 on the back of a user's neck and house conductive wires extending between the ionization filter 250 and the electronics unit 224. Thus, the weight of the electro-ionic device 200 for the embodiments of FIGS. 34-36 is supported off of the user's neck.

In addition, for the embodiments of FIGS. 34-36, the mask assembly 210 may include a single opening 214 and may be modular allowing for varied arrangements and adjustment of its components. Similar to the electro-ionic device 100, the electronics unit 224 may have sensors configured to detect inspiration and expiration and alter a voltage between the emitter 256 and the collector plates 260 based on whether inspiration or expiration is detected. In doing so, the emitter may be configured to emit a higher level of ozone during expiration than during inspiration. Such an ozone modulation control sequence may also employed with any of the embodiments discussed herein wherein a single airflow conduit handles both inspiration and expiration.

Figure 37:
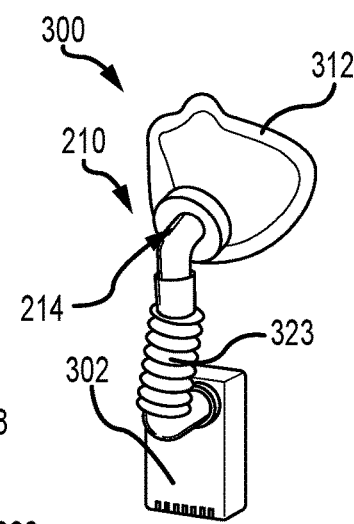
FIG. 37 is a perspective view of an electro-ionic device according to an exemplary embodiment of the present disclosure.

FIG. 37 shows another configuration of an electro-ionic device 300 having a combined housing 302, which houses both the ionization filter 250 and the electronics unit 224.

Figure 38:
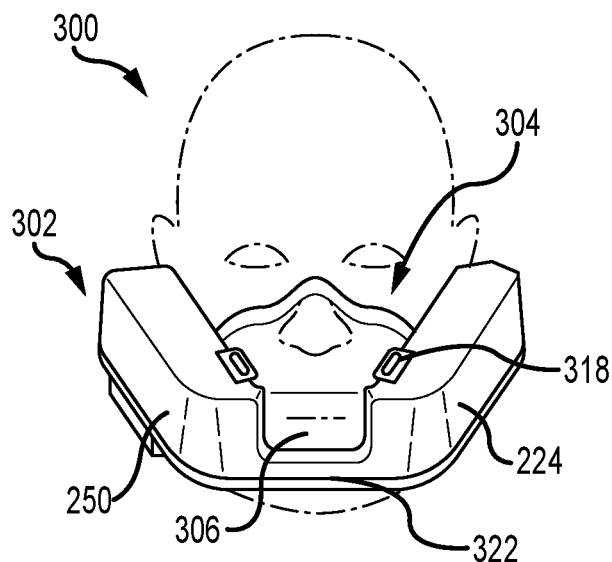
FIG. 38 is a perspective view of an electro-ionic device according to an exemplary embodiment of the present disclosure.

FIGS. 38-39H and 42 show another embodiment of an electro-ionic device 300, FIGS. 40A-40H show different views of a mask 212 of the electro-ionic device 300 from FIG. 38, and FIGS. 41A-41H show different views of a housing 302 of the electro-ionic device 300 from FIG. 38. As can be understood from FIG. 38, the housing 302 may be categorized into two general sections, one side including the ionization filter 250 and an opposite side including the electronics unit 224. The housing 302 may form a bridge portion 322 between the ionization filter 250 with the electronics unit 224 and may house electrical conductors connecting these two units to each other.

Figure 40A:
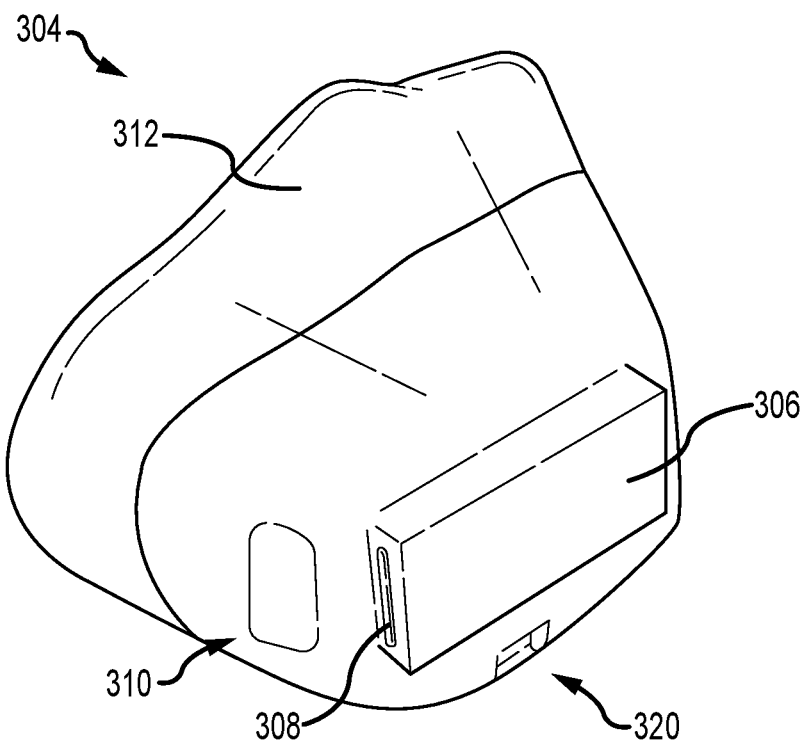
FIG. 40A is a top, front, right-side perspective view of a mask from FIG. 39A.
Figure 40B:
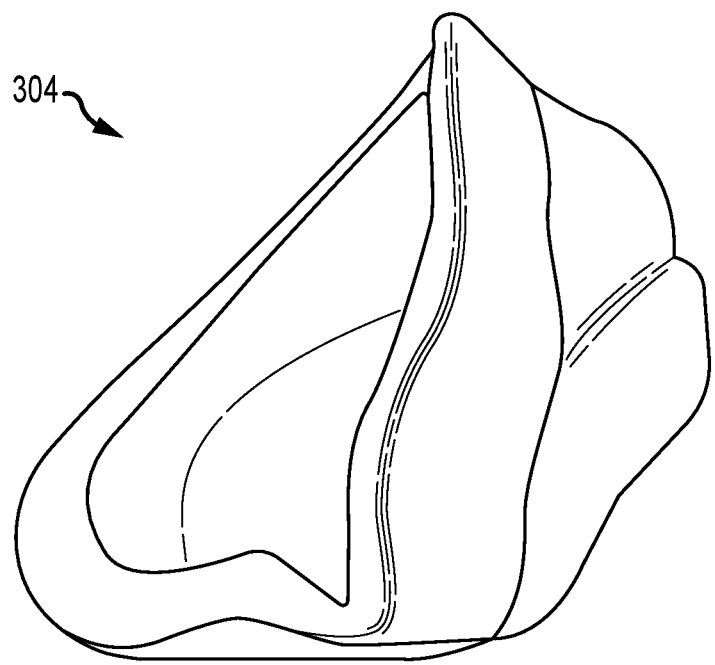
FIG. 40B is a bottom, back, left-side perspective view of the mask from FIG. 40A.
Figure 40C:
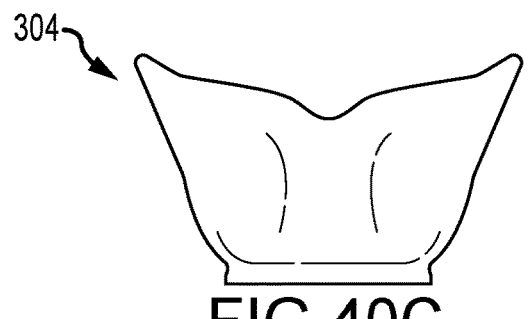
FIG. 40C is a top view of the mask from FIG. 40A.
Figure 40D:
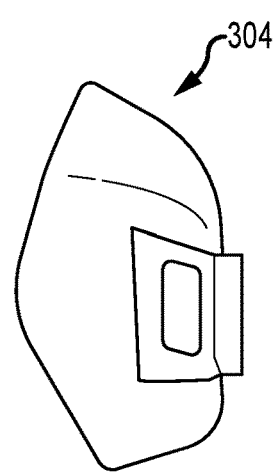
FIG. 40D is a left-side view of the mask from FIG. 40A.
Figure 40E:
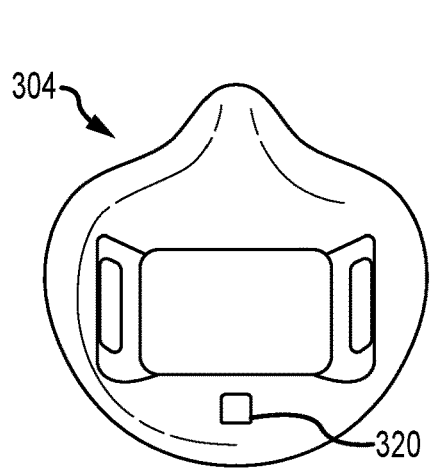
FIG. 40E is a front view of the mask from FIG. 40A.
Figure 40F:
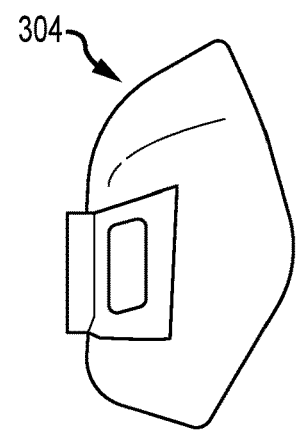
FIG. 40F is a right-side view of the mask from FIG. 40A.
Figure 40G:
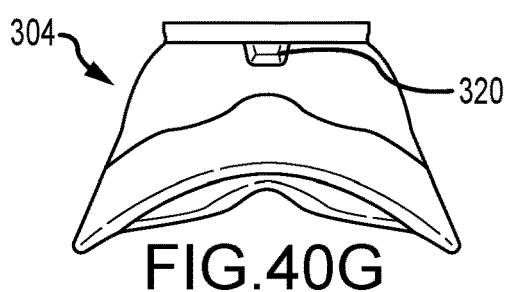
FIG. 40G is a bottom view of the mask from FIG. 40A.
Figure 40H:
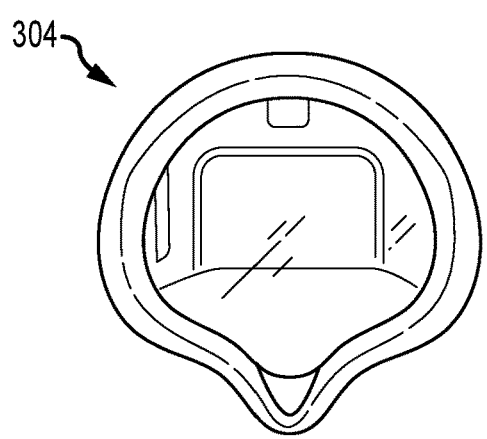
FIG. 40H is a back view of the mask from FIG. 40A.

As illustrated in FIGS. 38 and 40A, the electro-ionic device 300 may include a mask 304 similar to mask 212 in material and function. The mask 304 may have a flat window 306 in the front to enable a clear unobstructed and undistorted view of the user's mouth to minimize the impact of electro-ionic device 300 on nonverbal communication. In addition, the window 306 may include vertically aligned ribs 308 configured to slide in corresponding vertical grooves 314 (shown in FIGS. 41A and 41B) of the housing 302 for attachment thereto.

As shown in FIG. 40A, the mask 304 may have an opening 310 that opens into a corresponding opening of the ionization filter 250. The electro-ionic device 300 may also include a gasket 312 around the mask 304 to improve the fit and seal of the device to the skin. The gasket 312 may be comprised of a silicone gel, hydrogel, or polyvinyl polymers among other polymeric or elastomeric materials. The thickness of the gasket 312 may be between 0.5-6.0 mm, preferably 1-4 mm and applied to both sides of the mask 304 or folded over onto both sides of the mask 304. The gasket 312 may include tabs or protrusions to assist the user in removing it from the face. As described above in reference to the devices 100 and 200, the electro-ionic device 300 may also have a port (not shown) for receiving a straw from a beverage to maintain hydration levels all day without removing the electro-ionic device 300.

Figure 41A:
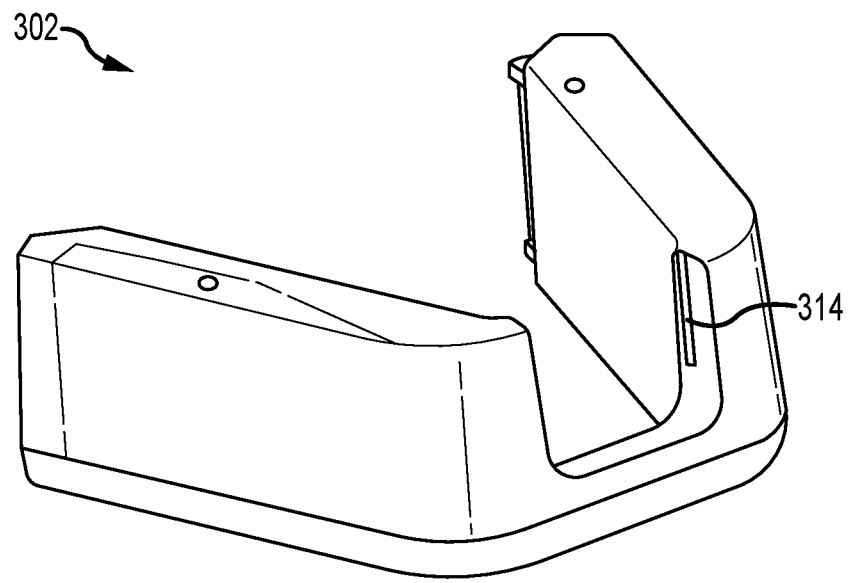
FIG. 41A is a top, front, right-side perspective view of a housing from FIG. 39A.
Figure 41B:
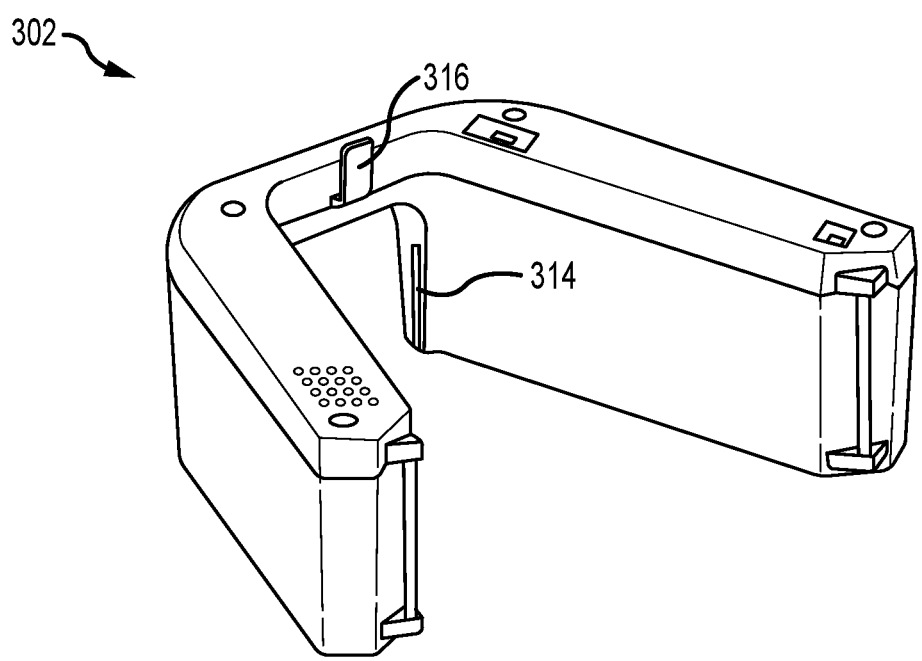
FIG. 41B is a bottom, back, left-side perspective view of the housing from FIG. 41A.

In addition to the mask window ribs 308 and the housing grooves 314, as illustrated in FIGS. 40A and 41B, a lower mask hook 316 of the housing 302 may engage a corresponding slot 320 to help align and secure the mask 304 to the housing 302. After the ribs 308 of the mask window 306 and the grooves 314 of the housing 302 are aligned, removable upper mask clips 318 are configured to secure the mask 304 to the housing 302, as depicted in FIGS. 38 and 43A.

Figure 39A:
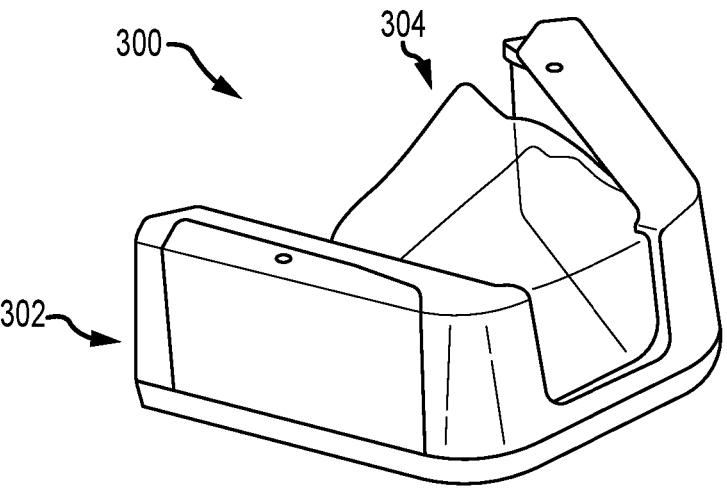
FIG. 39A is a top, front, right-side perspective view of an electro-ionic device according to an exemplary embodiment of the present disclosure.
Figure 39B:
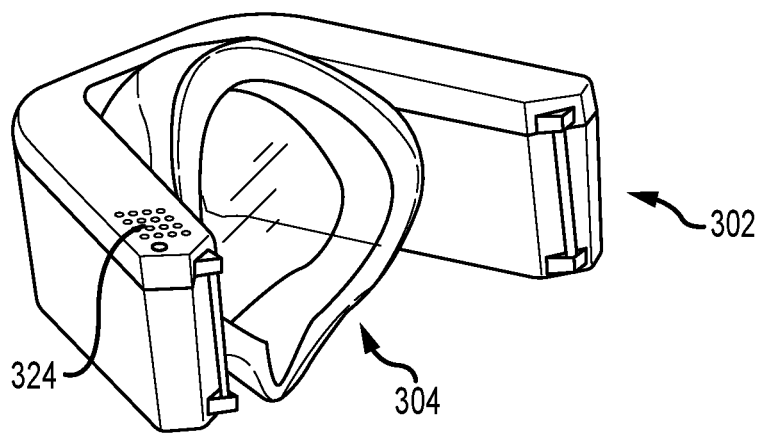
FIG. 39B is a bottom, back, left-side perspective view of the electro-ionic device from FIG. 39A.
Figure 39C:
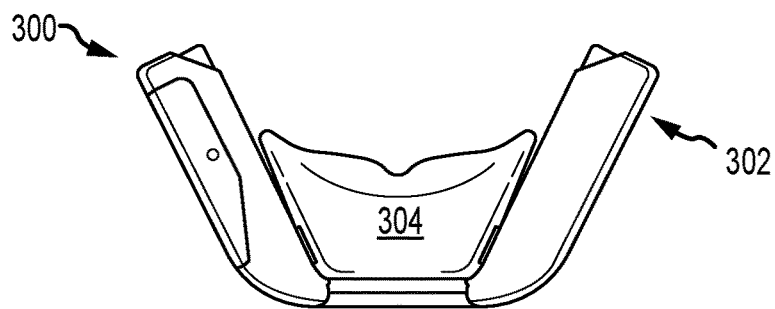
FIG. 39C is a top view of the electro-ionic device from FIG. 39A.
Figure 39D:
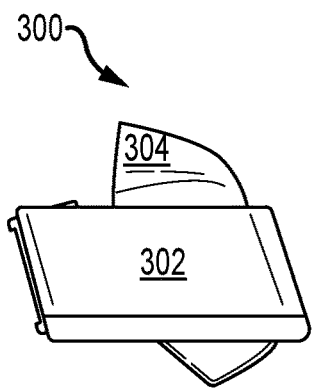
FIG. 39D is a left-side view of the electro-ionic device from FIG. 39A.
Figure 39E:
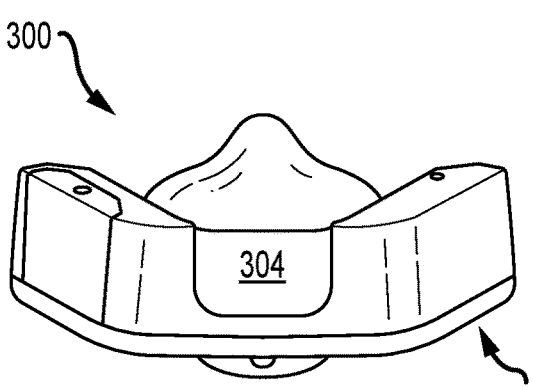
FIG. 39E is a top, front perspective view of the electro-ionic device from FIG. 39A.
Figure 39F:
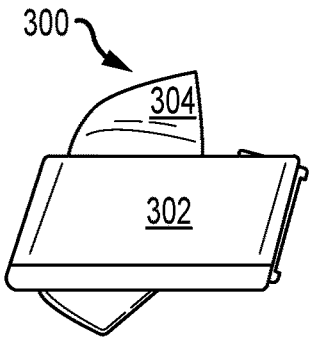
FIG. 39F is a right-side view of the electro-ionic device from FIG. 39A.
Figure 39G:
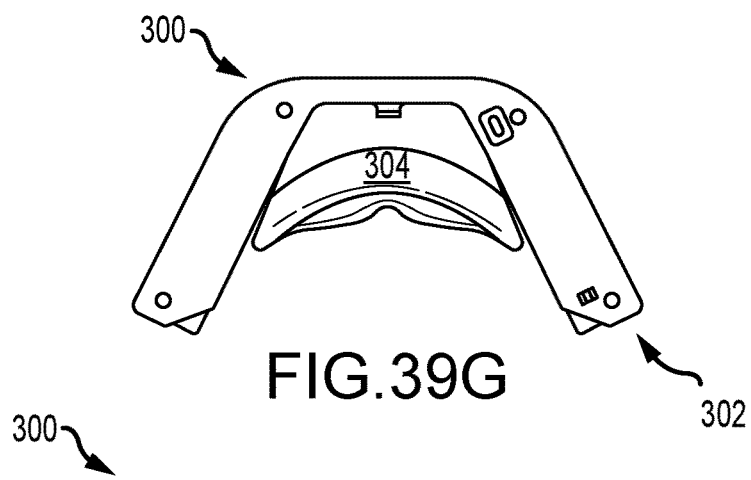
FIG. 39G is a bottom view of the electro-ionic device from FIG. 39A.
Figure 39H:
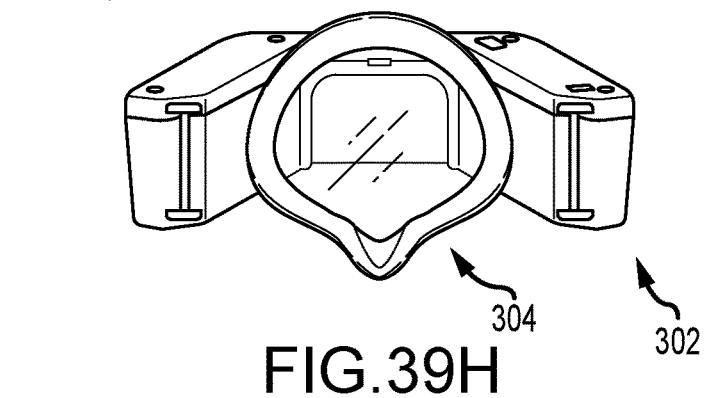
FIG. 39H is a bottom, back perspective view of the electro-ionic device from FIG. 39A.

As illustrated in FIG. 39B, the housing 302 of electro-ionic device 300 may include an opening 324 which may function as an inlet and outlet to the ionization filter 250. The ionization filter 250 and the electronics unit 224 include the same components and operate in the same or similar manner as discussed above with regard to electro-ionic devices 200 and 300.

As shown in FIG. 42, the ionization filter 250 includes collector plates 260 spaced apart from the emitter 256, and the electronics unit 224 is located on the opposite side. In other embodiments, the electro-ionic device 300 may include two ionization filters 250, one housed on each side of the device.

FIGS. 43A-43C show another embodiment of the electro-ionic device 300 similar to the embodiment shown in FIGS. 38-42 with a smaller sized housing 302 that offers a reduction in view obstruction. However, this embodiment may also include dual ionization filters 250 inside the housing 302 and an external electronics unit 224, similar to some of the embodiments discussed above, the external electronics unit 224 being tethered to the rest of the device 300 via a cable 230.

Figure 44A:
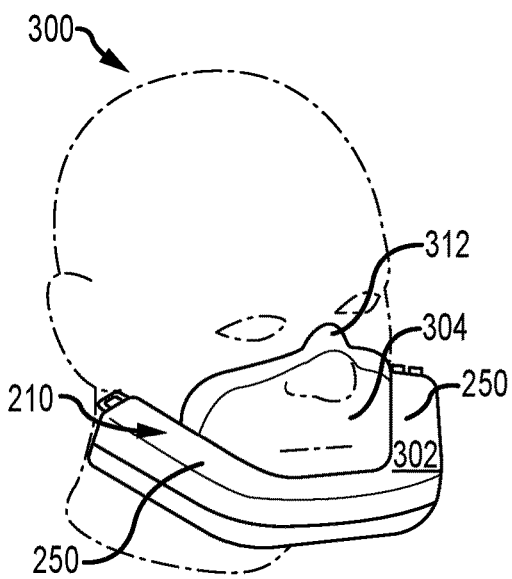
FIG. 44A is a top, front, left-side perspective view of an electro-ionic device according to an exemplary embodiment of the present disclosure.
Figure 44B:
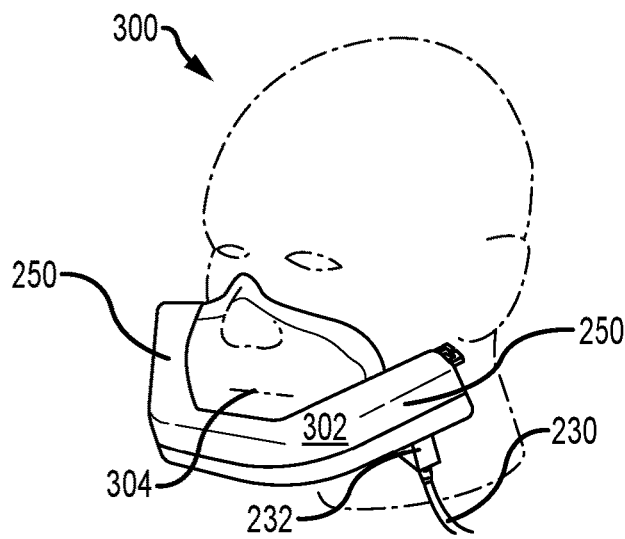
FIG. 44B is a top, front, right-side perspective view of the electro-ionic device from FIG. 44A.

FIGS. 44A and 44B show another embodiment the electro-ionic device 300 similar to the embodiment shown in FIGS. 43A-43C with a different housing 302 that is yet smaller and offers further reduced view obstruction. This embodiment may also include dual ionization filters 250 inside the housing 302 and an external electronics unit 224, similar to some of the embodiments discussed above, the external electronics unit 224 being tethered to the rest of the device 300 via a cable 230.

Figure 45A:
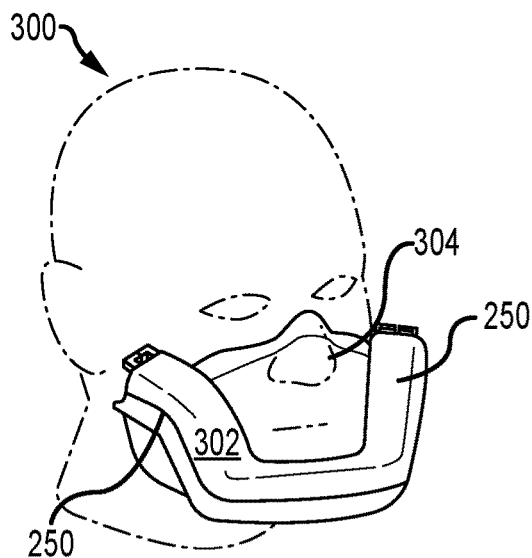
FIG. 45A is a top, front, left-side perspective view of an electro-ionic device according to an exemplary embodiment of the present disclosure.
Figure 45B:
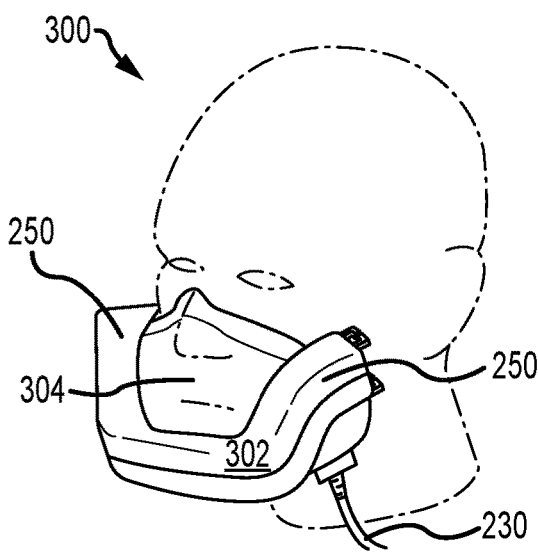
FIG. 45B is a top, front, right-side perspective view of the electro-ionic device from FIG. 45A.
Figure 46A:
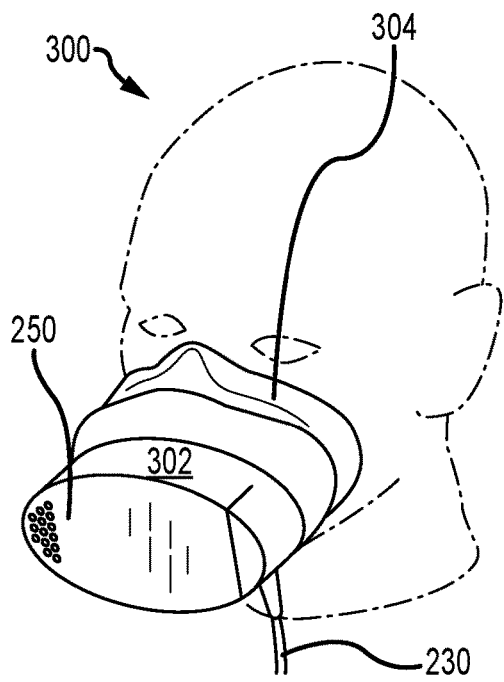
FIG. 46A is a perspective view of an electro-ionic device according to an exemplary embodiment of the present disclosure.
Figure 46B:
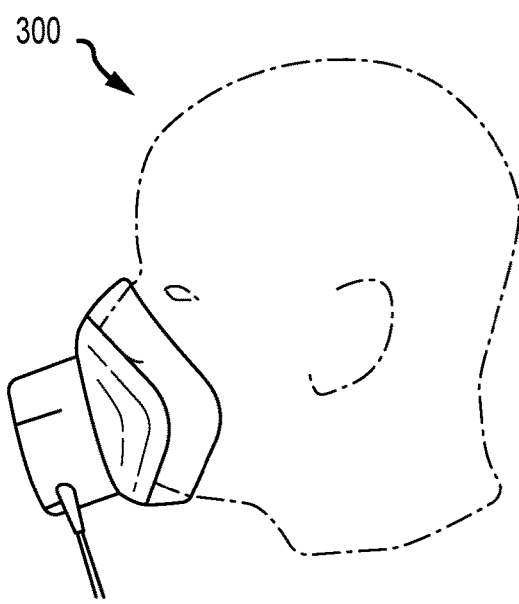
FIG. 46B is a side view of the electro-ionic device from FIG. 46A.
Figure 46C:
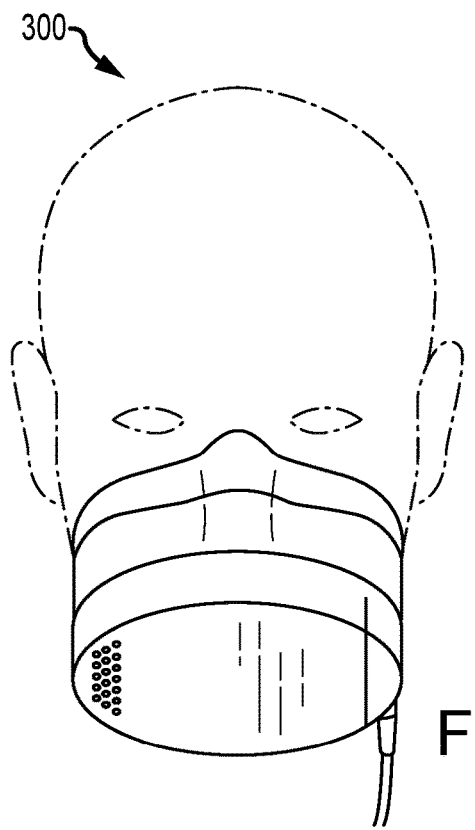
FIG. 46C is a front view of the electro-ionic device from FIG. 46A.
Figure 48A:
FIG. 48A is a perspective view of an electro-ionic device according to an exemplary embodiment of the present disclosure.
Figure 48B:
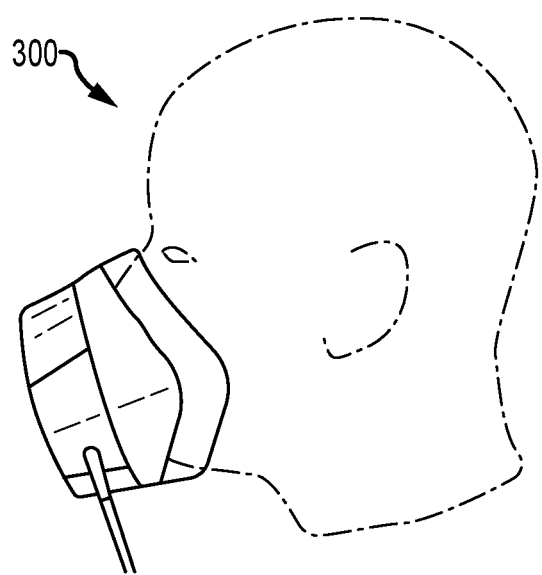
FIG. 48B is a side view of the electro-ionic device from FIG. 48A.
Figure 48C:
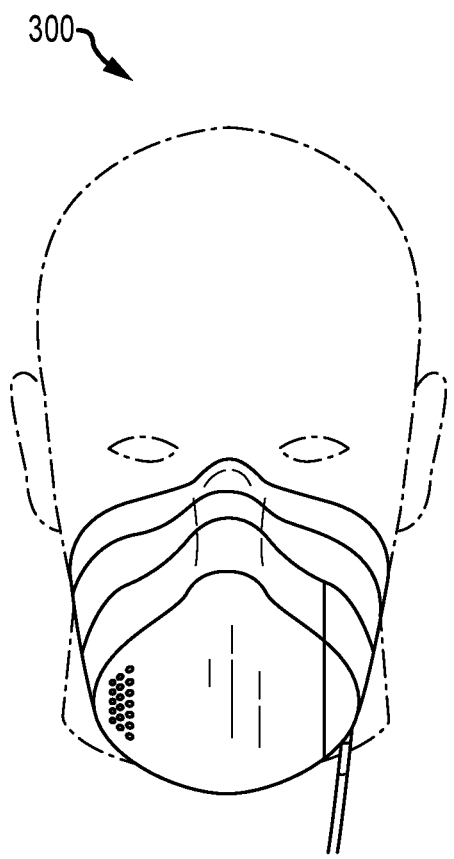
FIG. 48C is a front view of the electro-ionic device from FIG. 48A.
Figure 49A:
FIG. 49A is a perspective view of an electro-ionic device according to an exemplary embodiment of the present disclosure.
Figure 49B:
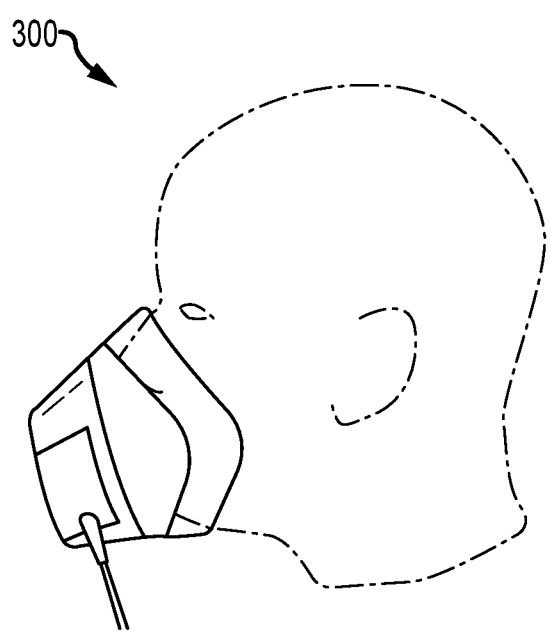
FIG. 49B is a side view of the electro-ionic device from FIG. 49A.
Figure 49C:
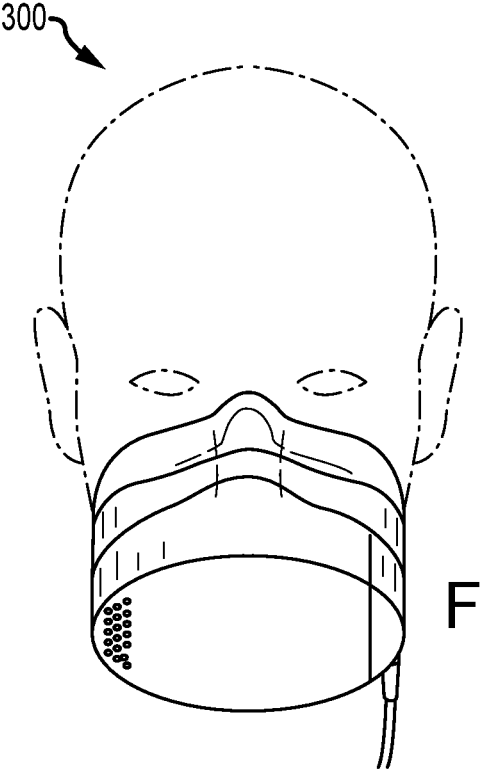
FIG. 49C is a front view of the electro-ionic device from FIG. 49A.
Figure 50A:
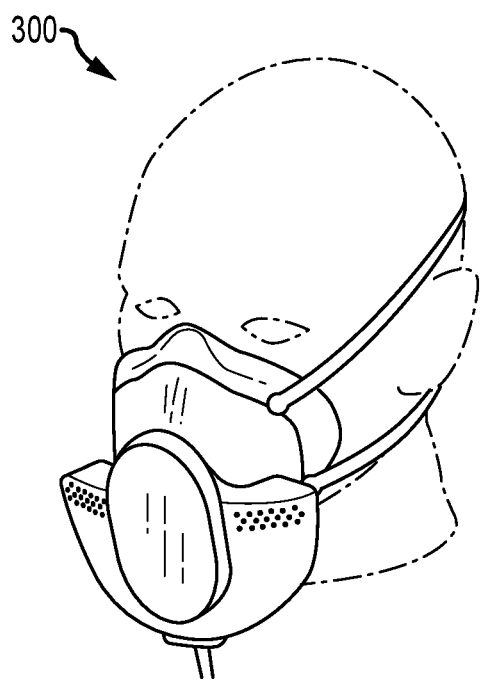
FIG. 50A is a perspective view of an electro-ionic device according to an exemplary embodiment of the present disclosure.
Figure 50B:
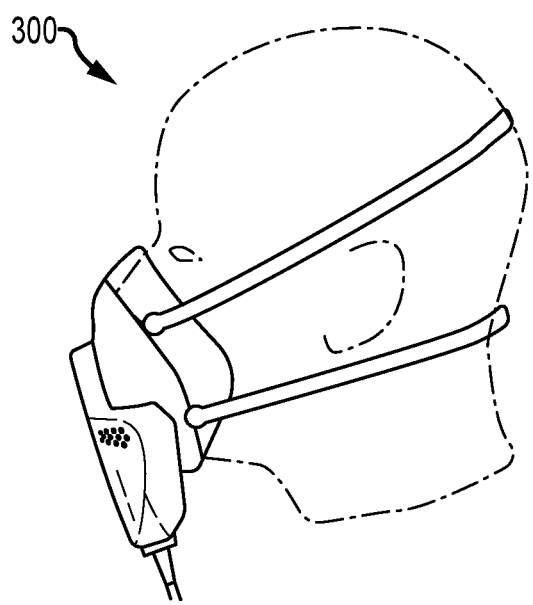
FIG. 50B is a side view of the electro-ionic device from FIG. 50A.
Figure 50C:
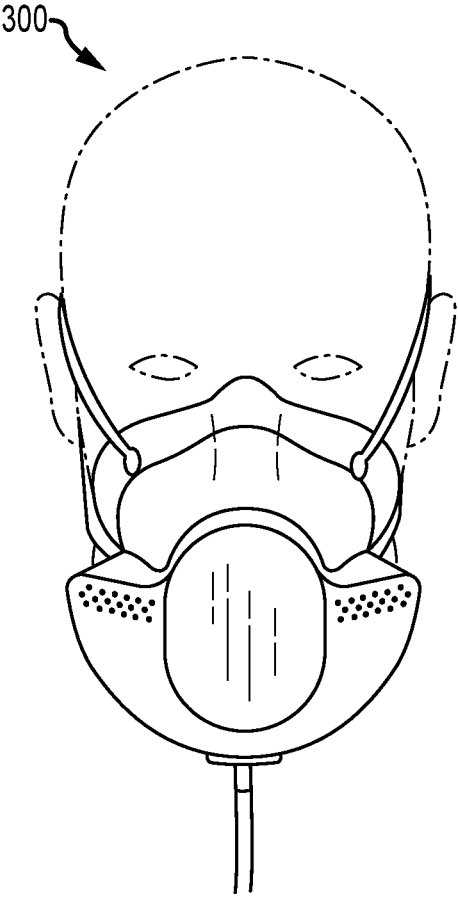
FIG. 50C is a front view of the electro-ionic device from FIG. 50A.
Figure 51A:
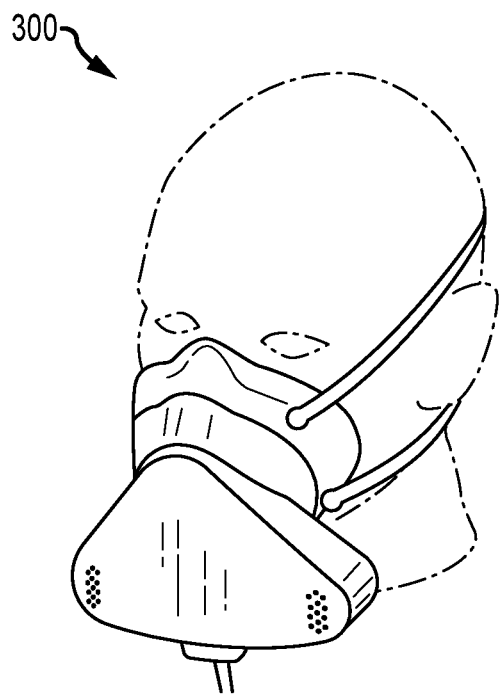
FIG. 51A is a perspective view of an electro-ionic device according to an exemplary embodiment of the present disclosure.
Figure 51B:
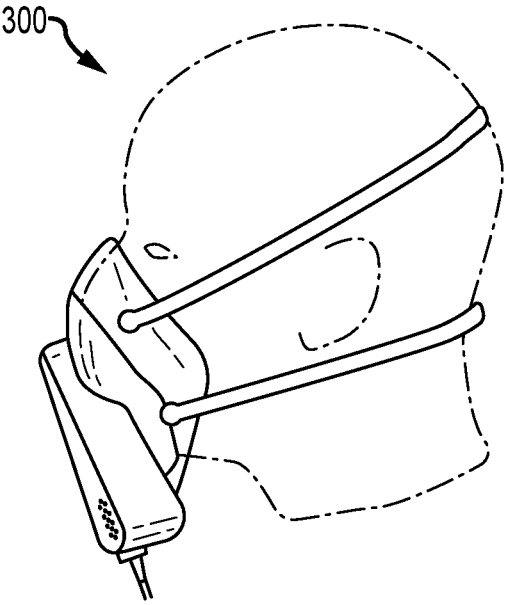
FIG. 51B is a side view of the electro-ionic device from FIG. 51A.
Figure 51C:
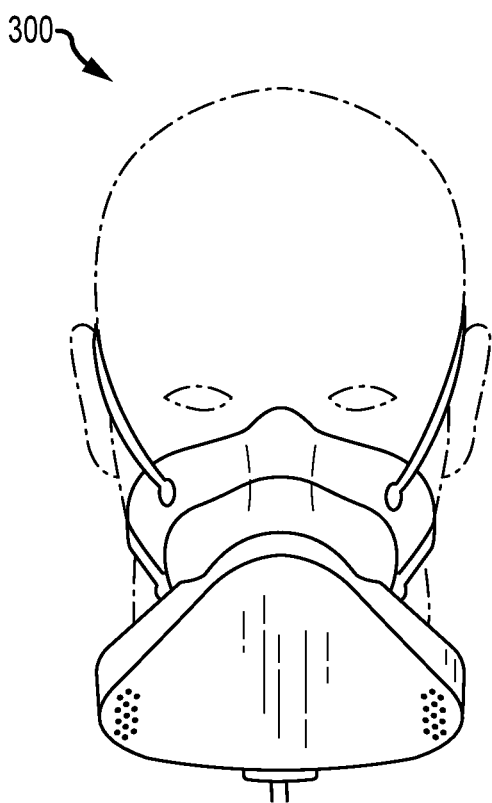
FIG. 51C is a front view of the electro-ionic device from FIG. 51A.
Figure 52A:
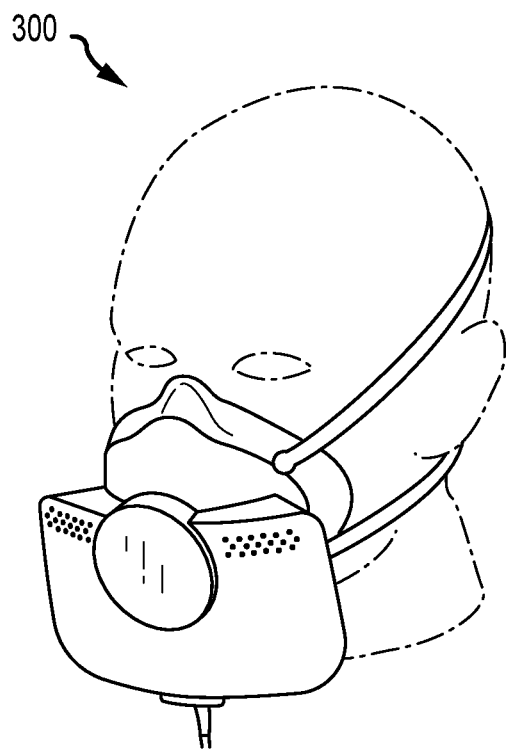
FIG. 52A is a perspective view of an electro-ionic device according to an exemplary embodiment of the present disclosure.
Figure 52B:
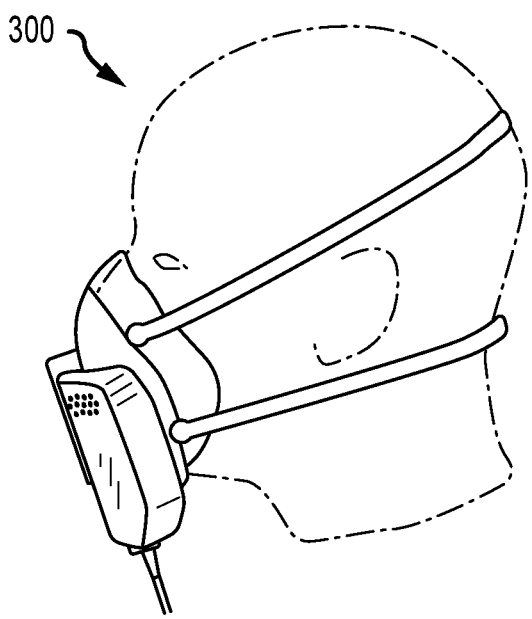
FIG. 52B is a side view of the electro-ionic device from FIG. 52A.
Figure 52C:
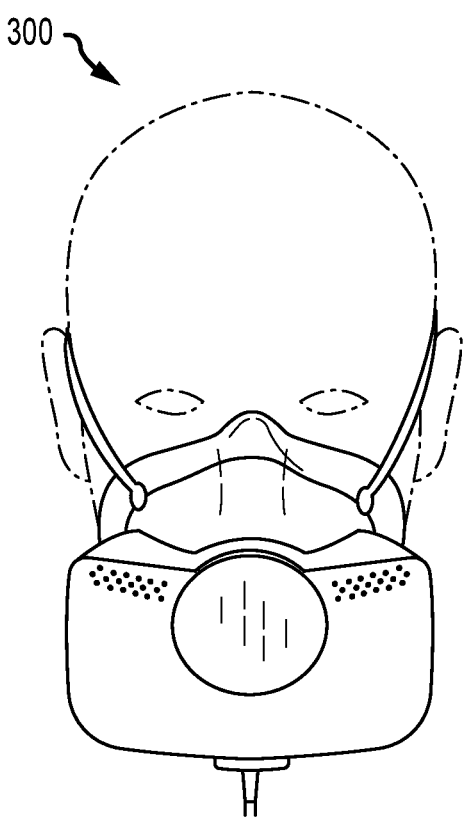
FIG. 52C is a front view of the electro-ionic device from FIG. 52A.

FIGS. 45A and 45B also show another embodiment the electro-ionic device 300 similar to the embodiment shown in FIGS. 43A-43C with a different housing 302 and offering similar benefits and features.

Embodiments of the electro-ionic device 300 shown in FIGS. 46A-46C, 47A-47C, 48A-48C, 49A-49C, 50A-50C, 51A-51C, and 52A-52C are similar to the embodiment shown in FIGS. 43A-43C with differently sized and shaped housings 302.

Figure 53:
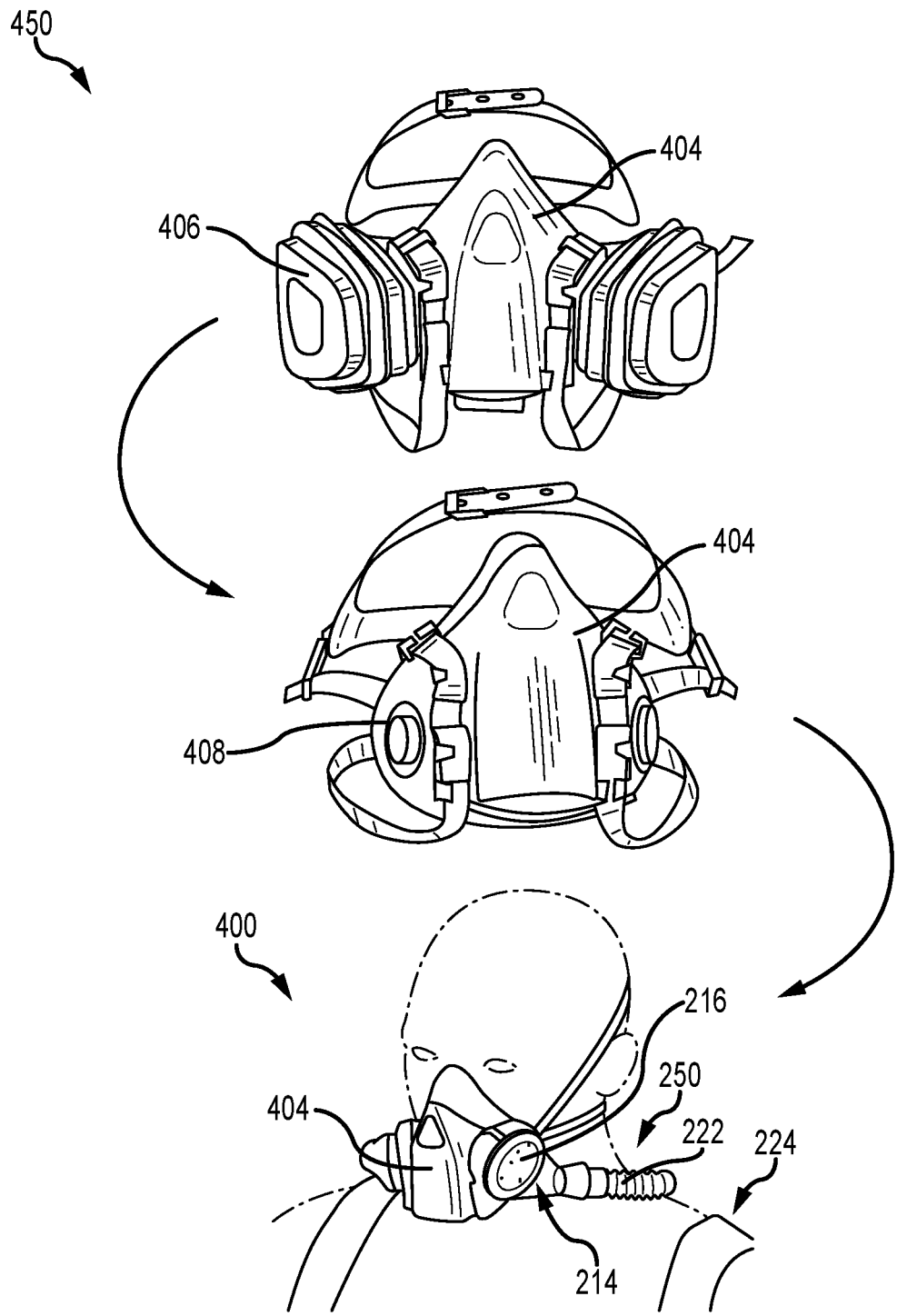
FIG. 53 is perspective diagram showing an electro-ionic device in various states.

FIG. 53 shows an exemplary embodiment of an electro-ionic device 400 and system 450. The system 450 may comprise a mask 404 having filter cartridges 406 that are interchangeable with the ionization filter 250 and associated tubing 222, electronics unit 224, etc. similar to the embodiment shown in FIG. 17. In particular, the mask 404 may have openings 408 configured to fit disposable filter cartridges 406 in a first configuration. The cartridges 406 may be removed from the mask and replaced with and the valves 220, filtrate layer 216, opening 214 and tubing 222 which may connect to an ionization filter 250 carried remotely on a user's back, for example. In other words, the ionization filter 250 may be adapted to work with currently marketed masks 404 configured for employing disposable filter cartridges 406.

Figure 54:
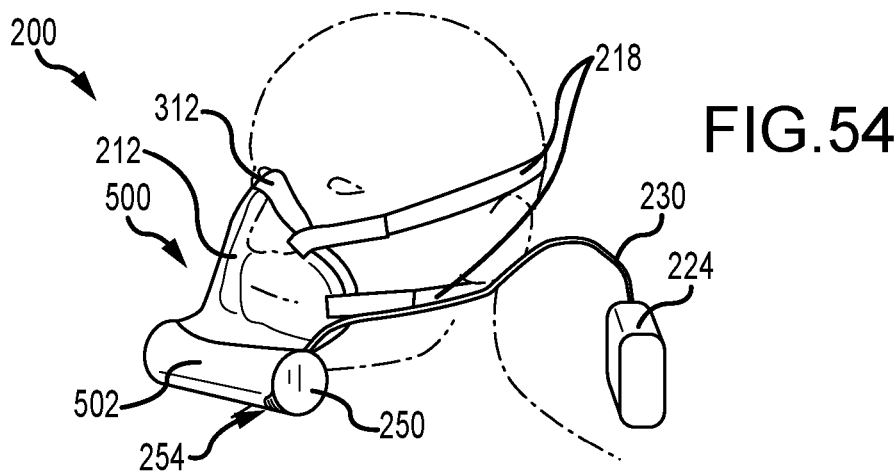
FIG. 54 is a perspective view of an electro-ionic device.

FIGS. 54-60 illustrate various views of another embodiment of the electro-ionic device 200 and its various components, wherein the embodiment includes a modular ionization filter that is removable from the rest of the electro-ionic device for cleaning/sanitizing purposes. As shown in FIG. 54, the electro-ionic device 200 includes a mask assembly 500 coupled to the user via straps 218. The electronics unit 224 is separate from the mask assembly 500 and coupled to the mask assembly 500 via the cable 230.

Figure 56:
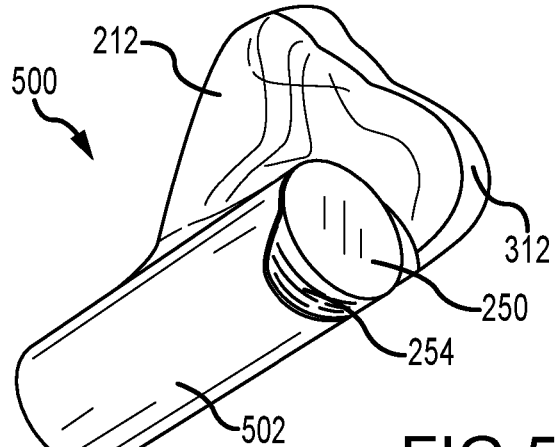
FIG. 56 is a bottom-front perspective view of the mask assembly of FIG. 55.
Figure 55:
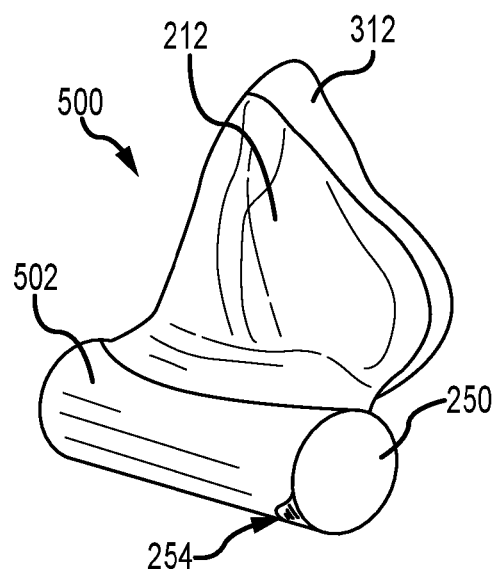
FIG. 55 is a front a top-front perspective view of a mask assembly of the electro-ionic device of FIG. 54.
Figure 57:
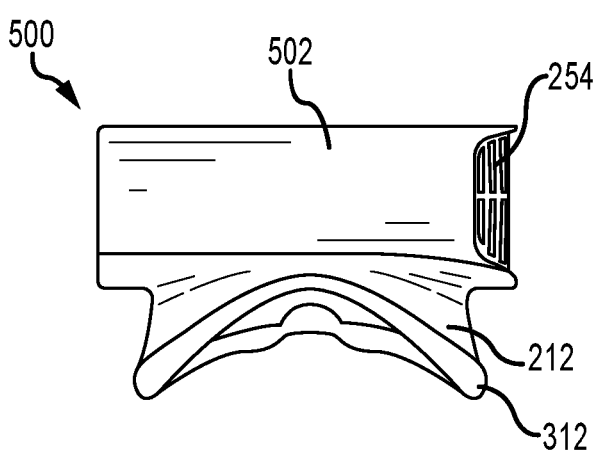
FIG. 57 is a bottom view of the mask assembly of FIG. 55.
Figure 58:
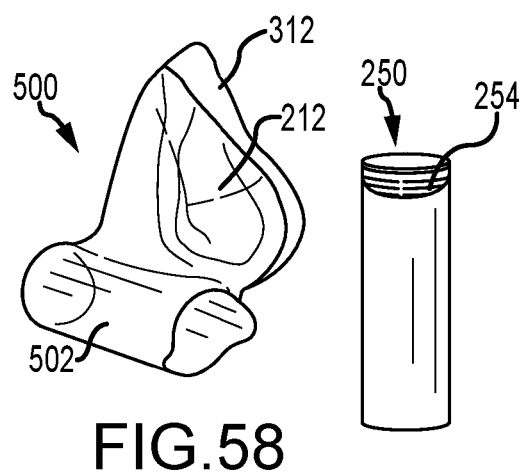
FIG. 58 is a top-front view of the mask assembly of FIG. 55 with the modular ionization filter removed from the mask, thereby allowing the ionization filter to be sanitized separately from the rest of the mask assembly.

As illustrated in FIGS. 56-57, the mask assembly 500 includes the mask 212 with an integrally formed receptacle 502 in which the ionization filter 250 is removably received, as shown in FIG. 58, thereby allowing the ionization filter 250 to be separately washed/cleaned/sanitized from the rest of the mask assembly 500. The mask 212 also includes the gasket 312 as described above in detail with respect to other embodiments.

Figure 59:
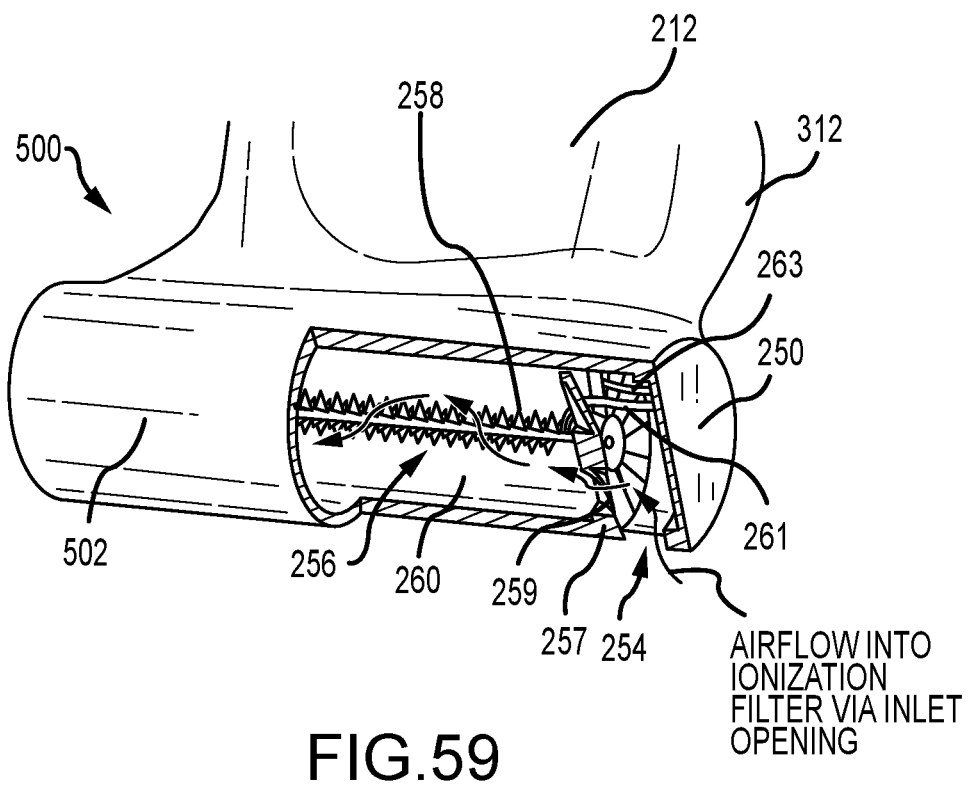
FIG. 59 is an enlarged cutaway view of the ionization filter of the view depicted in FIG. 54.
Figure 60:
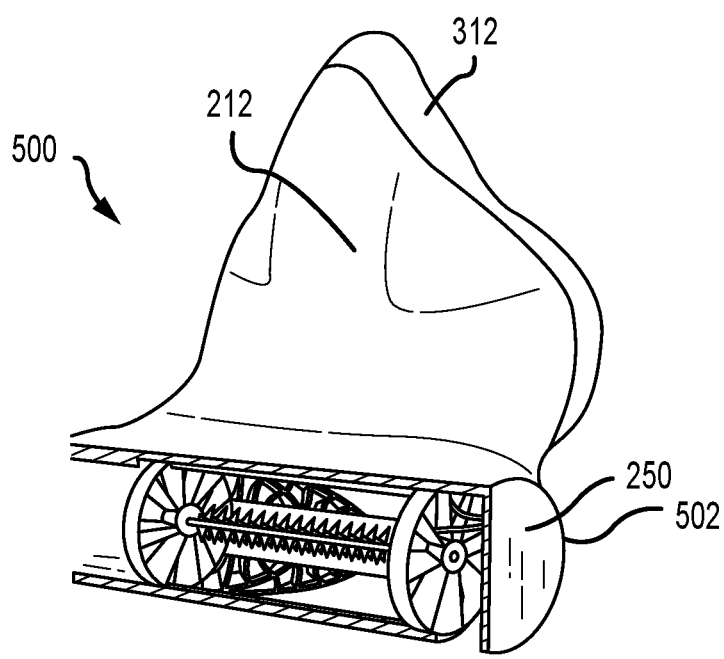
FIG. 60 is the same view as FIG. 59, except the ionization filter is more fully sectioned to show more of its interior, the interior being the same as shown in FIG. 9B.
Figure 61:
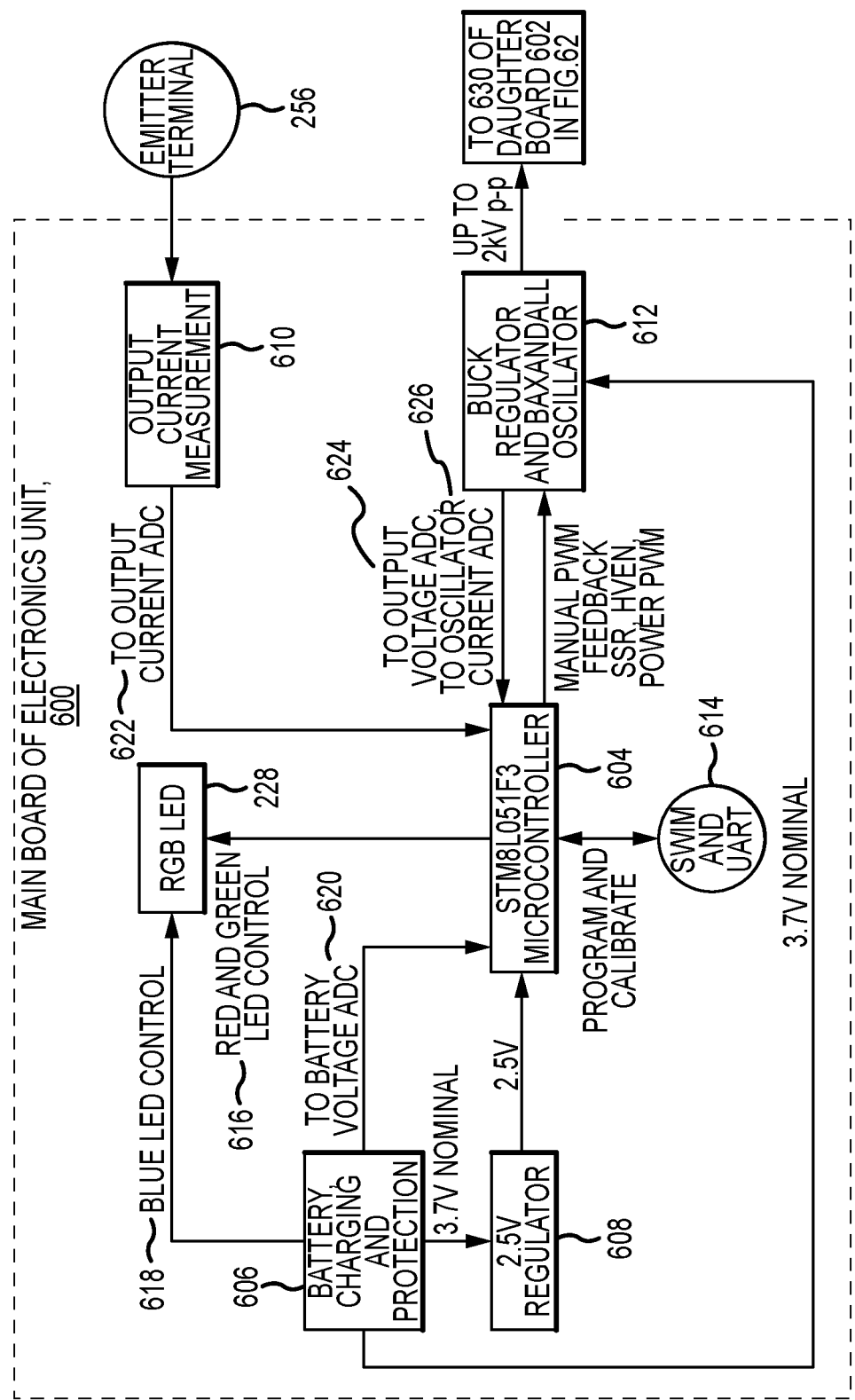
FIG. 61 is a circuit schematic of the main board contained in the electronics unit of any of the embodiments of the electro-ionic device disclosed herein.
Figure 62:
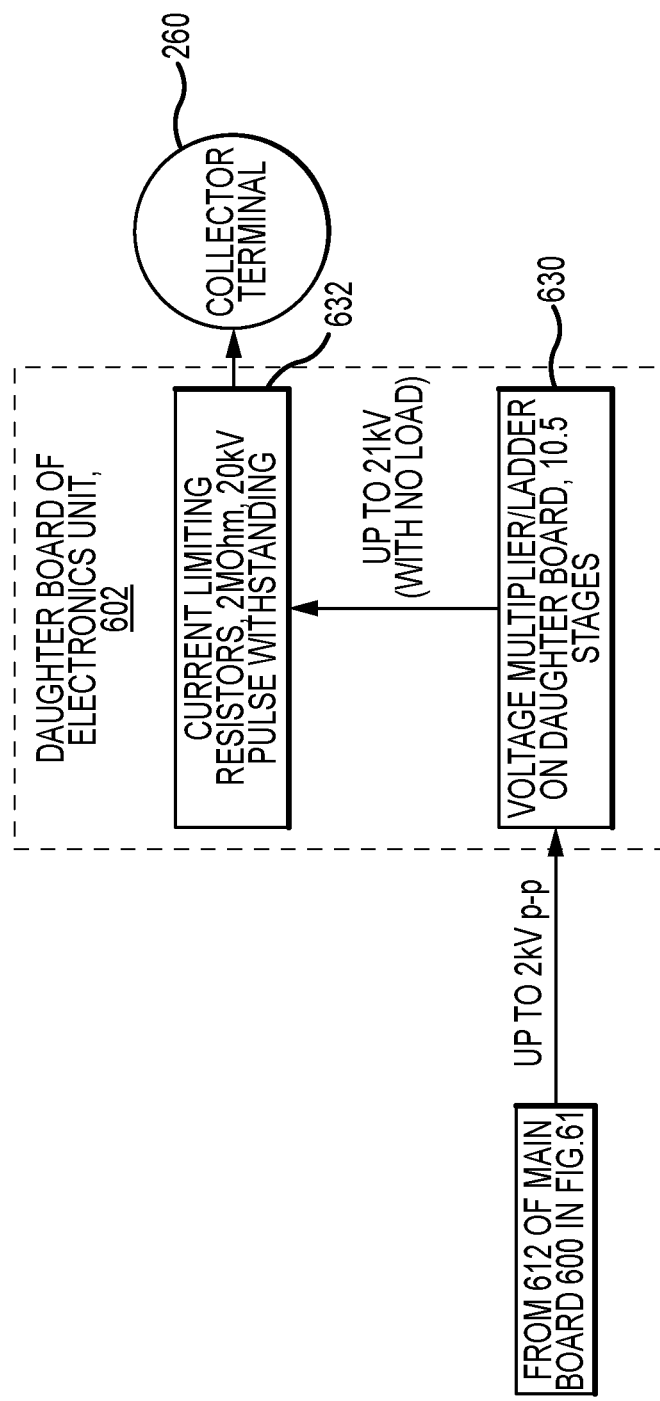
FIG. 62 is a circuit schematic of the daughter board contained in the electronics unit of any of the embodiments of the electro-ionic device disclosed herein, the daughter board being electrically coupled to the main board of FIG. 61.
Figure 63:
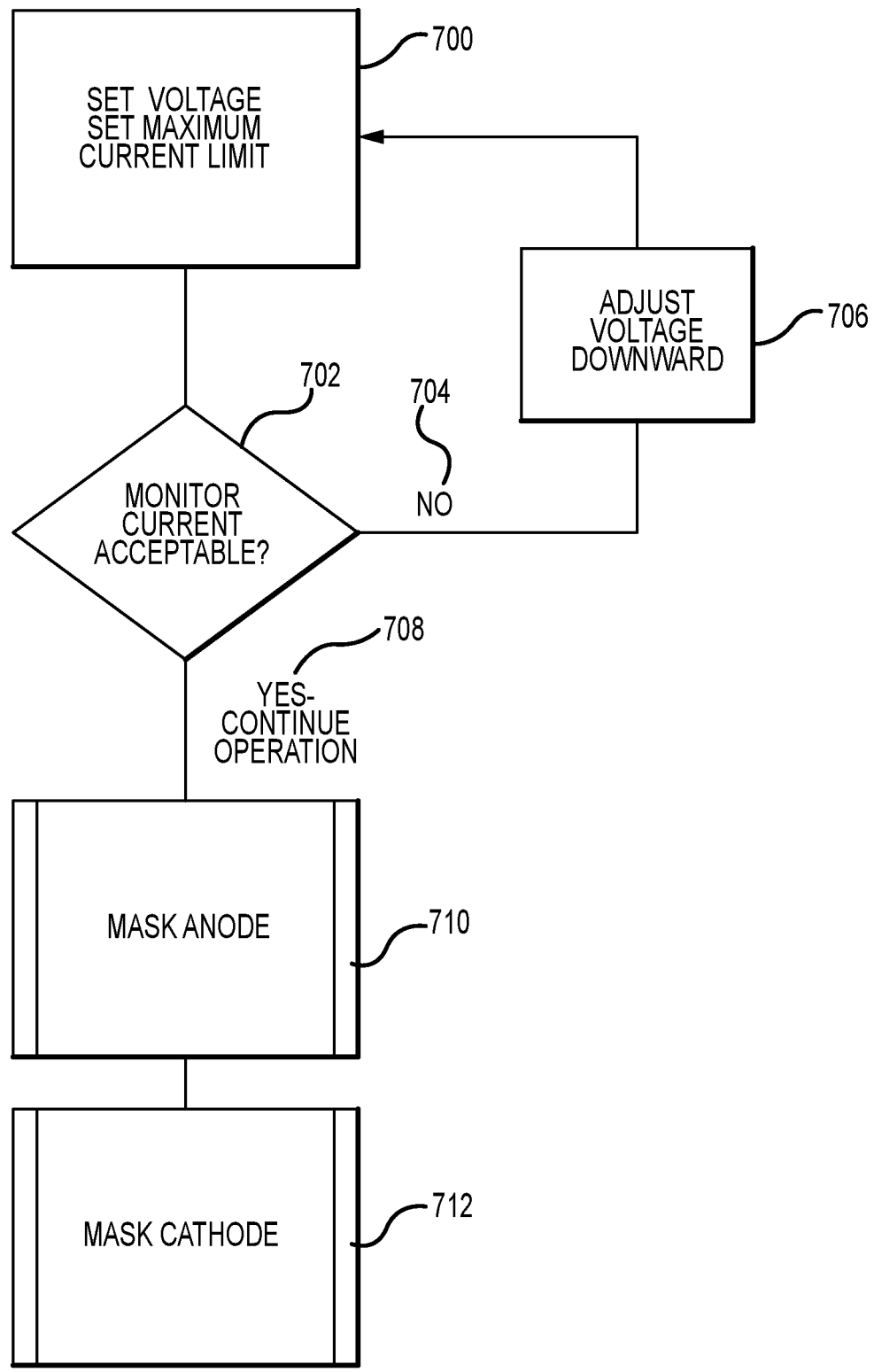
FIG. 63 is a flow chart illustrating voltage modulation for the ionization filter of any of the embodiments of the electro-ionic device disclosed herein.

FIG. 59 is an enlarged cutaway view of the ionization filter of the view depicted in FIG. 54, and FIG. 60 is the same view as FIG. 59, except the ionization filter is more fully sectioned to show more of its interior. A comparison of FIGS. 9B and 60 make it clear that the internal components of the ionization filters depicted in these two figures are identical, including the emitter 256, collector 260, spiral vanes 259 of the spacers 257 and conductors 261, 263 leading to the emitter and collector. Therefore, the discussion of these components as discussed above with respect to FIG. 9B is applicable to what is depicted in FIG. 60 and will not be repeated here.

As shown in FIG. 59, upon inhalation by the wearer of the mask 221, contaminated air from the surrounding environment enters the opening 254 and passes through the spiral spacer 257. The vanes 259 of the spiral spacer cause the airflow to spiral through the chamber of the ionization filter 250 as the airflow moves along the length of the emitter 256 between the collector 260 and the emitter 256. This spiraling of the airflow within the chamber increases the dwell time of the airflow in the chamber, allowing increased exposure to the emitter and collector than would otherwise be possible for a chamber of such reduced length. As discussed above, the emitter and collector work together to precipitate contaminates out of the airflow as the airflow spirals along the emitter.

It should be understood, that while the airflow spirals within the chamber on account of the spiral vanes 259 of the spacer 257, or may even be turbulent as opposed to laminar flow within the chamber, all of which serves to increase the dwell time of the airflow within the chamber, the general direction of airflow within the chamber is substantially, if not completely, parallel to the longitudinal axis of the emitter and collector, as can be understood from the above discussion regarding Arrows C with respect to FIGS. 9A and 9B. Also, as depicted in FIGS. 9A and 9B, the offset distance (Arrow D) between the tips of the emitter and the collector are the same for the arrangement of the emitter and collector in the embodiments depicted in FIGS. 59 and 60.

As illustrated in FIG. 59, the inhalation spiral airflow eventually reaches an opening into the volume of the mask 212 (i.e., the mask space). At this point, the airflow has been filtered to protect the wearer of the mask 212 from any contaminates that entered the opening 254 of the ionization filter 250 and were precipitated out of the airflow in the chamber of the ionization filter 250. As discussed above, tested filtration rates for this ionization filter 250 have been 99.8% viral penetration reduction in the context of a COVID-19 aerosol study with COVID-19 aerosol concentrations at much higher levels than would ever be encountered in real life.

Still referring to FIG. 59, depending on the embodiment and as can be understood from the above discussions regarding the various embodiments of the elector-ionic device 200, upon exhalation by the wearer of the mask 212, exhaled airflow contaminated by the wearer may be ported from the mask volume directly outside the mask without further ionization filtration, a one-way valve preventing reverse flow back into the inhalation ionization filter 250. Alternately, the exhaled air may be routed through a second or exhalation ionization filter for similar filtration as already described before the exhaled air reaches the surrounding environment, a one-way valve again preventing reverse flow back into the inhalation ionization filter 250.

Finally, in the specific embodiments depicted in FIGS. 54-60, the ionization filter 250 serves to filter both for inhalation and exhalation. In doing so, the exhaled airflow may simply reverse direction back through the ionization filter 250 to be filtered before exiting the opening 254 into the surrounding environment as filtered exhaled air. As discussed above with respect to similar embodiments where a single ionization filter 250 serves double duty for inhalation and exhalation, sensors identify periods of inhalation versus exhalation and modulates the voltage such that ozone levels are lower upon inhalation and higher upon exhalation.

FIGS. 61 and 62 are respectively circuit schematics of the main board 600 and the daughter board 602 contained in the electronics unit 224 of any of the above-discussed embodiments of the electro-ionic device 100, 200 and 300, including the device 200 depicted in FIG. 54. As shown in FIG. 61, the main board 600 includes a microcontroller 604, a battery module 606 with charging and protection controls, a 2.5 V regulator 608, an output current measurement module 610, a Buck regulator and Baxandall oscillator module 612, and a SWIM and UART 614.

The microcontroller 604 communicates with the red/blue/green LED (indicator light 228) via a red and green LED control 616, and the battery module 606 communicates with the indicator light 228 via a blue LED control 618. The battery module 606 communicates with the microcontroller 604 via a battery voltage ADC 620. The battery module 606 sends 3.7 V nominal to the 2.5 V regulator 608, which sends 2.5 V to the microcontroller 604. The battery module 606 sends 3.7 V nominal to the Buck regulator and Baxandall oscillator module 612

The microcontroller 604 and SWIM and UART 614 are linked with respect to programming and calibration.

The output current measurement module 610 reads the emitter terminal 256 and reports to the microcontroller 604 via an output current ADC 622. The Buck regulator and Baxandall oscillator module 612 communicates with the microcontroller 604 via an output voltage ADC 624 and an oscillator current ADC 626. The microcontroller 604 communicates with the Buck regulator and Baxandall oscillator module 612 regarding the following microcontroller signals: manual PWM; feedback SSR; HVEN; and power PWM. The Buck regulator and Baxandall oscillator module 612 send up to 2 kV p-p to the voltage multiplier/ladder 630 on the daughter board 602, as continued in FIG. 62.

Still referring to FIG. 61, in one embodiment, manual PWM is two PWM signals used to start the oscillator to build up enough voltage so it can provide feedback for itself to ensure startup with the highly capacitive load. Feedback SSR is a control for a solid state relay used to allow the manual PWM signals to control the oscillator when off, and then when turned on, to allow the automatic feedback via the transformer after the oscillation is self-sustaining. HVEN is a high voltage enable signal to enable the Buck regulator that powers the oscillator. Finally, power PWM is a single PWM signal to set the desired Buck regulator operating point, and therefore the output power.

As shown in FIG. 62, the daughter board 602 of the electronics unit 224 includes a voltage multiplier/ladder 630 and a current limiting resistors module 632. The voltage multiplier/ladder 630 receives 2 kV p-p from the Buck regulator and Baxandall oscillator module 612 of the main board 600 and sends up to 21 kV (with no load) to the current limiting resistors module 632, which sends to the collector terminal 260.

FIG. 63 is a flow chart illustrating voltage modulation for the ionization filter of any of the embodiments of the electro-ionic device disclosed herein. As illustrated in FIG. 63, voltage and maximum current limit is set (700). The current is monitored to determine if acceptable (702). If current is not acceptable (704), then the voltage is adjusted downward (706). If current is acceptable, then continue operation (708) of the anode (710) and cathode (712) of the ionization filter 250 of the electro-ionic device.

As noted above, emitter/collector offset distance and voltage are variables that affect the performance of the ionization filter, as can the local elevation of where the ionization filter is being used. In calibrating the performance of the ionization filter for the local elevation and the overall situation, the operational point (e.g., operational voltage) can be set where there is effective particle removal in excess of 90% at the same time the ozone generation by the ionization filter remains at low levels. In some embodiments and situations, the optimal operational point may be where the particle reduction is maximized and the ozone generation over time remains below 0.1 parts per million in the inhaled air.

Once the ionization filter is calibrated for the optimal operational point for the local elevation and the overall situation, it may be recalibrated for a new elevation or new situation to again achieve that optimal operational point. This may be done electronically or mechanically. Some embodiments will rely solely on mechanical adjustment, and in doing so, the emitter/collector offset distance and/or geometry of the emitter/collector relationship can be modified/modulated. Mechanical modifications/modulations of the emitter/collector offset distance and/or geometry of the emitter/collector relationship for a new elevation or situation may be able to tune the ionization filter to within 12% to 20% of the former optimal operational point.

Some embodiments will rely solely on electronic recalibration, and in doing so, the voltage and current control can be modified/modulated to recalibrate for a new elevation or situation. Electronic modification/modulations of the voltage and current control may be able to tune the ionization filter to within 10% to 12% of the former optimal operational point.

Some embodiments can employ both mechanical and electronic recalibration. In doing so, the voltage and current control can be modified/modulated via electronics to get another 10% to 12% modification additional to the 12% to 20% provided via the mechanical recalibration.

In some embodiments, calibration and optimization of the performance of the ionization filter may occur at sea level because higher elevation will require lower voltage and should be easier on the electrical components.

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An electro-ionic device configured for being worn on the face of a person, the electro-ionic device comprising:
   at least two electrical conductors spaced apart from each other defining at least a portion of a respiratory pathway therebetween; and
   a circuit configured to apply a first voltage between the at least two electrical conductors during inspiration and a second voltage greater than the first voltage during expiration,
   wherein the circuit is configured to generate an amount of ozone during inspiration and expiration with the amount of ozone generated during inspiration being less than the amount of ozone generated during expiration.

2. The electro-ionic device of claim 1, further comprising at least one sensor, wherein the circuit is configured to detect inspiration and expiration based on the at least one sensor.

3. The electro-ionic device of claim 1, further comprising a fibrous filter positioned at least partially within the respiratory pathway.

4. The electro-ionic device of claim 1, wherein the first voltage is greater than 100 volts.

5. The electro-ionic device of claim 1, further comprising a portable DC power supply.

6. The electro-ionic device of claim 1, further comprising flow control vanes that result in at least one of spiral airflow, increased turbulence, or increased dwell time of airflow between the at least two electrical conductors.

7. The electro-ionic device of claim 1, wherein the at least two electrical conductors include an emitter and a collector, the collector radially outward from the emitter.

8. The electro-ionic device of claim 1, wherein the first voltage is between 100 volts and 20 kilovolts.

9. The electro-ionic device of claim 8, wherein the first voltage is between and including 500 volts and 6 kilovolts.

10. The electro-ionic device of claim 2, wherein the at least one sensor comprises at least one of a thermistor, a pressure sensor, or a strain gauge.

11. An electro-ionic device configured for being worn on the face of a person, the electro-ionic device comprising:
    an electrically insulating material having a continuous surface defining an opening, the opening configured to surround a respiration pathway;
    at least two electrical conductors spaced apart from each other, at least one of the at least two electrical conductors positioned within the respiration pathway; and
    a circuit configured to apply a voltage between the at least two electrical conductors during at least inspiration,
    wherein the circuit is configured to generate an amount of ozone during inspiration and expiration with the amount of ozone generated during inspiration being less than the amount of ozone generated during expiration.

12. The electro-ionic device of claim 11, further comprising at least one sensor, wherein the circuit is configured to detect inspiration and expiration based on the at least one sensor.

13. The electro-ionic device of claim 11, further comprising a fibrous filter positioned at least partially within the respiration pathway.

14. The electro-ionic device of claim 11, wherein the voltage is greater than 100 volts.

15. The electro-ionic device of claim 11, further comprising a portable DC power supply.

16. The electro-ionic device of claim 11, further comprising flow control vanes that result in at least one of spiral airflow, increased turbulence, or increased dwell time of airflow between the at least two electrical conductors.

17. The electro-ionic device of claim 11, wherein the at least two electrical conductors include an emitter and a collector, the collector radially extending about emitter.

18. The electro-ionic device of claim 11, wherein the voltage is between 100 volts and 20 kilovolts.

19. The electro-ionic device of claim 18, wherein the voltage is between and including 500 volts and 6 kilovolts.

20. The electro-ionic device of claim 12, wherein the at least one sensor comprises at least one of a thermistor, a pressure sensor, or a strain gauge.

21. A battery-powered electrostatic filter configured for being worn on the face of a person, the battery-powered electrostatic filter comprising:
    an electrically insulating material having a continuous surface defining an opening, the opening configured to surround a respiration pathway;
    at least two electrical conductors spaced apart from each other, at least one of the at least two electrical conductors positioned within the respiration pathway; and
    a circuit configured to apply a first voltage between the at least two electrical conductors during inspiration and a second voltage greater than the first voltage during expiration,
    wherein the circuit is configured to generate an amount of ozone during inspiration and expiration with the amount of ozone generated during inspiration being less than the amount of ozone generated during expiration.

22. The battery-powered electrostatic filter of claim 21, further comprising at least one sensor, wherein the circuit is configured to detect inspiration and expiration based on the at least one sensor.

23. The battery-powered electrostatic filter of claim 21, further comprising a fibrous filter positioned at least partially within the respiration pathway.

24. The battery-powered electrostatic filter of claim 21, wherein the first voltage is greater than 100 volts.

25. The battery-powered electrostatic filter of claim 21, further comprising flow control vanes that result in at least one of spiral airflow, increased turbulence, or increased dwell time of airflow between the at least two electrical conductors.

26. The battery-powered electrostatic filter of claim 21, wherein the at least two electrical conductors include an emitter and a collector, the collector radially outward from the emitter.

27. The battery-powered electrostatic filter of claim 21, wherein the first voltage is between 100 volts and 20 kilovolts.

28. The battery-powered electrostatic filter of claim 27, wherein the first voltage is between and including 500 volts and 6 kilovolts.

29. The battery-powered electrostatic filter of claim 22, wherein the at least one sensor comprises at least one of a thermistor, a pressure sensor, or a strain gauge.

\* \* \* \* \*